(12) United States Patent
Zhao et al.

(10) Patent No.: US 10,696,699 B2
(45) Date of Patent: Jun. 30, 2020

(54) CHARGED LINKERS AND THEIR USES FOR CONJUGATION

(71) Applicant: HANGZHOU DAC BIOTECH CO., LTD., Hangzhou (CN)

(72) Inventors: Robert Yongxin Zhao, Hangzhou (CN); Xing Li, Hangzhou (CN); Yuangyuang Huang, Hangzhou (CN); Qingliang Yang, Hangzhou (CN)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 0 days.

(21) Appl. No.: 16/228,130

(22) Filed: Dec. 20, 2018

(65) Prior Publication Data

US 2019/0127399 A1  May 2, 2019

Related U.S. Application Data

(62) Division of application No. 15/118,726, filed as application No. PCT/CN2014/072769 on Feb. 28, 2014, now Pat. No. 10,464,955.

(51) Int. Cl.
| | |
|---|---|
| *C07F 9/58* | (2006.01) |
| *C07F 9/30* | (2006.01) |
| *C07F 9/572* | (2006.01) |
| *C07F 9/6558* | (2006.01) |
| *C07F 9/6561* | (2006.01) |
| *A61K 47/68* | (2017.01) |
| *A61K 38/07* | (2006.01) |
| *C07F 9/32* | (2006.01) |

(52) U.S. Cl.
CPC ............ *C07F 9/301* (2013.01); *A61K 38/07* (2013.01); *A61K 47/6803* (2017.08); *A61K 47/6807* (2017.08); *A61K 47/6809* (2017.08); *A61K 47/6811* (2017.08); *A61K 47/6817* (2017.08); *A61K 47/6851* (2017.08); *A61K 47/6889* (2017.08); *C07F 9/302* (2013.01); *C07F 9/3211* (2013.01); *C07F 9/3217* (2013.01); *C07F 9/572* (2013.01); *C07F 9/58* (2013.01); *C07F 9/6561* (2013.01); *C07F 9/65583* (2013.01); *C07F 9/65616* (2013.01)

(58) Field of Classification Search
CPC ...... C07F 9/301; C07F 9/3211; C07F 9/3217; C07F 9/5721; C07F 9/582; C07F 9/65583; C07F 9/65616; A61K 38/07; A61K 47/48415; A61K 47/48569; A61K 47/48715
See application file for complete search history.

(56) References Cited

U.S. PATENT DOCUMENTS

| | | | |
|---|---|---|---|
| 4,000,304 A | 12/1976 | Wu et al. | |
| 4,150,584 A | 4/1979 | Theijsmeijer | |
| 4,169,888 A | 10/1979 | Hanka et al. | |
| 4,256,746 A | 3/1981 | Miyashita et al. | |
| 4,294,757 A | 10/1981 | Asai | |
| 4,307,016 A | 12/1981 | Asai et al. | |
| 4,313,946 A | 2/1982 | Powell et al. | |
| 4,315,929 A | 2/1982 | Freedman et al. | |
| 4,322,348 A | 3/1982 | Asai et al. | |
| 4,331,598 A | 5/1982 | Hasegawa et al. | |
| 4,341,761 A | 7/1982 | Ganfield et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,391,904 A | 7/1983 | Litman et al. | |
| 4,399,121 A | 8/1983 | Albarella et al. | |
| 4,414,205 A | 11/1983 | Pettit | |
| 4,424,219 A | 1/1984 | Hashimoto et al. | |
| 4,427,587 A | 1/1984 | Kaneko et al. | |
| 4,427,783 A | 1/1984 | Newman et al. | |
| 4,444,887 A | 4/1984 | Hoffmann | |
| 4,450,254 A | 5/1984 | Isley et al. | |
| 4,451,570 A | 5/1984 | Royston et al. | |
| 4,464,467 A | 8/1984 | Hatori et al. | |
| 4,466,917 A | 8/1984 | Nussenzweig et al. | |
| 4,472,500 A | 9/1984 | Milstein et al. | |
| 4,491,632 A | 1/1985 | Wands et al. | |
| 4,493,795 A | 1/1985 | Nestor, Jr. et al. | |
| 4,493,890 A | 1/1985 | Morris | |
| 4,508,647 A | 4/1985 | Hatori et al. | |
| 4,563,304 A | 1/1986 | Carlsson et al. | |
| 4,663,453 A | 5/1987 | Glamkowski et al. | |
| 4,671,958 A | 6/1987 | Rodwell et al. | |
| 4,680,338 A | 7/1987 | Sundoro | |
| 4,683,230 A | 7/1987 | Tsunakawa et al. | |

(Continued)

FOREIGN PATENT DOCUMENTS

| | | |
|---|---|---|
| CA | 2 710 693 A1 | 1/2011 |
| CN | 101784565 A | 7/2010 |

(Continued)

OTHER PUBLICATIONS

C.B. Carlson et al., 2 ACS Chemical Biology, (2007) (Year: 2007).*
M.L. Chiu et al., Current Opinion in Structural Biology, 163-173 (2016) (Year: 2016).*
I.A. Wilson et al., ., Current Opinion in Structural Biology, 1134-118 (1993) (Year: 1993).*
B. Sammet et al., 1 Pharmaceutical Patent Analyst (2012) (Year: 2012).*
R. Cohen et al., 74 Cancer Reseach, (2014) (Year: 2014).*
F. Franks, Proteins, in Protein Biotechnology (1993) (Year: 1993).*
A. Florence et al., 12 Drug Targeting, 65-70 (2004) (Year: 2004).*
S. Gelperina et al., 172 American Journal of Respiratory and Critical Care Medicine, 1487-1490 (2005) (Year: 2005).*
Z. Ahmad et al., 4 RSC Adv., 17028-17038 (2014) (Year: 2014).*
X. Pang et al., 18 Drug Discovery Today, 1316-1322 (2013) (Year: 2013).*

(Continued)

*Primary Examiner* — Alexander R Pagano
(74) *Attorney, Agent, or Firm* — Buchanan Ingersoll & Rooney PC

(57) ABSTRACT

Cell binding agent-drug conjugates comprising phosphinate-based charged linkers and methods of using such linkers and conjugates are provided.

25 Claims, 24 Drawing Sheets

(56) References Cited

U.S. PATENT DOCUMENTS

| | | |
|---|---|---|
| 4,723,003 A | 2/1988 | Glamkowski et al. |
| 4,723,007 A | 2/1988 | Glamkowski et al. |
| 4,753,894 A | 6/1988 | Frankel et al. |
| 4,761,412 A | 8/1988 | Glamkowski et al. |
| 4,764,368 A | 8/1988 | Blattler et al. |
| 4,764,616 A | 8/1988 | Glamkowski et al. |
| 4,816,444 A | 3/1989 | Pettit et al. |
| 4,816,567 A | 3/1989 | Cabilly et al. |
| 4,879,278 A | 11/1989 | Pettit et al. |
| 4,912,227 A | 3/1990 | Kelly et al. |
| 4,923,990 A | 5/1990 | Nakano et al. |
| 4,935,362 A | 6/1990 | Tsunakawa et al. |
| 4,943,628 A | 7/1990 | Rosen et al. |
| 4,952,394 A | 8/1990 | Senter |
| 4,956,303 A | 9/1990 | Self |
| 4,970,198 A | 11/1990 | Lee et al. |
| 4,975,278 A | 12/1990 | Senter et al. |
| 4,978,744 A | 12/1990 | Pettit et al. |
| 4,978,757 A | 12/1990 | Kelly et al. |
| 4,994,578 A | 2/1991 | Ohba et al. |
| 5,006,651 A | 4/1991 | Broadhurst et al. |
| 5,037,993 A | 8/1991 | Ohba et al. |
| 5,053,394 A | 10/1991 | Ellestad et al. |
| 5,070,092 A | 12/1991 | Kanda et al. |
| 5,084,468 A | 1/1992 | Saito et al. |
| 5,094,848 A | 3/1992 | Brixner |
| 5,101,038 A | 3/1992 | Nakano et al. |
| 5,106,951 A | 4/1992 | Morgan, Jr. et al. |
| 5,108,912 A | 4/1992 | Lee et al. |
| 5,117,006 A | 5/1992 | Saito et al. |
| 5,122,368 A | 6/1992 | Greenfield et al. |
| 5,137,877 A | 8/1992 | Kaneko et al. |
| 5,138,059 A | 8/1992 | Takahashi et al. |
| 5,141,648 A | 8/1992 | Hylarides et al. |
| 5,146,064 A | 9/1992 | Poirier |
| 5,147,786 A | 9/1992 | Feng et al. |
| 5,165,923 A | 11/1992 | Thorpe et al. |
| 5,169,774 A | 12/1992 | Frankel et al. |
| 5,177,016 A | 1/1993 | Balsari et al. |
| 5,187,186 A | 2/1993 | Kanda et al. |
| 5,208,020 A | 5/1993 | Chari et al. |
| 5,208,323 A | 5/1993 | Page et al. |
| 5,223,409 A | 6/1993 | Ladner et al. |
| 5,225,539 A | 7/1993 | Winter |
| 5,264,586 A | 11/1993 | Nicolaou et al. |
| 5,286,637 A | 2/1994 | Veronese et al. |
| 5,288,514 A | 2/1994 | Ellman |
| 5,324,483 A | 6/1994 | Cody et al. |
| 5,332,740 A | 7/1994 | Saito et al. |
| 5,332,837 A | 7/1994 | Kelly et al. |
| 5,334,528 A | 8/1994 | Stanker et al. |
| 5,384,412 A | 1/1995 | Nicolaou et al. |
| 5,403,484 A | 4/1995 | Ladner et al. |
| 5,410,024 A | 4/1995 | Pettit et al. |
| 5,414,064 A | 5/1995 | Lux |
| 5,416,064 A | 5/1995 | Chari et al. |
| 5,427,908 A | 6/1995 | Dower et al. |
| 5,436,149 A | 7/1995 | Barnes |
| 5,475,011 A | 12/1995 | Ojima et al. |
| 5,475,092 A | 12/1995 | Chari et al. |
| 5,495,009 A | 2/1996 | Matteucci et al. |
| 5,521,284 A | 5/1996 | Pettit et al. |
| 5,530,097 A | 6/1996 | Pettit et al. |
| 5,530,101 A | 6/1996 | Queen et al. |
| 5,543,390 A | 8/1996 | Yatvin et al. |
| 5,545,806 A | 8/1996 | Lonberg et al. |
| 5,547,667 A | 8/1996 | Angelucci et al. |
| 5,554,725 A | 9/1996 | Pettit |
| 5,563,250 A | 10/1996 | Hylarides et al. |
| 5,569,825 A | 10/1996 | Lonberg et al. |
| 5,571,698 A | 11/1996 | Ladner et al. |
| 5,573,922 A | 11/1996 | Hoess et al. |
| 5,580,717 A | 12/1996 | Dower et al. |
| 5,585,089 A | 12/1996 | Queen et al. |
| 5,585,499 A | 12/1996 | Chari et al. |
| 5,587,161 A | 12/1996 | Burke et al. |
| 5,595,499 A | 1/1997 | Zander et al. |
| 5,599,902 A | 2/1997 | Pettit et al. |
| 5,606,017 A | 2/1997 | Willner et al. |
| 5,606,040 A | 2/1997 | McGahren et al. |
| 5,622,929 A | 4/1997 | Willner et al. |
| 5,625,126 A | 4/1997 | Lonberg et al. |
| 5,629,197 A | 5/1997 | Ring et al. |
| 5,629,430 A | 5/1997 | Terashima et al. |
| 5,633,425 A | 5/1997 | Lonberg et al. |
| 5,635,483 A | 6/1997 | Pettit et al. |
| 5,641,780 A | 6/1997 | Amishiro et al. |
| 5,654,399 A | 8/1997 | Sakakibara et al. |
| 5,660,829 A | 8/1997 | Burke et al. |
| 5,661,016 A | 8/1997 | Lonberg et al. |
| 5,663,149 A | 9/1997 | Pettit et al. |
| 5,665,860 A | 9/1997 | Pettit et al. |
| 5,679,700 A | 10/1997 | Caldwell et al. |
| 5,686,237 A | 11/1997 | Al-Bayati |
| 5,693,762 A | 12/1997 | Queen et al. |
| 5,703,080 A | 12/1997 | Nakakura et al. |
| 5,708,146 A | 1/1998 | Willner et al. |
| 5,712,374 A | 1/1998 | Kuntsmann et al. |
| 5,714,586 A | 2/1998 | Kuntsmann et al. |
| 5,728,849 A | 3/1998 | Bouchard et al. |
| 5,739,116 A | 4/1998 | Hamann et al. |
| 5,739,350 A | 4/1998 | Kelly et al. |
| 5,741,892 A | 4/1998 | Barlozzari et al. |
| 5,767,236 A | 6/1998 | Kim et al. |
| 5,767,237 A | 6/1998 | Sakakibara et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,773,435 A | 6/1998 | Kadow et al. |
| 5,780,588 A | 7/1998 | Pettit et al. |
| 5,786,377 A | 7/1998 | Garcia et al. |
| 5,786,486 A | 7/1998 | Fukuda et al. |
| 5,789,650 A | 8/1998 | Lonberg et al. |
| 5,811,452 A | 9/1998 | Ojima et al. |
| 5,814,318 A | 9/1998 | Lonberg et al. |
| 5,821,337 A | 10/1998 | Carter et al. |
| 5,824,805 A | 10/1998 | King et al. |
| 5,840,699 A | 11/1998 | Sakakibara et al. |
| 5,846,545 A | 12/1998 | Chari et al. |
| 5,859,205 A | 1/1999 | Adair et al. |
| 5,874,299 A | 2/1999 | Lonberg et al. |
| 5,877,296 A | 3/1999 | Hamann et al. |
| 5,877,397 A | 3/1999 | Lonberg et al. |
| 5,880,122 A | 3/1999 | Trybulski et al. |
| 5,880,270 A | 3/1999 | Berninger et al. |
| 5,885,793 A | 3/1999 | Griffiths et al. |
| 5,922,545 A | 7/1999 | Mattheakis et al. |
| 5,939,598 A | 8/1999 | Kucherlapati et al. |
| 5,962,216 A | 10/1999 | Trouet et al. |
| 5,965,537 A | 10/1999 | Ritter et al. |
| 5,969,108 A | 10/1999 | McCafferty et al. |
| 5,985,908 A | 11/1999 | Boger |
| 5,998,593 A * | 12/1999 | Huff .................... C07D 311/16 536/4.1 |
| 6,004,934 A | 12/1999 | Sakakibara et al. |
| 6,015,562 A | 1/2000 | Hinman et al. |
| 6,033,876 A | 3/2000 | Lemke et al. |
| 6,034,065 A | 3/2000 | Pettit et al. |
| 6,048,720 A | 4/2000 | Dalborg et al. |
| 6,054,297 A | 4/2000 | Carter et al. |
| 6,054,561 A | 4/2000 | Ring |
| 6,060,608 A | 5/2000 | Boger |
| 6,066,742 A | 5/2000 | Fukuda et al. |
| 6,075,181 A | 6/2000 | Kucherlapati et al. |
| 6,103,236 A | 8/2000 | Suzawa et al. |
| 6,111,166 A | 8/2000 | van de Winkel |
| 6,114,598 A | 9/2000 | Kucherlapati et al. |
| 6,124,310 A | 9/2000 | Denny et al. |
| 6,124,431 A | 9/2000 | Sakakibara et al. |
| 6,130,237 A | 10/2000 | Denny et al. |
| 6,132,722 A | 10/2000 | Siemers et al. |
| 6,143,721 A | 11/2000 | Janssen et al. |
| 6,143,901 A | 11/2000 | Dervan |

(56) References Cited

U.S. PATENT DOCUMENTS

| | | |
|---|---|---|
| 6,146,658 A | 11/2000 | Bosslet et al. |
| 6,150,584 A | 11/2000 | Kucherlapati et al. |
| 6,162,930 A | 12/2000 | Pinney et al. |
| 6,162,963 A | 12/2000 | Kucherlapati et al. |
| 6,172,197 B1 | 1/2001 | McCafferty et al. |
| 6,180,370 B1 | 1/2001 | Queen et al. |
| 6,194,612 B1 | 2/2001 | Boger et al. |
| 6,207,418 B1 | 3/2001 | Hori et al. |
| 6,214,345 B1 | 4/2001 | Firestone et al. |
| 6,239,104 B1 | 5/2001 | Pettit et al. |
| 6,258,360 B1 * | 7/2001 | von Borstel .......... C07C 311/19 424/182.1 |
| 6,262,271 B1 | 7/2001 | Boger |
| 6,281,354 B1 | 8/2001 | Boger |
| 6,309,646 B1 | 10/2001 | Lees |
| 6,310,209 B1 | 10/2001 | Boger |
| 6,323,315 B1 | 11/2001 | Pettit et al. |
| 6,329,497 B1 | 12/2001 | Boger |
| 6,333,410 B1 | 12/2001 | Chari et al. |
| 6,340,701 B1 | 1/2002 | Chari et al. |
| 6,342,219 B1 | 1/2002 | Thorpe et al. |
| 6,342,221 B1 | 1/2002 | Thorpe et al. |
| 6,342,480 B1 | 1/2002 | Trouet et al. |
| 6,344,451 B1 | 2/2002 | Steffan et al. |
| 6,372,738 B2 | 4/2002 | Chari et al. |
| 6,391,913 B1 | 5/2002 | Page et al. |
| 6,407,213 B1 | 6/2002 | Carter et al. |
| 6,436,931 B1 | 8/2002 | Chari et al. |
| 6,441,163 B1 | 8/2002 | Chari et al. |
| 6,486,326 B2 | 11/2002 | Boger |
| 6,512,101 B1 | 1/2003 | King et al. |
| 6,521,404 B1 | 2/2003 | Griffiths et al. |
| 6,534,660 B1 | 3/2003 | Yougxin et al. |
| 6,544,731 B1 | 4/2003 | Griffiths et al. |
| 6,548,530 B1 | 4/2003 | Boger |
| 6,555,313 B1 | 4/2003 | Griffiths et al. |
| 6,555,693 B2 | 4/2003 | Ge et al. |
| 6,562,806 B1 | 5/2003 | Thurston et al. |
| 6,566,336 B1 | 5/2003 | Sugiyama et al. |
| 6,569,834 B1 | 5/2003 | Pettit et al. |
| 6,586,618 B1 | 7/2003 | Zhao et al. |
| 6,589,979 B2 | 7/2003 | Bombardelli et al. |
| 6,593,081 B1 | 7/2003 | Griffiths et al. |
| 6,596,541 B2 | 7/2003 | Murphy et al. |
| 6,596,757 B1 | 7/2003 | Chari et al. |
| 6,608,192 B1 | 8/2003 | Thurston et al. |
| 6,620,911 B1 | 9/2003 | Pettit et al. |
| 6,630,579 B2 | 10/2003 | Chari et al. |
| 6,639,055 B1 | 10/2003 | Carter et al. |
| 6,660,856 B2 | 12/2003 | Wang |
| 6,706,708 B2 | 3/2004 | Chari et al. |
| 6,716,821 B2 | 4/2004 | Zhao et al. |
| 6,747,144 B1 | 6/2004 | Thurston et al. |
| 6,756,397 B2 | 6/2004 | Zhao et al. |
| 6,759,509 B1 | 7/2004 | King et al. |
| 6,762,179 B2 | 7/2004 | Cochran et al. |
| 6,797,492 B2 | 9/2004 | Daugherty et al. |
| 6,800,622 B1 | 10/2004 | Kamal et al. |
| 6,884,799 B2 | 4/2005 | Kamal et al. |
| 6,884,869 B2 | 4/2005 | Senter et al. |
| 6,897,034 B2 | 5/2005 | Bebbington et al. |
| 6,909,006 B1 | 6/2005 | Thurston et al. |
| 6,913,748 B2 | 7/2005 | Widdison |
| 6,946,272 B1 | 9/2005 | Powell et al. |
| 6,946,455 B2 | 9/2005 | Sugiyama et al. |
| 6,951,853 B1 | 10/2005 | Kamal et al. |
| 6,977,254 B2 | 12/2005 | Failli et al. |
| 6,979,684 B1 | 12/2005 | Kamal et al. |
| 6,989,452 B2 | 1/2006 | Ng et al. |
| 7,008,942 B2 | 3/2006 | Chari et al. |
| 7,015,215 B2 | 3/2006 | Kamal et al. |
| 7,022,699 B2 | 4/2006 | Failli et al. |
| 7,049,311 B1 | 5/2006 | Thurston et al. |
| 7,049,316 B2 | 5/2006 | Zhao et al. |
| 7,056,913 B2 | 6/2006 | Kamal et al. |
| 7,064,120 B2 | 6/2006 | Failli et al. |
| 7,067,511 B2 | 6/2006 | Thurston et al. |
| 7,071,311 B2 | 7/2006 | Radka et al. |
| 7,087,600 B2 | 8/2006 | Ng et al. |
| 7,090,843 B1 | 8/2006 | Francisco et al. |
| 7,091,186 B2 | 8/2006 | Senter et al. |
| 7,097,840 B2 | 8/2006 | Erickson et al. |
| 7,098,305 B2 | 8/2006 | Deghenghi et al. |
| 7,098,308 B2 | 8/2006 | Senter et al. |
| 7,109,193 B2 | 9/2006 | Failli et al. |
| 7,115,573 B2 | 10/2006 | Pickford et al. |
| 7,129,261 B2 | 10/2006 | Ng et al. |
| 7,173,026 B2 | 2/2007 | Kamal et al. |
| 7,186,851 B2 | 3/2007 | Baloglu |
| 7,189,710 B2 | 3/2007 | Kamal et al. |
| 7,202,239 B2 | 4/2007 | Failli et al. |
| 7,214,663 B2 | 5/2007 | Bebbington et al. |
| 7,217,819 B2 | 5/2007 | Chari et al. |
| 7,223,837 B2 | 5/2007 | De Groot et al. |
| 7,265,105 B2 | 9/2007 | Thurston et al. |
| 7,276,497 B2 | 10/2007 | Chari et al. |
| 7,276,499 B2 | 10/2007 | Chari et al. |
| 7,301,019 B2 | 11/2007 | Widdison et al. |
| 7,303,749 B1 | 12/2007 | Chari |
| 7,304,032 B2 | 12/2007 | Bebbington et al. |
| 7,312,210 B2 | 12/2007 | Kamal et al. |
| 7,326,700 B2 | 2/2008 | Failli et al. |
| 7,329,507 B2 | 2/2008 | Pickford et al. |
| 7,329,760 B2 | 2/2008 | Zhao et al. |
| 7,368,565 B2 | 5/2008 | Chari et al. |
| 7,375,078 B2 | 5/2008 | Feng |
| 7,388,026 B2 | 6/2008 | Zhao et al. |
| 7,407,951 B2 | 8/2008 | Thurston et al. |
| 7,411,063 B2 | 8/2008 | Widdison et al. |
| 7,429,658 B2 | 9/2008 | Howard et al. |
| 7,462,352 B2 | 12/2008 | Hansen et al. |
| 7,498,298 B2 | 3/2009 | Doronina et al. |
| 7,498,302 B2 | 3/2009 | Ng et al. |
| 7,507,420 B2 | 3/2009 | Ng et al. |
| 7,511,032 B2 | 3/2009 | Liu et al. |
| 7,528,126 B2 | 5/2009 | Howard et al. |
| 7,528,128 B2 | 5/2009 | Ahmed et al. |
| 7,553,816 B2 | 6/2009 | Senter et al. |
| 7,557,099 B2 | 7/2009 | Howard et al. |
| 7,569,358 B2 | 8/2009 | Salamone et al. |
| 7,598,290 B2 | 10/2009 | Miller et al. |
| 7,608,615 B2 | 10/2009 | Ahmed et al. |
| 7,612,062 B2 | 11/2009 | Gregson et al. |
| 7,655,660 B2 | 2/2010 | Zhao et al. |
| 7,655,661 B2 | 2/2010 | Zhao et al. |
| 7,659,241 B2 | 2/2010 | Senter et al. |
| 7,662,387 B2 | 2/2010 | Law et al. |
| 7,667,054 B2 | 2/2010 | Miller et al. |
| 7,678,787 B2 | 3/2010 | Failli et al. |
| 7,691,848 B2 | 4/2010 | Failli et al. |
| 7,691,962 B2 | 4/2010 | Boyd et al. |
| 7,704,924 B2 | 4/2010 | Thurston et al. |
| 7,741,319 B2 | 6/2010 | Howard et al. |
| 7,745,394 B2 | 6/2010 | Doronina et al. |
| 7,754,681 B2 | 7/2010 | Feng |
| 7,754,885 B2 | 7/2010 | Hoefle et al. |
| 7,776,814 B2 | 8/2010 | Domling et al. |
| 7,803,903 B2 | 9/2010 | Kratz |
| 7,816,377 B2 | 10/2010 | Domling et al. |
| 7,829,531 B2 | 11/2010 | Senter et al. |
| 7,833,992 B2 | 11/2010 | Vargeese et al. |
| 7,834,005 B2 | 11/2010 | Liu et al. |
| 7,837,980 B2 | 11/2010 | Alley et al. |
| 7,837,995 B2 | 11/2010 | Goldenberg |
| 7,843,005 B2 | 11/2010 | Nowak |
| 7,851,432 B2 | 12/2010 | Chari et al. |
| 7,851,437 B2 | 12/2010 | Senter et al. |
| 7,902,338 B2 | 3/2011 | Hansen et al. |
| 7,906,545 B2 | 3/2011 | Zhao et al. |
| 7,910,594 B2 | 3/2011 | Vlahov et al. |
| 7,937,980 B2 | 5/2011 | Hessberger et al. |
| 7,939,434 B2 | 5/2011 | Tseng et al. |
| 7,964,566 B2 | 6/2011 | Doronina et al. |
| 7,964,567 B2 | 6/2011 | Doronina et al. |

(56) References Cited

U.S. PATENT DOCUMENTS

| | | | |
|---|---|---|---|
| 7,968,586 B2 | 6/2011 | Gangwar et al. | |
| 7,989,434 B2 | 8/2011 | Feng | |
| 7,994,135 B2 | 8/2011 | Doronina et al. | |
| 7,999,083 B2 | 8/2011 | Govindan et al. | |
| 8,012,978 B2 | 9/2011 | Zhao et al. | |
| 8,034,808 B2 | 10/2011 | Delavault et al. | |
| 8,053,205 B2 | 11/2011 | Salamone et al. | |
| 8,084,586 B2 | 12/2011 | Salamone et al. | |
| 8,153,627 B2 | 4/2012 | Kamal et al. | |
| 8,153,768 B2 | 4/2012 | Kunz et al. | |
| 8,163,736 B2 | 4/2012 | Gauzy et al. | |
| 8,163,888 B2 | 4/2012 | Steeves et al. | |
| 8,236,319 B2 | 8/2012 | Chari et al. | |
| 9,260,483 B2 * | 2/2016 | Notni | C07K 7/64 |
| 9,345,768 B2 * | 5/2016 | Jordan | A61K 9/0009 |
| 10,131,682 B2 | 11/2018 | Zhao | |
| 2003/0195196 A1 | 10/2003 | Thurston et al. | |
| 2004/0249130 A1 | 12/2004 | Stanton et al. | |
| 2006/0022925 A1 | 2/2006 | Hara et al. | |
| 2006/0074008 A1 | 4/2006 | Senter et al. | |
| 2006/0217360 A1 | 9/2006 | Hoefle et al. | |
| 2007/0041901 A1 | 2/2007 | Diener et al. | |
| 2009/0088390 A1 | 4/2009 | Nishizawa | |
| 2009/0176253 A1 | 7/2009 | Bieniarz et al. | |
| 2009/0274713 A1 | 11/2009 | Chari et al. | |
| 2010/0041872 A1 | 2/2010 | Defrees et al. | |
| 2010/0062008 A1 | 3/2010 | Senter et al. | |
| 2010/0074840 A1 | 3/2010 | Griffiths et al. | |
| 2010/0104589 A1 | 4/2010 | Govindan et al. | |
| 2010/0136652 A1 | 6/2010 | Bieniarz et al. | |
| 2010/0189727 A1 | 7/2010 | Rodeck et al. | |
| 2010/0203007 A1 | 8/2010 | Li et al. | |
| 2010/0316656 A1 | 12/2010 | Bouchard et al. | |
| 2010/0323973 A1 | 12/2010 | Leamon et al. | |
| 2011/0021568 A1 | 1/2011 | Ellman et al. | |
| 2011/0027274 A1 | 2/2011 | Cheng et al. | |
| 2011/0064666 A1 | 3/2011 | Ogawa et al. | |
| 2011/0064752 A1 | 3/2011 | Hutchinson et al. | |
| 2011/0064753 A1 | 3/2011 | Senter et al. | |
| 2011/0076722 A1 | 3/2011 | Takahashi | |
| 2011/0134826 A1 | 6/2011 | Yang et al. | |
| 2011/0263650 A1 | 10/2011 | Ellman et al. | |
| 2011/0288152 A1 * | 11/2011 | Low | A61K 51/088 514/44 A |
| 2011/0293513 A1 | 12/2011 | Govindan et al. | |
| 2012/0034295 A1 | 2/2012 | Spiegel et al. | |
| 2012/0082617 A1 | 4/2012 | Govindan et al. | |
| 2012/0129779 A1 | 5/2012 | Richter | |
| 2012/0165537 A1 | 6/2012 | Li et al. | |
| 2012/0201809 A1 | 8/2012 | Bhat et al. | |
| 2013/0095123 A1 | 4/2013 | Lerchen et al. | |
| 2015/0250896 A1 | 9/2015 | Zhao | |
| 2016/0207949 A1 | 7/2016 | Zhao | |
| 2017/0152274 A1 | 6/2017 | Zhao et al. | |
| 2017/0327486 A1 | 11/2017 | Li et al. | |
| 2019/0127400 A1 | 5/2019 | Zhao et al. | |
| 2019/0127401 A1 | 5/2019 | Zhao et al. | |

FOREIGN PATENT DOCUMENTS

| | | | |
|---|---|---|---|
| DE | 196 38 870 A1 | 3/1998 | |
| DE | 100 08 089 A1 | 10/2001 | |
| DE | 102 41 152 A1 | 3/2004 | |
| DE | 102 54 439 A1 | 6/2004 | |
| DE | 103 09 005 A1 | 9/2004 | |
| DE | 10 2004 030 227 A1 | 1/2006 | |
| EP | 0209848 A2 * | 1/1987 | C07F 9/301 |
| EP | 2 174 947 A1 | 4/2010 | |
| JP | 2000-511889 A | 9/2000 | |
| JP | 2011-519864 A | 7/2011 | |
| WO | 89/10961 A1 | 11/1989 | |
| WO | 01/36003 A2 | 5/2001 | |
| WO | 01/38318 A1 | 5/2001 | |
| WO | 02/077036 A2 | 10/2002 | |
| WO | 03/001968 A2 | 1/2003 | |
| WO | 03/077834 A2 | 9/2003 | |
| WO | 2004/005269 A1 | 1/2004 | |
| WO | 2004/005326 A2 | 1/2004 | |
| WO | 2004/005327 A1 | 1/2004 | |
| WO | 2005/058367 A2 | 6/2005 | |
| WO | 2005/110455 A2 | 11/2005 | |
| WO | 2006/033913 A2 | 3/2006 | |
| WO | 2006/056464 A2 | 6/2006 | |
| WO | 2006/096754 A2 | 9/2006 | |
| WO | 2007/052169 A2 | 5/2007 | |
| WO | 2008/002993 A2 | 1/2008 | |
| WO | 2008/034019 A2 | 3/2008 | |
| WO | 2008/070291 A2 | 6/2008 | |
| WO | 2008/076333 A2 | 6/2008 | |
| WO | 2008/112873 A2 | 9/2008 | |
| WO | 2008/125116 A2 | 10/2008 | |
| WO | 2008/138561 A1 | 11/2008 | |
| WO | 2009/002993 A1 | 12/2008 | |
| WO | 2009/012958 A2 | 1/2009 | |
| WO | 2009/026177 A1 | 2/2009 | |
| WO | 2009/055562 A1 | 4/2009 | |
| WO | 2009/095447 A1 | 8/2009 | |
| WO | 2009/134279 A1 | 11/2009 | |
| WO | 2009/139863 A2 | 11/2009 | |
| WO | 2010/033733 A1 | 3/2010 | |
| WO | 2010/034724 A1 | 4/2010 | |
| WO | 2012/095347 A2 | 7/2012 | |
| WO | 2012/143495 A2 | 10/2012 | |
| WO | 2014/009774 A1 | 1/2014 | |
| WO | 2014/080251 A1 | 5/2014 | |
| WO | WO-2014080251 A1 * | 5/2014 | A61K 31/10 |

OTHER PUBLICATIONS

F. Kratz, 132 Journal of Controlled release, 171-183 (2008) (Year: 2008).*
J. Wang et al., International Journal of Medicine 765-774 (2011) (Year: 2011).*
Clackson et al., "Making antibody fragments using phage display libraries," Nature, (Aug. 15, 1991), vol. 352, pp. 624-628. (5 pages).
Harlow et al., "Antibodies: A Laboratory Manual," Cold Spring Harbor, New York: Cold Spring Harbor Laboratory, (1988). (105 pages).
Hurwitz et al., "The Covalent Binding of Daunomycin and Adriamycin to Antibodies, with Retention of Both Drug and Antibody Activities," Cancer Research, (May 1975), vol. 35, No. 5, pp. 1175-1181. (7 pages).
Jain, Kewal K., "Drug Delivery Systems," Methods in Molecular Biology, Humana Press, (2008). (59 pages).
Köhler et al., "Continuous cultures of fused cells secreting antibody of predefined specificity," Nature, (Aug. 7, 1975), vol. 256, No. 5517, pp. 495-497. (3 pages).
Lee et al., "Designing dendrimers for biological applications," Nature Biotechnology, (Dec. 2005), vol. 23, No. 12, pp. 1517-1526. (10 pages).
Ojima et al., "Tumor-Specific Novel Taxoid-Monoclonal Antibody Conjugates," Journal of Medicinal Chemistry, (2002), vol. 45, pp. 5620-5623. (4 pages).
"Organic Substituent Groups and Ring Systems," CRC Handbook of Chemistry and Physics, p. 2-25 and p. 2-26. (2 pages).
Pietersz et al., "Immunochemotherapy of a Murine Thymoma with the Use of Idarubicin Monoclonal Antibody Conjugates," Cancer Research, (Feb. 15, 1988), vol. 48, No. 4, pp. 926-931. (6 pages).
Reddy et al., "In Vivo Structural Activity and Optimization Studies of Folate-Tubulysin Conjugates," Molecular Pharmaceutics, (Jul. 24, 2009), vol. 6, No. 5, pp. 1518-1525. (8 pages).
Sun et al., "Design of Antibody-Maytansinoid Conjugates Allows for Efficient Detoxification via Liver Metabolism," Bioconjugate Chemistry, (2011), vol. 22, No. 4, pp. 728-735. (8 pages).
Türk et al., "Relevance of multidrug resistance in the age of targeted therapy," Current Opinion in Drug Discovery & Development, (2009), vol. 22, No. 2, pp. 246-252. (7 pages).
Yang et al. "Doxorubicin conjugated with a monoclonal antibody directed to a human melanoma-associated proteoglycan suppresses

(56) References Cited

OTHER PUBLICATIONS the growth of established tumor xenografts in nude mice," Proceedings of the National Academy of Sciences of the United States of America, (Feb. 1988), vol. 85, No. 4, pp. 1189-1193. (5 pages).
Yauch et al., "Recent advances in pathway-targeted cancer drug therapies emerging from cancer genome analysis," Current Opinion in Genetics & Development, (Feb. 7, 2012), vol. 22, No. 1, pp. 45-49. (5 pages).
Zhao et al., "Synthesis and Evaluation of Hydrophilic Linkers for Antibody-Maytansinoid Conjugates," Journal of Medicinal Chemistry, (Apr. 25, 2011), vol. 54, No. 10, pp. 3606-3623. (18 pages).
Jeffrey et al., "Design, Synthesis, and in Vitro Evaluation of Dipeptide-Based Antibody Minor Groove Binder Conjugates," Journal of Medicinal Chemistry, (Mar. 10, 2005), vol. 48, No. 5, pp. 1344-1358.
Johnson et al., "Induction of Immunogenicity of Monoclonal Antibodies by Conjugation with Drugs," Cancer Research, (Oct. 15, 1991), vol. 15, No. 20, pp. 5774-5776.
Jones et al., "Conjugates of Double-Stranded Oligonucleotides with Poly(ethylene glycol) and Keyhole Limpet Hemocyanin: A Model for Treating Systemic Lupus Erythematosus," Bioconjugate Chemistry, (Sep.-Oct. 1994), vol. 5, No. 5, pp. 390-399.
Jones et al., "Multivalent Thioether-Peptide Conjugates: B Cell Tolerance of an Anti-Peptide Immune Response," Bioconjugate Chemistry, (May-Jun. 1999), vol. 10, No. 3, pp. 480-488.
Jones et al., "Synthesis of LJP 993, a Multivalent Conjugate of the N-Terminal Domain of β2GPI and Suppression of an Anti-β2GPI Immune Response," Bioconjugate Chemistry, (Nov.-Dec. 2001), vol. 12, No. 6, pp. 1012-1020.
Kashef et al., "Synthesis and Characterization of Pseudomonas Aeruginosa Alginate-Tetanus Toxoid Conjugate," Journal of Medical Microbiology, (Oct. 2006), vol. 55, Pt. 10, pp. 1441-1446.
Kellogg et al., "Disulfide-Linked Antibody-Maytansinoid Conjugates: Optimization of In Vivo Activity by Varying the Steric Hindrance at Carbon Atoms Adjacent to the Disulfide Linkage," Bioconjugate Chemistry, (Apr. 20, 2011), vol. 22, No. 4, pp. 717-727.
Kelly et al., "An Antibody-Cytotoxic Conjugate, BIIB015, is a new Targeted Therapy for Cripto Positive Tumours," European Journal of Cancer, (Jul. 2011), vol. 47, No. 11, pp. 1736-1746.
Kim et al., "C-2 Modified Taxol Analogs with Improved Aqueous Solubility," Bulletin of the Korean Chemical Society, (1999), vol. 20, No. 12, pp. 1389-1390.
King et al., "Monoclonal Antibody Conjugates of Doxorubicin Prepared with Branched Linkers: A Novel Method for Increasing the Potency of Doxorubicin Immunoconjugates," Bioconjugate Chemistry, (Mar.-Apr. 1999), vol. 10, No. 2, pp. 279-288.
King et al., "Monoclonal Antibody Conjugates of Doxorubicin Prepared with Branched Peptide Linkers: Inhibition of Aggregation by Methoxytriethyleneglycol Chains," Journal of Medicinal Chemistry, (2002), vol. 45, No. 19, pp. 4336-4343.
Klussman et al., "Secondary mAb-vcMMAE Conjugates Are Highly Sensitive Reporters of Antibody Internalization via the Lysosome Pathway," Bioconjugate Chemistry, (2004), vol. 15, No. 4, pp. 765-773.
Kovar et al., "Star Structure of Antibody-Targeted HPMA Copolymer-Bound Doxorubicin: A Novel Type of Polymeric Conjugate for Targeted Drug Delivery with Potent Antitumor Effect," Bioconjugate Chemistry, (2002), vol. 13, No. 2, pp. 206-215.
Kratz et al., "Preparation, Characterization and in Vitro Efficacy of Albumin Conjugates of Doxorubicin," Biological & Pharmaceutical Bulletin, (1998), vol. 21, No. 1, pp. 56-61.
Kratz et al., "Probing the Cysteine-34 Position of Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound," Journal of Medicinal Chemistry, (2002), vol. 45, No. 25, pp. 5523-5533.

Kubicek et al., "The Tubulin-Bound Structure of the Antimitotic Drug Tubulysin," Angewandte Chemie International Edition, (2010), vol. 49, Issue. 28, pp. 4809-4812.
Kumaresan et al., "Development of Tissue Plasminogen Activator Specific "On Demand Cleavable" (ODC) Linkers or Radioimmunotherapy by Screening One-Bead-One-Compound Combinatorial Peptide Libraries," Bioconjugate Chemistry, (2007), vol. 18, No. 1, pp. 175-182.
Kumaresan et al., Evaluation of Ketone-Oxime Method for Developing Therapeutic On-Demand Cleavable Immunoconjugates, Bioconjugate Chemistry, (2008), vol. 19, No. 6, pp. 1313-1318.
Laguzza et al., "New Antitumor Monoclonal Antibody-Vinca Conjugates LY203725 and Related Compounds: Design, Preparation, and Representative in Vivo Activity," Journal of Medicinal Chemistry, (1989), vol. 32, No. 3, pp. 548-555.
Lau et al., "Novel Doxorubicin-Monoclonal Anti-carcinoembryonic Antigen Antibody Immunoconjugate Activity in Vitro," Bioorganic & Medicinal Chemistry, (1995), vol. 3, No. 10, pp. 1305-1312.
Lee et al., "Prolonged Circulating Lives of Single-Chain Fv Proteins Conjugated with Polyethylene Glycol: A Comparison of Conjugation Chemistries and Compounds," Bioconjugate Chemistry, (1999), vol. 10, No. 6, pp. 973-981.
Lei et al., "Binding of Monoclonal Antibodies against the Carboxyl Terminal Segment of the Nicotinic Receptor δ Subunit Suggests an Unusual Transmembrane Disposition of This Sequence Region," Biochemistry, (1995), vol. 34, No. 20, pp. 6675-6688.
Li et al., "Reduction of Kidney Uptake in Radiometal Labeled Peptide Linkers Conjugated to Recombinant Antibody Fragments. Site-Specific Conjugation of DOTA-Peptides to a Cys-Diabody," Bioconjugate Chemistry, (2002), vol. 13, No. 5, pp. 985-995.
Li et al., "Human Antibodies for Immunotherapy Development Generated via a Human B Cell Hybridoma Technology," PNAS, (Mar. 7, 2006), vol. 103, No. 10, pp. 3557-3562.
Liong et al., "Multifunctional Inorganic Nanoparticles for Imaging, Targeting, and Drug Delivery," ACS Nano, (2008), vol. 2, No. 5, pp. 889-896.
Lipinski et al., "A structurally Diversified Linker Enhances the Immune Response to a Small Carbohydrate Hapten," Glycoconjugate Journal, (2011), vol. 28, No. 3-4, pp. 149-164.
Little et al., "Surface Display of Antibodies," Biotechnology Advances, (1994), vol. 12, Issue 3, pp. 539-555.
Liu et al., "Engineering Therapeutic Monoclonal Antibodies," Immunological Reviews, (2008), vol. 222, No. 1, pp. 9-27.
Liu et al., "Targeting Cell Surface Alpha(v)beta(3) Integrin Increases Therapeutic Efficacies of a Legumain Protease-Activated Auristatin Prodrug," Molecular Pharmaceutics, (Oct. 2011), vol. 9, No. 1, pp. 168-175.
Medarova et al., "In vivo Imaging of siRNA Delivery and Silencing in Tumors," Nature Medicine, (Mar. 2007), vol. 13, No. 3, pp. 372-377.
Medina et al., "Targeted Liposomal Drug Delivery in Cancer," Current Pharmaceutical Design, (2004), vol. 10, No. 24, pp. 2981-2989.
Meyer-Losic et al., "Improved Therapeutic Efficacy of Doxorubicin through Conjugation with a Novel Peptide Drug Delivery Technology (Vectocell)," Journal of Medicinal Chemistry, (2006), vol. 49, No. 23, pp. 6908-6916.
Mikolajczyk et al., "High Yield, Site-Specific Coupling of N-Terminally Modified β-Lactamase to a Proteolytically Derived Single-Sulfhydryl Murine Fab'," Bioconjugate Chemistry, (1994), vol. 5, No. 6, pp. 636-646.
Miller et al., "Design, Construction, and In Vitro Analyses of Multivalent Antibodies," The Journal of Immunology, (2003), vol. 170, No. 9, pp. 4854-4861.
Miller et al., "Synthesis of Taxoids with Improved Cytotoxicity and Solubility for Use in Tumor-Specific Delivery," Journal of Medicinal Chemistry, (2004), vol. 47, No. 20, pp. 4802-4805.
Mitchell et al., "Direct Ring Conjugation of Catecholamines and Their Immunological Interactions," Bioconjugate Chemistry, (2007), vol. 18, No. 1, pp. 268-274.
Mohammad et al., "A new Tubulin Polymerization Inhibitor, Auristatin PE, Induces Tumor Regression in a Human Waldenstrom's

(56) References Cited

OTHER PUBLICATIONS

Macroglobulinemia Xenograft Model," International Journal of Oncology, (1999), vol. 15, No. 2, pp. 367-372.

Moon et al., "Antibody Conjugates of 7-Ethyl-10-hydroxycamptothecin (SN-38) for Targeted Cancer Chemotherapy," Journal of Medicinal Chemistry, (2008), vol. 51, No. 21, pp. 6916-6926.

Nicolaou et al., "Calicheamicin θ1 I: A Rationally Designed Molecule with Extremely Potent and Selective DNA Cleaving Properties and Apoptosis Inducing Activity," Angewandte Chemie (International Edition in English), (1994), vol. 33, No. 2, pp. 183-186.

Nicolaou et al., "Chemical Synthesis and Biological Evaluation of C-2 Taxoids," Journal of the American Chemical Society, (1995), vol. 117, No. 9, pp. 2409-2420.

Niman et al., "Generation of Protein-Reactive Antibodies by Short Peptides is an Event of High Frequency: Implications for the Structural Basis of Immune Recognition," Proceedings of the National Academy of Sciences, (Aug. 1983), vol. 80, No. 16, pp. 4949-4953.

Ojima et al., "Syntheses and Structure-Activity Relationships of the Second-Generation Antitumor Taxoids: Exceptional Activity against Drug-Resistant Cancer Cells," Journal of Medicinal Chemistry, (1996), vol. 39, No. 20, pp. 3889-3896.

Ojima et al., "Syntheses and Structure-Activity Relationships of Taxoids Derived from 14β-Hydroxy-10-deacetylbaccatin III," Journal of Medicinal Chemistry, (1997), vol. 40, No. 3, pp. 267-278.

Ojima et al., "A Common Pharmacophore for Cytotoxic Natural Products that Stabilize Microtubules," Proceedings of be National Academy of Sciences, (Apr. 1999), vol. 96, No. 8, pp. 4256-4261.

Ojima et al., "Tumor-Specific Novel Taxoid-Monoclonal Antibody Conjugates," Journal of Medicinal Chemistry, (2002), vol. 45, No. 26, pp. 5620-5623.

Pando et al., "First Total Synthesis of Tubulysin B," Organic Letters, (2009), vol. 11, No. 24, pp. 5567-5569.

Pando et al., "The Multiple Multicomponent Approach to Natural Product Mimics: Tubugis, N-Substituted Anticancer Peptides with Picomolar Activity," Journal of the American Chemical Society, (2011), vol. 133, No. 20, pp. 7692-7695.

Parham, "On the Fragmentation of Monoclonal IgG1, IgG2a, and IgG2b from BALB/c mice," The Journal of Immunology, (Dec. 1983), vol. 131, No. 6, pp. 2895-2902.

Patterson et al., "Expedient Synthesis of N-Methyl Tubulysin Analogues with High Cytotoxicity," The Journal of Organic Chemistry, (2008), vol. 73, No. 12, pp. 4362-4369.

Peltier et al., "The Total Synthesis of Tubulysin D," Journal of the American Chemical Society, (2006), vol. 128, No. 50, pp. 16018-16019.

Raghavan et al., "Cytotoxic Simplified Tubulysin Analogues," Journal of Medicinal Chemistry, (2008), vol. 51, No. 6, pp. 1530-1533.

Ruppert et al., "Chemical Coupling of a Monoclonal Antisurfactant Protein-B Antibody to Human Urokinase for Targeting Surfactant-Incorporating Alveolar Fibrin," Bioconjugate Chemistry, (2002), vol. 13, No. 4, pp. 804-811.

Safavy et al., "Synthesis and Biological Evaluation of Paclitaxel-C225 Conjugate as a Model for Targeted Drug Delivery," Bioconjugate Chemistry, (2003), vol. 14, No. 2, pp. 302-310.

Safavy et al., "Site-Specifically Traced Drug Release and Biodistribution of a Paclitaxel-Antibody Conjugate toward Improvement of the Linker Structure," Bioconjugate Chemistry, (2004), vol. 15, No. 6, pp. 1264-1274.

Sani et al., "Total Synthesis of Tubulysins U and V," Angewandte Chemie International Edition, (2007), vol. 46, No. 19, pp. 3526-3529.

Scott, Jr., "An Immunotoxin Composed of a Monoclonal Antitransferrin Receptor Antibody Linked by a Disulfide Bond to the Ribosome-Inactivating Protein Gelonin: Potent In Vitro and In Vivo Effects Against Human Tumors," Journal of the National Cancer Institute, (Nov. 1987), vol. 79, No. 5, pp. 1163-1172.

Scott et al., "Synthesis of Reagents for the One Step Incorporation of Hydrazide Functionality onto the Lysine Residues of Proteins, and their use as Linkers for Carbonyl Containing Molecules," Bioorganic & Medicinal Chemistry Letters, (1996), vol. 6, No. 13, pp. 1491-1496.

Scott et al., "Aiming for the heart: Targeted Delivery of Drugs to Diseased Cardiac Tissue," Expert Opinion on Drug Delivery, (2008), vol. 5, No. 4, pp. 459-470.

Senter et al., "Novel Photocleavable Protein Crosslinking Reagents and their use in the Preparation of Antibody-Toxin Conjugates," Photochemistry and Photobiology, (1985), vol. 42, No. 3, pp. 231-237.

Sharkey et al., "Epratuzumab-SN-38: A New Antibody-Drug Conjugate for the Therapy of Hematologic Malignancies," Molecular Cancer Therapeutics, (Jan. 2012), vol. 11, No. 1, pp. 224-234.

Siiman et al., "Tris(3-mercaptopropyl)-N-glycylaminomethane as a New Linker to Bridge Antibody with Metal Particles for Biological Cell Separations," Bioconjugate Chemistry, (2000), vol. 11, No. 4, pp. 549-556.

Skwarczynski et al., "Paclitaxel Prodrugs: Toward Smarter Delivery of Anticancer Agents," Journal of Medicinal chemistry, (Dec. 14, 2006), vol. 49, No. 25, pp. 7253-7269.

Smith et al., "The Enediyne Antibiotics," Journal of Medicinal Chemistry, (May 24, 1996), vol. 39, No. 11, pp. 2103-2117.

Srinivasachar et al., "New Protein Cross-Linking Reagents that are Cleaved by Mild Acid," Biochemistry, (1989), vol. 28, No. 6, pp. 2501-2509.

Studer et al., "Influence of a Peptide Linker on Biodistribution and Metabolism of Antibody-Conjugated Benzyl-EDTA. Comparison of Enzymatic Digestion in Vitro and in Vivo," Bioconjugate Chemistry, (1992), vol. 3, No. 5, pp. 424-429.

Suzawa et al., "Synthesis of a Novel Duocarmycin Derivative DU-257 and its Application to Immunoconjugate Using Poly(ethylene glycol)-dipeptidyl Linker Capable of Tumor Specific Activation," Bioorganic & Medicinal Chemistry, (2000), vol. 8, No. 8, pp. 2175-2184.

Szardenings, "Phage Display of Random Peptide Libraries: Applications, Limits, and Potential," Journal of Receptors and Signal Transduction, (2003), vol. 23, No. 4, pp. 307-349.

Tadayoni et al., "Synthesis, in Vitro Kinetics, and in Vivo Studies on Protein Conjugates of AZT: Evaluation as a Transport System to Increase Brain Delivery," Bioconjugate Chemistry, (1993), vol. 4, No. 2, pp. 139-145.

Ten Hoeve et al., "Syntheses of Haptens Containing Dioxaphosphorinan Methoxyacetic Acid Linker Arms for the Production of Antibodies to Organophosphate Pesticides," Bioconjugate Chemistry, (May/Jun. 1997), vol. 8, No. 3, pp. 257-266.

Trail et al., "Effect of Linker Variation on the Stability, Potency, and Efficacy of Carcinoma-reactive BR64-Doxorubicin Immunoconjugates," Cancer Research, (Jan. 1, 1997), vol. 57, No. 1, pp. 100-105.

Trouet et al., "A Covalent Linkage between Daunorubicin and Proteins that is Stable in Serum and Reversible by Lysosomal Hydrolases, as Required for a Lysosomotropic Drug-Carrier Conjugate: In Vitro and In Vivo Studies," Proceedings of the National Academy of Sciences, (Jan. 1982), vol. 79, No. 2, pp. 626-629.

Tsai et al., "Sensitive Measurement of Polyethylene Glycol-Modified Proteins," BioTechniques, (Feb. 2001), vol. 30, No. 2, pp. 396-402.

Ullrich et al., "Pretubulysin, a Potent and Chemically Accessible Tubulysin Precursor from Angiococcus disciformis," Angewandte Chemie International Edition, (2009), vol. 48, No. 24, pp. 4422-4425.

Walker et al., "Monoclonal Antibody Mediated Intracellular Targeting of Tallysomycin S10b," Bioorganic & Medicinal Chemistry Letters, (Aug. 16, 2004), vol. 14, No. 16, pp. 4323-4327.

Warpehoski et al., "Stereoelectronic Factors Influencing the Biological Activity and DNA Interaction of Synthetic Antitumor Agents Modeled on CC-1065," Journal of Medicinal Chemistry, (1988), vol. 31, No. 3, pp. 590-603.

Watanabe et al., "Measurement of Cross-Reactive Properties of Adriamycin Derivatives by the Inhibition Enzyme-Linked Immunosorbent Assay for Adriamycin," Tokai Journal of Experimental and Clinical Medicine, (1990), vol. 15, No. 4, pp. 327-334.

(56) References Cited

OTHER PUBLICATIONS

Widdison et al., "Semisynthetic Maytansine Analogues for the Targeted Treatment of Cancer," Journal of Medicinal Chemistry, (2006), vol. 49, No. 14, pp. 4392-4408.
Wilbur et al., "Reagents for Astatination of Biomolecules. 5. Evaluation of Hydrazone Linkers in 211 At- and 125I-Labeled closo-Decaborate(2-) Conjugates of Fab' as a Means of Decreasing Kidney Retention," Bioconjugate Chemistry, (2011), vol. 22, No. 6, pp. 1089-1102.
Wipf et al., "Synthesis of the Tubuvaline-Tubuphenylalanine (Tuv-Tup) Fragment of Tubulysin," Organic Letters, (2004), vol. 6, No. 22, pp. 4057-4060.
Wipf et al., "Total Synthesis of N14-Desacetoxytubulysin H," Organic Letters, (2007), vol. 9, No. 8, pp. 1605-1607.
Zhao et al., "Synthesis and Evaluation of Hydrophilic Linkers for Antibody-Maytansinoid Conjugates," Journal of Medicinal Chemistry, (2011), vol. 54, No. 10, pp. 3606-3623.
Zhao et al., "Synthesis and Biological Evaluation of Antibody Conjugates of Phosphate Prodrugs of Cytotoxic DNA Alkylators for the Targeted Treatment of Cancer," Journal of Medicinal Chemistry, (2012), vol. 55 No. 2, pp. 766-782.
Zhou et al., "Cell-Specific Delivery of a Chemotherapeutic to Lung Cancer Cells," Journal of the American Chemical Society, (2004), vol. 126, No. 48, pp. 15656-15657.
International Search Report (From PCT/ISA/210) and the Written Opinion of the International Searching Authority (From PCT/ISA/237) dated Dec. 8, 2014, by the State Intellectual Property Office, the P.R. China, in corresponding International Application No. PCT/CN2014/072769. (7 pages).
International Preliminary Report on Patentability (Form PCT/IB/373) dated Sep. 6, 2016, by the International Bureau of WIPO, in corresponding International Application No. PCT/CN2014/072769. (1 page).
Office Action (Notice of grant for your patent) dated Feb. 16, 2017, by the Australian Patent Office in corresponding Australian Patent Application No. 2014384434. (1 page).
Office Action dated Feb. 25, 2019. by the U.S. Patent and Trademark Office in related U.S. Appl. No. 15/118,726. (11 pages).
Office Action dated Nov. 1, 2018, by the U.S. Patent and Trademark Office in related U.S. Appl. No. 15/118,726. (9 pages).
Office Action dated Jun. 15, 2018, by the U.S. Patent and Trademark Office in related U.S. Appl No 15/118,726. (7 pages).
Office Action dated Mar. 27, 2018, by the U.S. Patent and Trademark Office in related U.S. Appl. No. 15/118,726. (11 pages).
IUPAC. Compendium of Chemical Terminology, 2nd ed. "Azides" (the "Gold Book") (1997) (Downloaded from http://goldbook.iupac.org/plain/A00555-plain.html) (Year 1997) (1 page).
IUPAC. Compendium of Chemical Terminology, 2nd ed. "Ketones" (the "Gold Book") (1997) (Downloaded from http://goldbook.iupac.org/html/K/K03386.html on Feb. 17, 2019) (1997) (1 page).
Compound CAS Registry No. 371233-32-8 (2001) (Year 2001) (1 page).
Third Office Action dated Nov. 18, 2018, by the State Intellectual Property Office of the People's Republic of China in corresponding Chinese Patent Application No. 201480076320.3 and an English translation of the Office Action. (10 pages).
Adams et al., "Generating Improved Single-Chain Fv Molecules for Tumor Targeting," Journal of Immunological Methods, (Dec. 10, 1999), vol. 231, Issue 1-2, pp. 249-260.
Afar et al., "Preclinical Validation of Anti-TMEFF2-Auristatin E-Conjugated Antibodies in the Treatment of Prostate Cancer," Molecular Cancer Therapeutics, (Aug. 2004), vol. 3, No. 8, pp. 921-931.
Albrecht et al., "Monospecific Bivalent scFv-SH: Effects of Linker Length and Location of an Engineered Cysteine on Production, Antigen Binding Activity and Free SH Accessiblity," Journal of Immunological Methods, (Mar. 20, 2006), vol. 310, Issue 1-2, pp. 100-116.
Alley et al., "Antibody-Drug Conjugates: Targeted Drug Delivery for Cancer," Current Opinion in Chemical Biology, (Aug. 2010), vol. 14, Issue 4, pp. 529-537.
Almagro et al., "Humanization of Antibodies," Frontiers in Bioscience, (Jan. 1, 2008), vol. 13, pp. 1619-1633.
Almutairi et al., "Biodegradable Dendritic Positron-Emitting Nanoprobes for the Noninvasive Imaging of Angiogenesis," PNAS, (Jan. 20, 2009), vol. 106, No. 3, pp. 685-690.
Anderson et al., "Enhanced in Vitro Tumor Cell Retention and Internalization of Antibody Derivatized with Synthetic Peptides," Bioconjugate Chemistry, (Jan. 1993), vol. 4, No. 1, pp. 10-18.
Antczak et al., "Influence of the Linker on the Biodistribution and Catabolism of Actinium-225 Self-Immolative Tumor-Targeted Isotope Generators," Bioconjugate Chemistry, (Nov.-Dec. 2006), vol. 17, No. 6, pp. 1551-1560.
Aoki et al., "Design and Synthesis of a Photocleavable Biotin-Linker for the Photoisolation of Ligand-Receptor Complexes Based on the Photolysis of 8-Quinolinyl Sulfonates in Aqueous Solution," Bioorganic & Medicinal Chemistry, (May 1, 2009), vol. 17, Issue 9, pp. 3405-3413.
Arpicco et al., "New Coupling Reagents for the Preparation of Disulfide Cross-Linked Conjugates with Increased Stability," Bioconjugate Chemistry, (May-Jun. 1997), vol. 8, No. 3, pp. 327-337.
Austin et al. "Oxidizing Potential of Endosomes and Lysosomes Limits Intracellular Cleavage of Disulfide-Based Antiboby-Drug Conjugates," PNAS, (Dec. 13, 2005), vol. 102, No. 50, pp. 17987-17992.
Balasubramanian et al., "Total Synthesis and Biological Evaluation of Tubulysin U, Tubulysin V, and Their Analogues," Journal of Medicinal Chemistry, (Jan. 22, 2009), vol. 52, No. 2, pp. 238-240.
Barbour et al., "Stabilization of Chimeric BR96-Doxorubicin Immunoconjugate," Pharmaceutical Research, (Feb. 1995), vol. 12, No. 2, pp. 215-222.
Beeson et al., "Conditionally Cleavable Radioimmunoconjugates: A Novel Approach for the Release of Radioisotopes from Radioimmunoconjugates," Bioconjugate Chemistry, (Sep.-Oct. 2003), vol. 14, No. 5, pp. 927-933.
Bickel et al., "In Vivo Cleavability of a Disulfide-Based Chimeric Opioid Peptide in Rat Brain," Bioconjugate Chemistry, (Mar.-Apr. 1995), vol. 6, No. 2, pp. 211-218.
Boger et al., "Parallel Synthesis and Evaluation of 132 (+)-1,2,9,9a-Tetrahydrocyclopropa[c]benz[e]indol-4-one (CBI) Analogues of CC-1065 and the Duocarmycins Defining the Contribution of the DNA-Binding Domain," The Journal of Organic Chemistry, (Oct. 5, 2001), vol. 66, No. 20, pp. 6654-6661.
Brannigan et al., "Protein Engineering 20 Years On," Nature Reviews Molecular Cell Biology, (Dec. 2002), vol. 3, No. 12, pp. 964-970.
Brich et al., "Preparation and Characterization of a Water Soluble Dextran Immunoconjugate of Doxorubicin and the Monoclonal Antibody (ABL 364)," Journal of Controlled Release, (Mar. 1992), vol. 19, Issues 1-3, pp. 245-257.
Burgess, "The Complex Mediators of Cell Growth and Differentiation," Immunology Today, (Jun. 1984), vol. 5, No. 6, pp. 155-158.
Carlsson et al., "Protein Thiolation and Reversible Protein-Protein Conjugation. N-Succinimidyl 3-(2-pyridyldithio) Propionate, a new Heterobifunctional Reagent," Biochemical Journal, (Oct. 1978), vol. 173, No. 3, pp. 723-737.
Chai et al., "Discovery of 23 Natural Tubulysins from Angiococcus disciformis An d48 and Cystobacter SBCb004," Chemistry & Biology (Mar. 26, 2010), vol. 17, issue 3, pp. 296-309.
Chandrasekhar et al., "Toward Tubulysin: Gram-Scale Synthesis of Tubuvaline-Tubuphenylalanine Fragment," The Journal of Organic Chemistry, (Dec. 18, 2009), vol. 74, No. 24, pp. 9531-9534.
Chen et al., "Antibody-Cytotoxic Agent Conjugates for Cancer Therapy," Expert Opinion on Drug Delivery, (Sep. 2005), vol. 2, No. 5, pp. 873-890.
Chen et al., "Synthesis of Doxorubicin Conjugates Through Hydrazone Bonds to Melanotransferrin P97," Synthetic Communications: An International Journal for Rapid Communication of Synthetic Organic Chemistry, (2003), vol. 33, No. 14, pp. 2377-2390.
Delprino et al., "Toxin-Targeted Design for Anticancer Therapy. I: Synthesis and Biological Evaluation of New Thioimidate

(56) References Cited

OTHER PUBLICATIONS

Heterobifunctional Reagents," Journal of Pharmaceutical Sciences, (May 1993), vol. 82, No. 5, pp. 506-512.

Dente et al., "Monoclonal Antibodies that Recognise Filamentous Phage: Tools for Phage Display Technology," Gene, (Oct. 11, 1994), vol. 148, Issue 1, pp. 7-13.

Dhar et al., "Targeted Delivery of Cisplatin to Prostate Cancer Cells by Aptamer Functionalized Pt(IV) Prodrug-PLGA-PEG Nanoparticles," PNAS, (Nov. 11, 2008), vol. 105, No. 45, pp. 17356-17361.

Dijoseph et al., "Antibody-Targeted Chemotherapy with CMC-544: a CD22-Targeted Immunoconjugate of Calicheamicin for the Treatment of B-Lymphoid Malignancies," Blood, (Mar. 1, 2004), vol. 103, No. 5, pp. 1807-1814.

Domling et al., "Total Synthesis of Tubulysin U and V," Angew Chem Int Ed Engl., (Nov. 6, 2006), vol. 45, No. 43, pp. 7235-7239.

Doronina et al., "Enhanced Activity of Monomethylauristatin F through Monoclonal Antibody Delivery: Effects of Linker Technology on Efficacy and Toxicity," Bioconjugate Chemistry, (Jan.-Feb. 2006), vol. 17, No. 1, pp. 114-124.

Doronina et al., "Novel Peptide Linkers for Highly Potent Antibody-Auristatin Conjugate," Bioconjugate Chemistry, (Oct. 2008), vol. 19, No. 10, pp. 1960-1963.

Dulbecco et al., "A Plaque Assay for the Polyoma Virus," Letters to the Editors, (1959), Virol. 8, pp. 396-397.

Ebner et al., "A New, Simple Method for Linking of Antibodies to Atomic Force Microscopy Tips," Bioconjugate Chemistry, (Jul.-Aug. 2007), vol. 18, No. 4, pp. 1176-1184.

Erickson et al., "Tumor Delivery and In Vivo Processing of Disulfide-Linked and Thioether-Linked Antibody-Maytansinoid Conjugates," Bioconjugate Chemistry, (Jan. 2010), vol. 21, No. 1, pp. 84-92.

Flenniken et al., "A Library of Protein Cage Architectures as Nanomaterials," Viruses and Nanotechnology, (2009), vol. 327 of the series Current Topics in Microbiology and Immunology, pp. 71-93.

Frankel et al., "Cell Surface Receptor-Targeted Therapy of Acute Myeloid Leukemia: A Review," Cancer Biotherapy & Radiopharmaceuticals, (Oct. 2000), vol. 15, No. 5, pp. 459-476.

Friestad et al., "Stereoselective Mn-Mediated Coupling of Functionalized Iodides and Hydrazones: A Synthetic Entry to the Tubulysin γ-Amino Acids," Organic Letters, (Sep. 2004), vol. 6, No. 19, pp. 3249-3252.

Friestad et al., "Synthesis of γ-Amino Esters via Mn-Mediated Radical Addition to Chiral γ-Hydrazonoesters," Organic Letters, (2009), vol. 11, No. 5, pp. 1095-1098.

Garsky et al., "The Synthesis of a Prodrug of Doxorubicin Designed to Provide Reduced Systemic Toxicity and Greater Target Efficacy," Journal of Medicinal Chemistry, (Nov. 22, 2001), vol. 44, No. 24, pp. 4216-4224.

Geysen et al., "Small Peptides Induce Antibodies with a Sequence and Structural Requirement for Binding Antigen Comparable to Antibodies Raised Against the Native Protein," PNAS, (Jan. 1985), vol. 82, No. 1, pp. 178-182.

Goff et al., "Substituted 2-Iminothiolanes: Reagents for the Preparation of Disulfide Cross-Linked Conjugates with Increased Stability," Bioconjugate Chemistry, (Nov.-Dec. 1990), vol. 1, No. 6, pp. 381-386.

Greenwald et al., "Drug Delivery Systems Employing 1,4- or 1,6-Elimination: Poly(ethylene glycol) Prodrugs of Amine-Containing Compounds," Journal of Medicinal Chemistry, (Sep. 9, 1999), vol. 42, No. 18, pp. 3657-3667.

Haenseler et al., "Activation of Methotrexate-α-Alanine by Carboxypeptidase A-Monoclonal Antibody Conjugate," Biochemistry, (Jan. 28, 1992), vol. 31, No. 3, pp. 891-897.

Hamann et al., "An Anti-CD33 Antibody-Calicheamicin Conjugate for Treatment of Acute Myeloid Leukemia. Choice of Linker," Bioconjugate Chemistry, (Jan.-Feb. 2002), vol. 13, No. 1, pp. 40-46.

Hamann et al., "An Anti-MUC1 Antibody-Calicheamicin Conjugate for Treatment of Solid Tumors. Choice of Linker and Overcoming Drug Resistance," Bioconjugate Chemistry, (Mar.-Apr. 2005), vol. 16, No. 2, pp. 346-353.

Hamann et al., "A Calicheamicin Conjugate with a Fully Humanized Anti-MUC1 Antibody Shows Potent Antitumor Effects in Breast and Ovarian Tumor Xenografts," Bioconjugate Chemistry, (Mar.-Apr. 2005), vol. 16, No. 2, pp. 354-360.

Hinman et al., "Preparation and Characterization of Monoclonal Antibody Conjugates of the Calicheamicins: A Novel and Potent Family of Antitumor Antibiotics," Cancer Research, (Jul. 15, 1993), vol. 53, No. 14, pp. 3336-3342.

Houdebine, "Antibody Manufacture in Transgenic Animals and Comparisons with other Systems," Current Opinion in Biotechnology, (Dec. 1, 2002), vol. 13, Issue 6, pp. 625-629.

Huse et al., "Generation of a Large Combinatorial Library of the Immunoglobulin Repertoire in Phage Lambda," Science, (Dec. 8, 1989), vol. 246, No. 4935, pp. 1275-1281. Only Have p. 1275.

Javier et al., "Aptamer-Targeted Gold Nanoparticles as Molecular-Specific Contrast Agents for Reflectance Imaging," Bioconjugate Chemistry, (Jun. 2008), vol. 19, No. 6, pp. 1309-1312.

Abstract of Chelliah et al., "A Virtual Screening Hit Reveals New Possibilities for Developing Group III Metabotropic Glutamate Receptor Agonists," Journal of Medicinal Chemistry, (Apr. 8, 2010), vol. 53, No. 7, pp. 2797-2813. (1 page).

Abstract of Govindan, S. V. et al., "Designing immunoconjugates for cancer therapy," Expert Opinion on Biological, (Jul. 1, 2012), vol. 12, No. 7, pp. 873-890. (1 page).

Summary of Rozhko, L.F. et al., "Method for synthesis of phosphinic acids from hypophosphites V. The synthesis of pseudo-α,α-dipeptides," Amino Acids, (Aug. 2005), vol. 29, No. 2, pp. 139-143. (1 page).

Office Action dated Apr. 12, 2017, by the State Intellectual Property Office of People's Republic of China in corresponding Chinese Patent Application No. 201480076320.3 and an English Translation of the Office Action. (9 pages).

Search Report dated Nov. 28, 2017, by the State Intellectual Property Office of People's Republic of China in corresponding Chinese Patent Application No. 201480076320.3. (1 page).

Partial Supplemental European search report dated Sep. 22, 2017, by the European Patent Office in corresponding European Patent Application No. 14883832.9. (12 pages).

The extended European search report dated Jan. 9, 2018, by the European Patent Office in corresponding European Patent Application No. 14883832.9. (24 pages).

Office Action (Notification of Reasons for Refusal) dated Jul. 18, 2017, by the Japanese Patent Office in corresponding Japanese Patent Application No. 2016-554198 and an English Translation of the Office Action. (7 pages).

Office Action (Notification of Reasons for Refusal) dated Dec. 21, 2017, by the Japanese Patent Office in corresponding Japanese Patent Application No. 2016-554198 and an English Translation of the Office Action. (9 pages).

Office Action dated May 6, 2018 by the State Intellectual Property Office of People's Republic of China in corresponding Chinese Patent Application No. 201480076320.3 and an English translation of the Office Action. (10 pages).

M. Borloo et al., 9 Synthesis, 1074-1076 (1995).

V. Kubíček et al., 20 Dalton Transactions, 3927-3938 (2003).

CAS Abstract of M. Borloo et al., 9 Synthesis, 1074-1076 (1995).

CAS Abstract Di Sabato, J Am Chem Soc (1961).

G. Di Sabato et al., 83 Journal of the American Chemical Society, 4400-4405 (1961).

S. L. Shames et al., 83 Journal of the American Chemical Society, 6177-6184 (1981).

C-H Lin et al., 4 Chemistry & Biology, 859-866 (1997).

Notification of Reasons for Refusal dated Aug. 15, 2018 by the Japanese Patent Office in corresponding Japanese Patent Application No. 2016-554198 and an English translation of the Notification. (5 pages).

Decision to Grant dated Sep. 6, 2018 by the Japanese Patent Office in corresponding Japanese Patent Application No. 2016-554198 and an English translation of the Decision. (5 pages).

Office Action dated May 9, 2019, by the U.S. Patent and Trademark Office in related U.S. Appl. No. 15/118,726. (11 pages).

(56) References Cited

OTHER PUBLICATIONS

Caldwell et al., "Phosphinic Acid Inhibitors of Matrix Metalloproteinases," Bioorganic & Medicinal Chemistry Letters, (1996), vol. 6, No. 3, pp. 323-328.
Goulet et al., "Inhibition of Stromelysin-1 (MMP-3) by Peptidyl Phosphinic Acids," Bioorganic & Medicinal Chemistry Letters, (1994), vol. 4, No. 10, pp. 1221-1224.
Notice of Allowance dated Aug. 14, 2019, by the U.S. Patent and Trademark Office in related U.S. Appl. No. 15/118,726. (13 pages).
Office Action dated Jun. 26, 2019, by the U.S. Patent and Trademark Office in related U.S. Appl. No. 16/228,310. (15 pages).
Office Action dated Jun. 26, 2019, by the U.S. Patent and Trademark Office in related U.S. Appl. No. 16/228,437. (16 pages).
Office Action dated Sep. 25, 2017, by the Canadian Patent Office in corresponding Canadian Application No. 2,938,919. (7 pages).
Office Action dated Jun. 15, 2018, by the Canadian Patent Office in corresponding Canadian Application No. 2,938,919. (4 pages).
Office Action dated Apr. 5, 2019, by the Canadian Patent Office in corresponding Canadian Application No. 2,938,919. (4 pages).
Office Action dated Nov. 26, 2019, by the U.S. Patent and Trademark Office in related U.S. Appl. No. 16/228,310. (16 pages).
Office Action dated Nov. 26, 2019, by the U.S. Patent and Trademark Office in related U.S. Appl. No. 16/228,437. (11 pages).
Notice of Allowance dated Apr. 9, 2020, by the U.S. Patent and Trademark Office in related U.S. Appl. No. 16/228,310. (15 pages).
Notice of Allowance dated Apr. 9, 2020, by the U.S. Patent and Trademark Office in related U.S. Appl. No. 16/228,437. (15 pages).

\* cited by examiner (antiCD22-TZ041).

CHARGED LINKERS AND THEIR USES FOR CONJUGATION

CROSS REFERENCE TO RELATED APPLICATIONS

This application is a division of U.S. application Ser. No. 15/118,726, filed on Aug. 12, 2016, entitled "CHARGED LINKERS AND THEIR USES FOR CONJUGATION," which in turn is a national stage of PCT/CN2014/072769, filed on Feb. 28, 2014. The entire content of each of the prior applications is hereby incorporated by reference.

FIELD OF THE INVENTION

The present invention relates to the preparation of novel charged phosphinate linkers used for the conjugation of a drug, in particular, a cytotoxic agent to a biological molecule. The present invention also relates to methods of making cell-binding agent-drug (cytotoxic agent) conjugates comprising either modification of drugs with these charged linkers first, followed by reaction with cell-binding agents; or modification of cell-binding agents with these charged linkers first, followed by reaction with drugs.

BACKGROUND OF THE INVENTION

Targeted drug delivery (Muller, R; Keck, C (2004). *J. Biotech.* 113, 151) whose objective is to prolong, localize, target and have a protected drug interaction with the diseased tissue has been extensively studied during the past three decades. There are different types of drug delivery vehicles, such as, antibodies, proteins, vitamins, peptides, polymeric micelles, liposomes, lipoprotein-based drug carriers, nano-particle drug carriers, dendrimers etc. An ideal drug delivery vehicle must be non-toxic, biocompatible, non-immunogenic, and biodegradable (Scott, R; Crabbe, D; et al (2008) *Expert Opin. Drug Deli.* 5, 459) and avoid recognition by the host's defense mechanisms (Saltzman, W.; Torchilin, V. (2008). "Drug delivery systems" *Access Science*. McGraw-Hill Co.). The link between the delivery vehicles, in particular, antibodies and the cell-killing agent plays a critical role in the development of targeted drug delivery systems, as the nature of the linker significantly affects the potency, selectivity and the pharmacokinetics of the resulting conjugates (Zhao, R.; Wilhelm, S. et al, (2011) *J. Med. Chem.* 36, 5404; Doronina, S.; Mendelsohn, B.; et al, (2006) *Bioconjug Chem*, 17, 114; Hamann, P.; Hinman, L; et al. (2005) *Bioconjug Chem.* 16, 346). Four types of linkers had been used for preparation of cell binding agent-drug conjugates that have entered the clinic: (a) acid-labile linkers, exploiting the acidic endosomal and lysosomal intracellular microenvironment; (b) linkers cleavable by lysosomal proteases; (c) chemically stable thioether linkers that release a lysyl adduct after proteolytic degradation of the antibody inside the cell; and (d) disulfide-containing linkers, which are cleaved upon exposure to an intracellular thiol ((Zhao, R.; Wilhelm, S. et al, (2011) *J. Med. Chem.* 36, 5404).

Conjugates of cell-binding agents with drugs or modified chemical compounds via different types of linkers have been described (U.S. Pat. Nos. 4,680,338, 5,122,368, 5,141,648, 5,208,020, 5,416,064; 5,475,092, 5,543,390, 5,563,250 5,585,499, 5,880,270, 6,214,345, 6,436,931, 6,372,738, 6,340,701, 6,989,452, 7,129,261, 7,375,078, 7,498,302, 7,507,420, 7,691,962, 7,910,594, 7,968,586, 7,989,434, 7,994,135, 7,999,083, 8,153,768, 8,236,319, Zhao, R.; et al, (2011) *J. Med. Chem.* 36, 5404; Doronina, S.; et al, (2006) *Bioconjug Chem,* 17, 114; Hamann, P.; et al. (2005) *Bioconjug Chem.* 16, 346). Typically, in these conjugates, the cell-binding agents are first modified with a bifunctional agent such as SPDP (N-succinimidyl 3-(2-pyridyldithio) propionate), or SMCC (succinimidyl-4-(N-maleimidomethyl)cyclohexane-1-carboxylate); or SPDB (N-succinimidyl 4-(2-pyridyldithio)butanoate); to introduce an active disulfide or a maleimido moiety. Reaction with a thiol-containing cytotoxic drug provides a conjugate in which the cell-binding agent, such as a monoclonal antibody, and drug are linked via disulfide bonds or thioether bonds.

However, the use of the cell binding molecule-drug conjugates, such as antibody-drug conjugates (ADCs), in developing therapies for a wide variety of cancers has been limited both by the availability of specific targeting agents (carriers) as well as the conjugation methodologies which result in the formation of protein aggregates when the amount of the drugs that are conjugated to the carrier (i.e., the drug loading) is increased. Normally the tendency for cytotoxic drug conjugates to aggregate is especially problematic when the conjugation reactions are performed with the hydrophobic linkers. Since higher drug loading increases the inherent potency of the conjugate, it is desirable to have as much drug loaded on the carrier as is consistent with retaining the affinity of the carrier protein. The presence of aggregated protein, which may be nonspecifically toxic and immunogenic, and therefore must be removed for therapeutic applications, makes the scale-up process for the production of these conjugates more difficult and decreases the yield of the products.

Consequently, there is a critical need to improve methods for conjugating drugs/cytotoxic drugs to carriers (cell binding molecules) that minimize the amount of aggregation and thereby allow for as high a drug loading as possible through the application of a charged crosslinker.

SUMMARY OF THE INVENTION

The present invention provides charged linkers containing phosphinate group to link drugs to a cell-binding agent (e.g., an antibody). The preferred formula of the cell binding molecule-charged linker-drug conjugates can be represented as: Cb-(-L-Drug)$_n$, wherein Cb is a cell-binding agent, L is a charged linker, Drug is a drug molecule, and n is an integer from 1 to 20. The advantages in applying the charged linker in the cell molecule-drug conjugate are: a). reducing the aggregation of the conjugates in water based media; b). enabling higher drug-per-cell binding molecule-ratio conjugate, resulting in higher potency; c). being retained inside the target cell after the drug-linker released from the conjugates, which can combat permeability-glycoprotein (Pgp)-expressing multidrug resistant (MDR) cells.

In one aspect of the present invention, the charged linker is represented by formula (I) wherein Y can react with a cell-binding agent and Z can react with a cytotoxic drug:

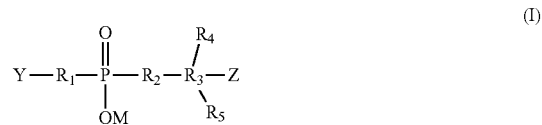

wherein:

Y represents a functional group that enables reaction with a cell-binding agent.

Z represents a functional group that enables linkage of a cytotoxic drug via a disulfide, thioether, thioester, peptide, hydrazone, ether, ester, carbamate, carbonate, amine (secondary, tertiary, or quartary), imine, cycloheteroalkyane, heteroaromatic, alkoxime or amide bond.

$R_1$, $R_2$, $R_3$, $R_4$, and $R_5$, are the same or different and are H, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula $(OCH_2CH_2)_p$, wherein p is an integer from 0 to about 1000, or combination thereof.

Additionally $R_1$, $R_2$, and $R_3$ are respectively a chain of atoms selected from C, N, O, S, Si, and P that covalently connects the cell-surface binding ligand, the phosphinate group, the conjugated drug and among themselves ($R_1$, $R_2$ and $R_3$). The atoms used in forming the hydrophilic charged linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

M is H, or Na, or K, or $N^+R_1R_2R_3$ or a pharmaceutical salt. $R_1$, $R_2$ and $R_3$ are described above.

In another aspect, this invention provides a cell-binding agent-drug conjugate of formula (II), in which the cell-binding agent, Cb, and the drug, Drug, have reacted at the two ends of the charged linker:

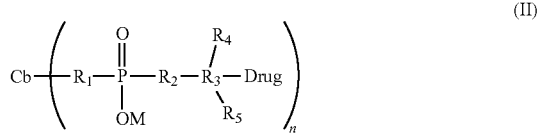

(II)

wherein:

Cb represents a cell-binding agent; n is 1~20.

Drug represents the drug linked to the cell-binding agent via the charged linker by a disulfide, thioether, thioester, peptide, hydrazone, ether, ester, carbamate, carbonate, cycloheteroalkyane, heteroaromatic, alkoxime or amide bond.

$R_1$, $R_2$, $R_3$, $R_4$, $R_5$, and M are described the same previously in formula (I).

In a further aspect, the present invention provides a modified cell-binding agent of formula (III), in which the cell-binding agent, Cb, has reacted with the charged linker, which still has Z, a group capable of reacting with a drug:

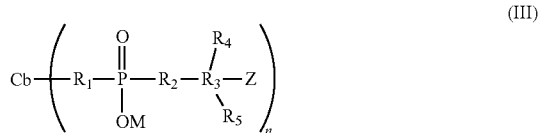

(III)

Wherein the substituents are as defined above.

In an even further aspect, the present invention provides a modified drug of formula (IV), in which the drug, Drug, has reacted with the charged linker, which still has Y, a group capable of reacting with the cell-binding agent:

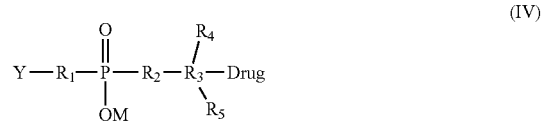

(IV)

Wherein the substituents are as defined above.

The present invention further relates to a method of making a cell-binding molecule-drug conjugate of formula (II), wherein the drug is linked to a cell-binding agent via the charged linker.

The present invention also relates to a method of making a modified cell-binding molecule of formula (III), wherein the cell-binding molecule is reacted with the charged linker.

The present invention also relates to a method of making a modified drug of formula (IV), wherein the drug is reacted with the charged linker.

BRIEF DESCRIPTION OF THE DRAWINGS

FIG. 21A. ADC structure of a tubulysin analog through a charged linker (via thioether bond).

FIG. 21Y. ADC structure of a duocarmycin analog vita a charged linker (peptide linkage).

DETAILED DESCRIPTION OF THE INVENTION

Definitions

Figure 1:
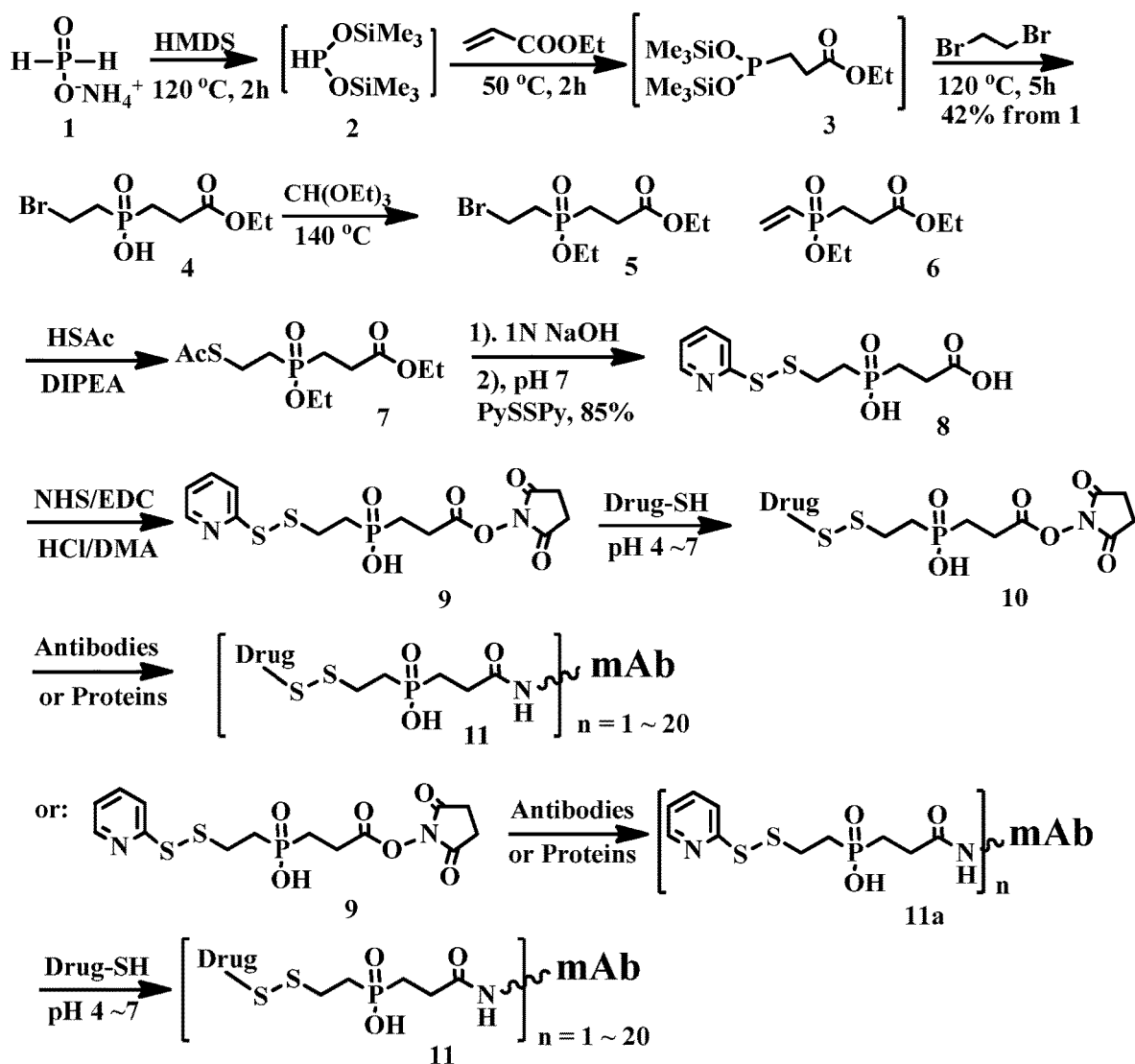
FIG. 1 shows the synthesis of phosphinate-containing cross-linking reagents that contain a pyridyldisulfide group and a reactive carboxylic acid ester, and the linker used for the conjugation of an antibody. Ammonium phosphinate are first converted into bis(trimethylsilyl) phosphonite, followed by Michael addition with an acrylate and then substitution reaction with excess amount of 1,2-dibromo ethane to form (2-bromoethyl)(3-ethoxy-3-oxopropyl)phosphinic acid (4). The bromoethyl phosphinic acid moiety (5) was then substituted with thioacetate after the phosphinic acid (4) was protected with triethoxymethane, followed by basic hydrolysis, Substitution reaction with an excess of 2,2'-dithiobispyridine, and condensation reaction of the acid 8 with N-hydroxysuccimide (NHS) in an acid medium using the carbodiimide coupling agent EDC to give the phosphinate linker, which then can be used for the preparation of an antibody-drug conjugate.
Figure 2:
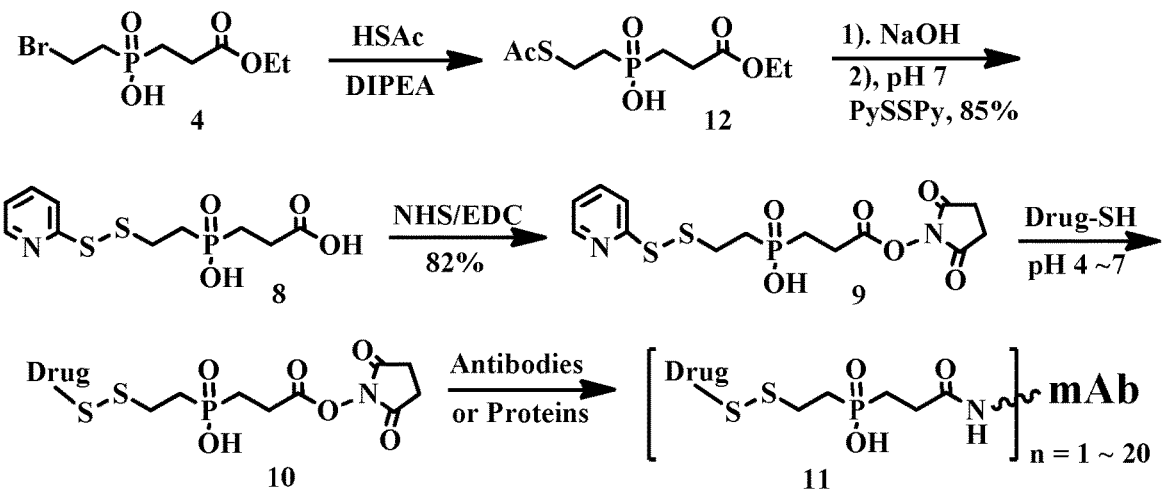
FIG. 2 shows the synthesis of a phosphinate-containing linker that contains a pyridyldisulfide group and a reactive carboxylic acid ester via direct substitution of bromoethyl phosphinic acid moiety (4) by thioacetate without protecting the phosphinic acid group. The linker is used for the conjugation of an antibody via a disulfide bond.

"Alkyl" means an aliphatic hydrocarbon group which may be straight or branched having 1 to 8 carbon atoms in the chain or cyclic. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$~$C_8$ alkyl, —O—($C_1$~$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen (F, Cl, Br or I), —N$_3$, —NH$_2$, —NH(R'), —N(R')$_2$ and —CN; where each R' is independently selected from —$C_1$~$C_8$ alkyl and aryl.

A "$C_3$~$C_8$ carbocycle" means a 3-, 4-, 5-, 6-, 7- or 8-membered saturated or unsaturated non-aromatic carbocyclic ring. Representative $C_3$~$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$~$C_8$ carbocycle group can be unsubstituted or substituted with one or more groups including, but not limited to, —$C_1$~$C_8$ alkyl, —O—($C_1$~$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from —$C_1$~$C_8$ alkyl and aryl.

A "$C_3$~$C_8$ carbocyclo" refers to a $C_3$~$C_8$ carbocycle group defined above wherein one of hydrogen atoms on the carbocycle is replaced with a bond.

"Heterocycle" refers to an aromatic or non-aromatic $C_3$~$C_{14}$ carbocycle in which one to four of the ring carbon atoms are independently replaced with a heteroatom from the group of O, N, S Se, and P. Preferable heteroatoms are oxygen, nitrogen and sulphur. Suitable heterocyclics are also disclosed in *The Handbook of Chemistry and Physics*, 76$^{th}$ Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrinidinyl, dihydrothiopyranyl, azepanyl, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Halogen atom" refers to fluorine, chlorine, bromine or iodine atom; preferably bromine and chlorine atom.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared by reacting the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

The novel conjugates disclosed herein use hydrophilic phosphinate cross-linkers. Examples of some suitable cross-linkers and their synthesis are shown in FIGS. 1 to 23.

The Charged Linkers

The synthetic routes to produce phosphinate-containing charged crosslinkers as well as the preparation of the antibody-drug conjugates of the present invention are shown in FIGS. 1-20. The charged crosslinkers possess three elements: a) a substituent that is either charged phosphinate, b) a group, such as a N-hydroxysuccimimide ester, maleimido group, haloacetyl group, and hydrazide, capable of reaction with a cell-binding agent, and c) a group, such as but not limited to, a disulfide, maleimide, haloacetyl, aldehyde, ketone, azide, amine, alkoxylamino and hydrazide, capable of reaction with a drug. The charged phosphinate substituent can be introduced by methods described herein. For example, it can be introduced by first treating a commercially available ammonium phosphinate with an acrylate via Michael addition and followed by substitution of excess amount of dibromo alkane to a phosphinate group. Alternatively a charged phosphinate substituent can be introduced by double displacement of haloalkanes with the phosphinates such as disclosed in FIG. 11. More detail synthesis of the charged phosphinate linkers and their uses for the preparation of cell binding ligand-drug conjugates of this invention are disclosed in the FIGS. 1~20.

Preferably, the charged linkers are compounds of the formula (I) below:

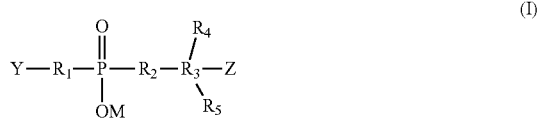

wherein:

Y represents a functional group that enables reaction with a cell-binding agent;

Z represents a functional group that enables linkage of a cytotoxic drug via a disulfide, thioether, thioester, peptide, hydrazone, ether, ester, carbamate, carbonate, amine (secondary, tertiary, or quartary), imine, oximine, cycloheteroalkyane, heteroaromatic or amide bond;

M is H, or Na, or K, or $N^+R_1R_2R_3$ or a pharmaceutical salt.

$R_1$, $R_2$, $R_3$, $R_4$, and $R_5$, are the same or different and are H, linear alkyl having from 1-6 carbon atoms, branched or cyclic alkyl having from 3 to 6 carbon atoms, linear, branched or cyclic alkenyl or alkynyl or polyethyleneoxy unit of formula $(OCH_2CH_2)_p$, wherein p is an integer from 0 to about 1000.

In another embodiment, $R_1$, $R_2$, and $R_3$ can be respectively a chain of atoms selected from C, N, O, S, Si, and P that covalently connects the cell-surface binding ligand, the phosphinate group, the conjugated drug and themselves ($R_1$, $R_2$ and $R_3$). The atoms used in forming the charged linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, hydroxamic acids, and many others. In addition, it is to be understood that the atoms forming the linker (L) may be either saturated or unsaturated, or may be radicals, or may be cyclized upon each other to form divalent cyclic structures, including cyclo alkanes, cyclic ethers, cyclic amines, arylenes, heteroarylenes, and the like in the linker.

Examples of the functional group, Y, that enables reaction with a cell-binding agent include amine reacting agents such as but not limited to N-hydroxysuccinmide esters, p-nitrophenyl esters, dinitrophenyl esters, pentafluorophenyl esters; thiol reactive agents such as but not limited to pyridyldisulfides, nitropyridyldisulfides, maleimides, haloacetates and carboxylic acid chlorides.

Examples of the functional group, Z, which enables linkage of a cytotoxic drug, include groups that enable linkage via a disulfide, thioether, thioester, peptide, hydrazone, ester, carbamate, carbanate, or amide bond. Such functional groups include, but are not limited to, thiol, disulfide, amino, carboxy, aldehydes, maleimido, haloacetyl, hydrazines, and hydroxy.

In preferred embodiments, $R_1$, $R_2$, and $R_3$, are linear alkyl having from 1-6 carbon atoms, or polyethyleneoxy unit of formula $(OCH_2CH_2)_p$, p=1~100.

Figure 3:
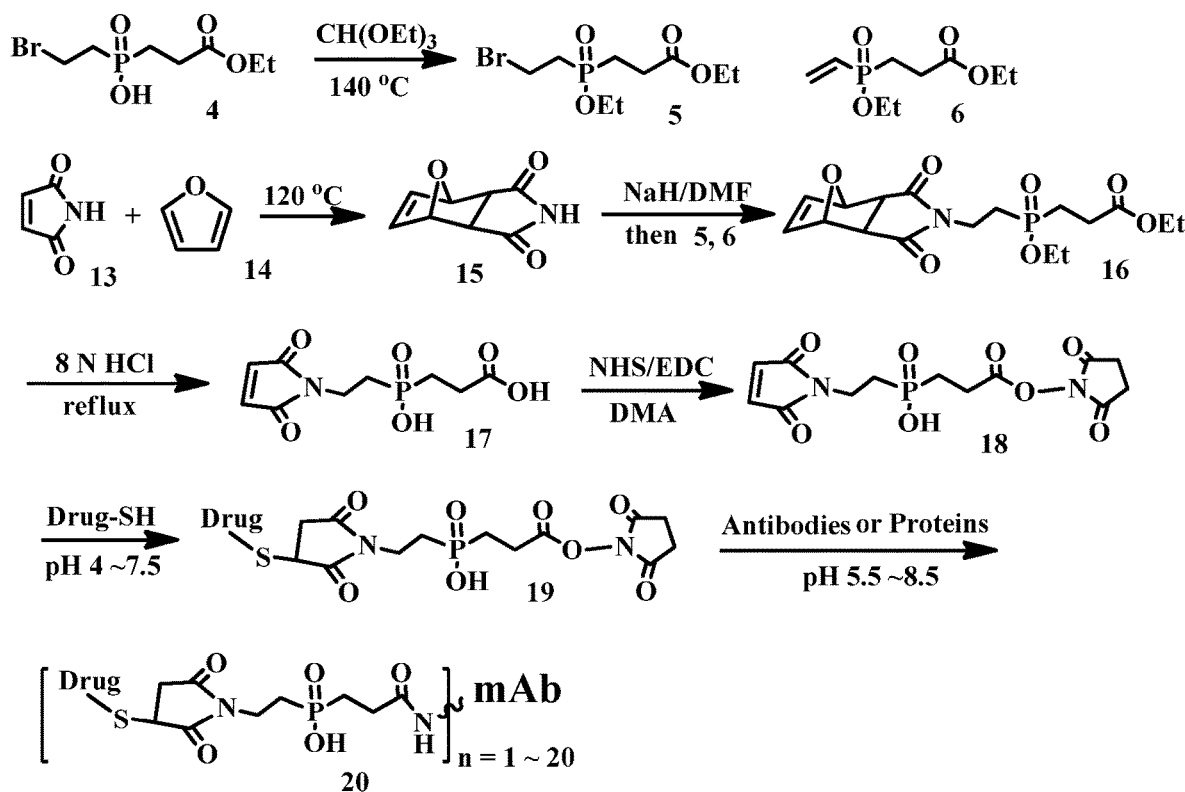
FIG. 3 shows the synthesis of phosphinate-containing cross linkers that contain a reactive carboxylic acid ester and a maleimido substituent, enabling linkage of an antibody or a protein via a thioether bond.
Figure 4:
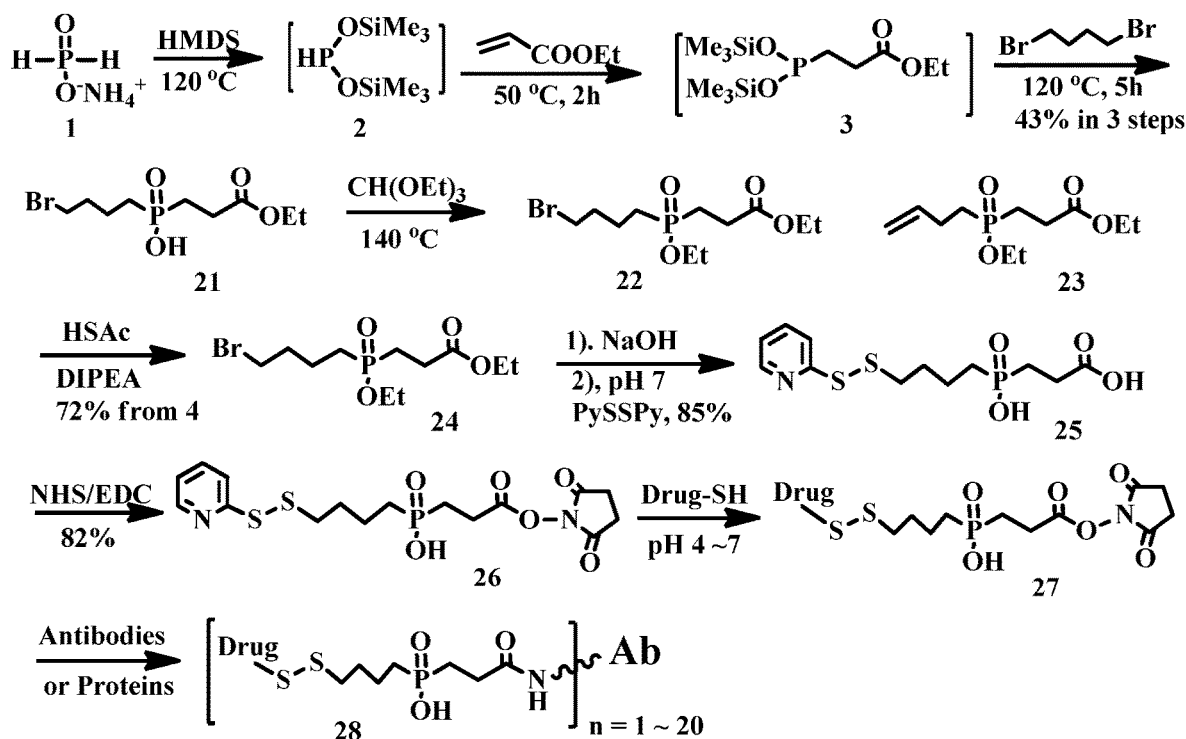
FIG. 4 shows the synthesis of phosphinate-containing cross-linker that contain a pyridyldisulfide group and a reactive carboxylic acid ester via substitution of 1,4-dibromobutane. The linker is used for the conjugation of an antibody via a disulfide bond.
Figure 5:
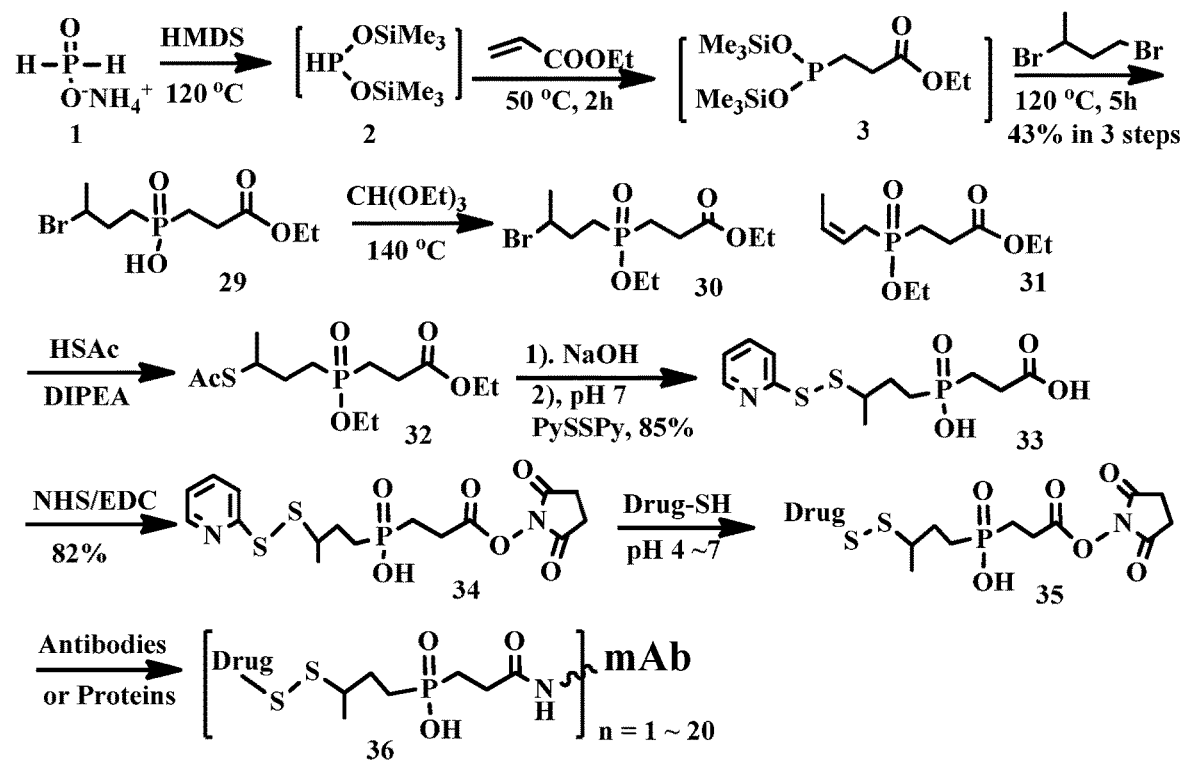
FIG. 5 shows the synthesis of phosphinate-containing linker that contain a hindered pyridyldisulfide group and a reactive carboxylic acid ester via substitution of 1,3-dibromobutane. The linker is used for the conjugation of an antibody or a protein via a hinder disulfide bond.
Figure 6:
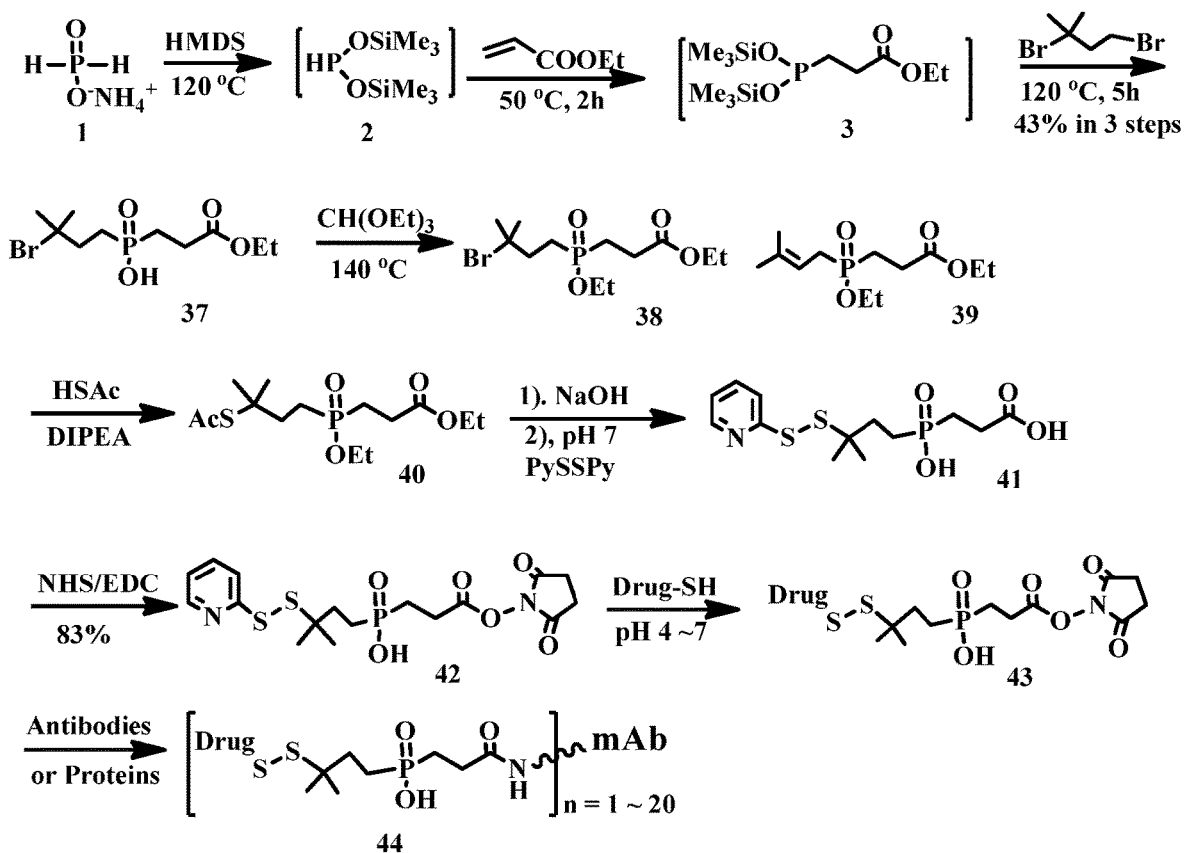
FIG. 6 shows the synthesis of phosphinate-containing cross-linking reagents that contain a very hindered pyridyldisulfide group and a reactive carboxylic acid ester via substitution of 1,3-dibromo-3-methylbutane.
Figure 7:
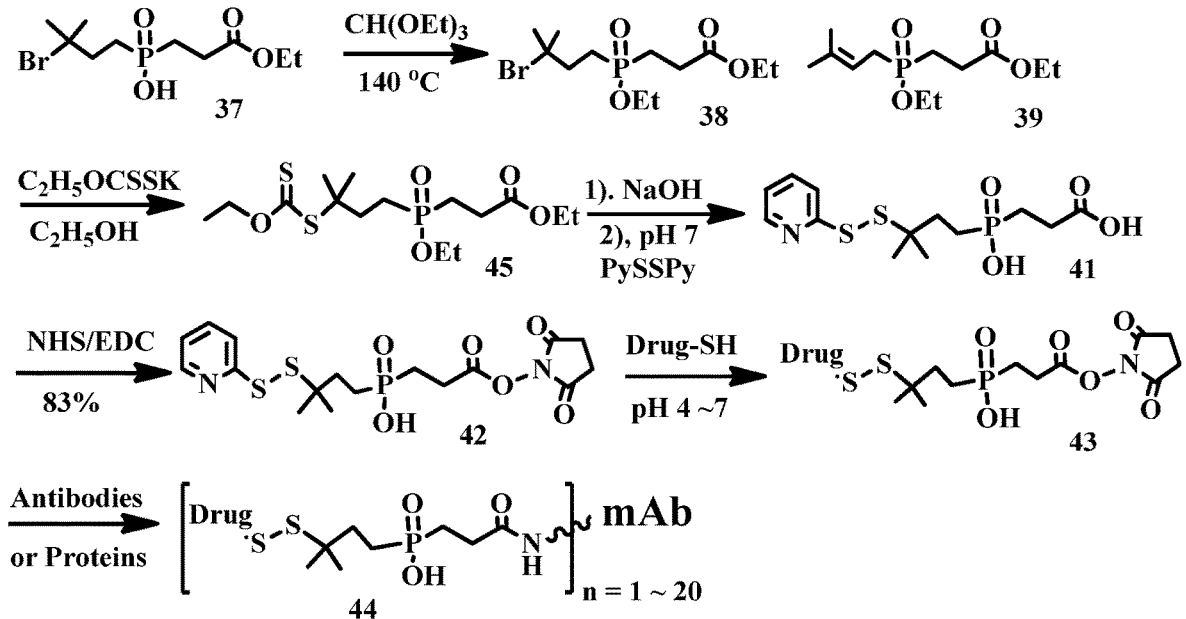
FIG. 7 shows the synthesis of phosphinate-containing linkers that contain a hindered pyridyldisulfide group and a reactive carboxylic acid ester via direct substitution of 2-bromo-2-methyl-buthyl phosphinic acid moiety with potassium O-ethyl carbonodithioate.
Figure 8:
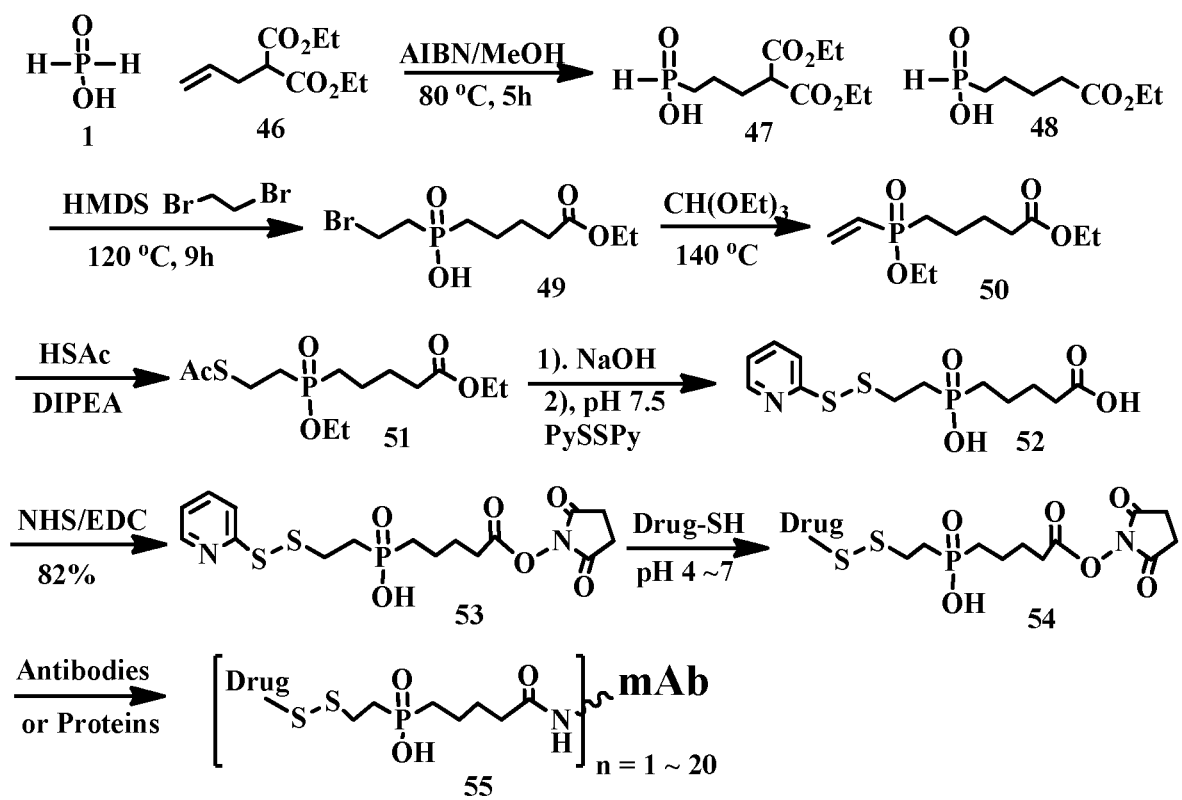
FIG. 8 shows the synthesis of phosphinate-containing linkers that contain a pyridyldisulfide group and a reactive carboxylic acid ester via addition reaction of phosphinic acid to a double bond. The linker is used for the conjugation of an antibody or a protein via a disulfide bond.
Figure 9:
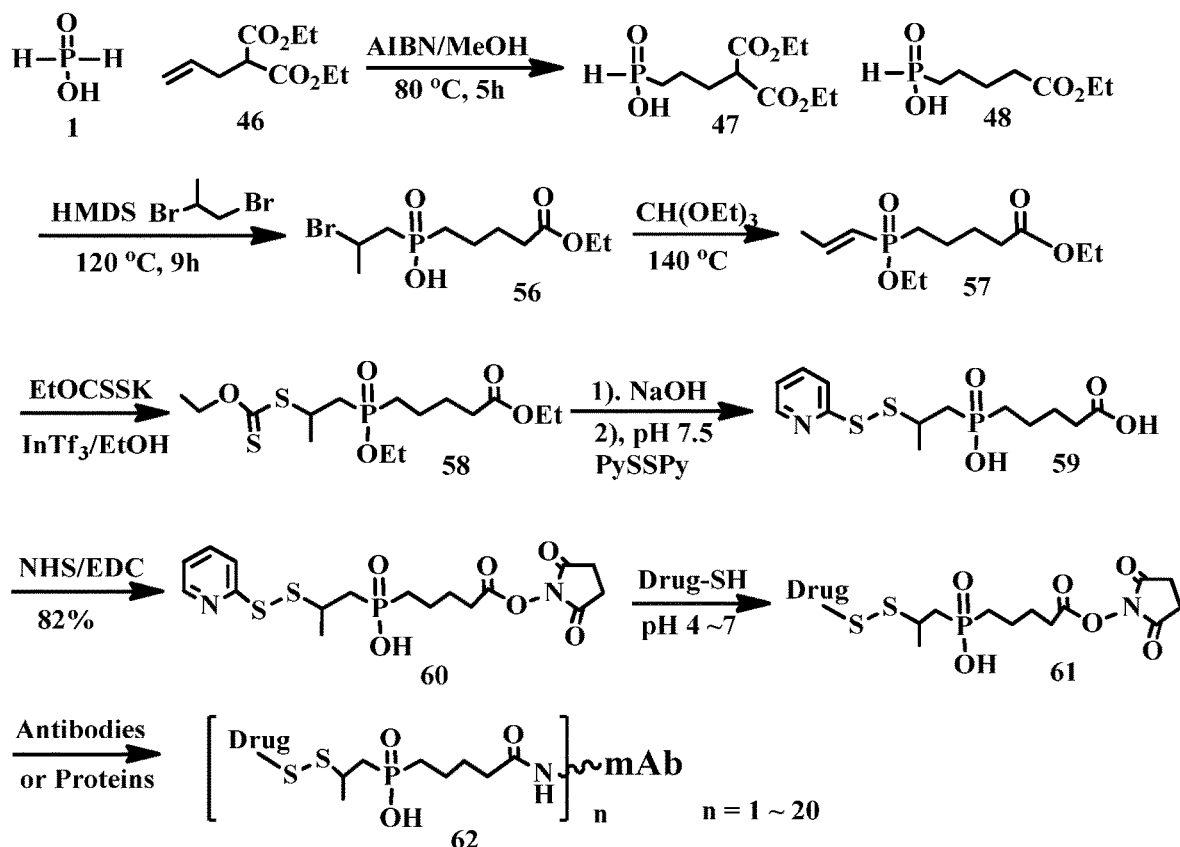
FIG. 9 shows the synthesis of phosphinate-containing linker that contain a hinder pyridyldisulfide group and a reactive carboxylic acid ester via an addition reaction of phosphinic acid to diethyl 2-allylmalonate. The linker is used for the conjugation of an antibody or a protein via a hinder disulfide bond.
Figure 10:
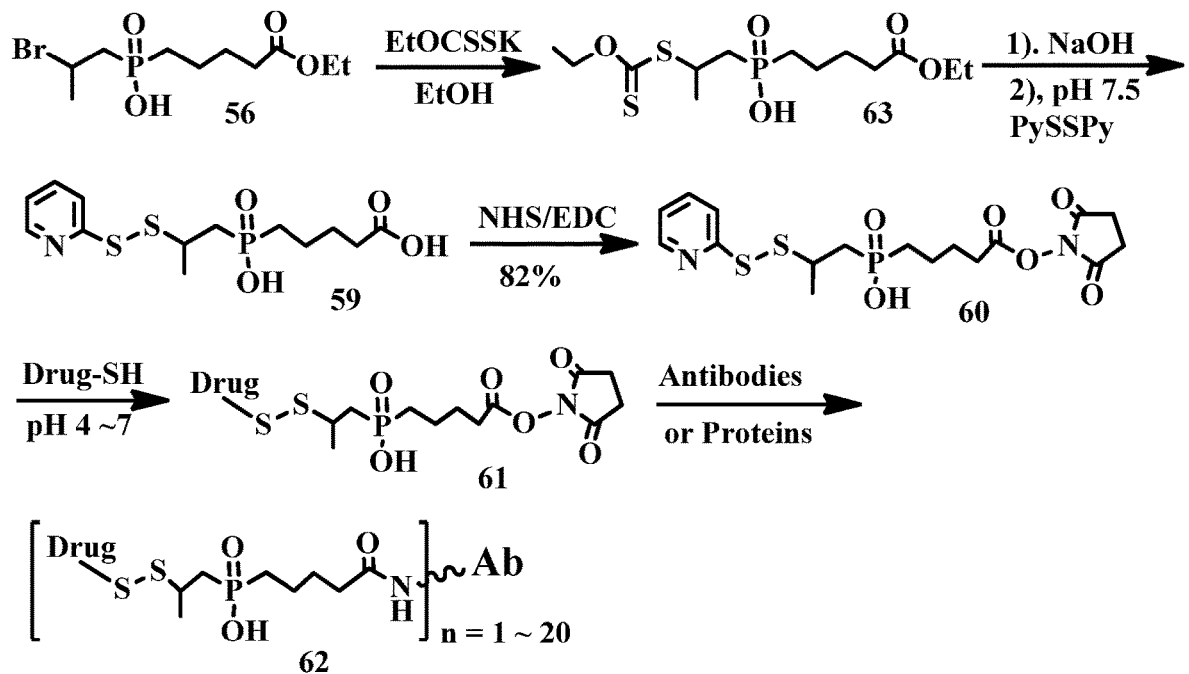
FIG. 10 shows the synthesis of phosphinate-containing linkers that contain a hinder pyridyldisulfide group and a reactive carboxylic acid ester via substitution reaction of a hinder bromide with a xanthogenate.
Figure 11:
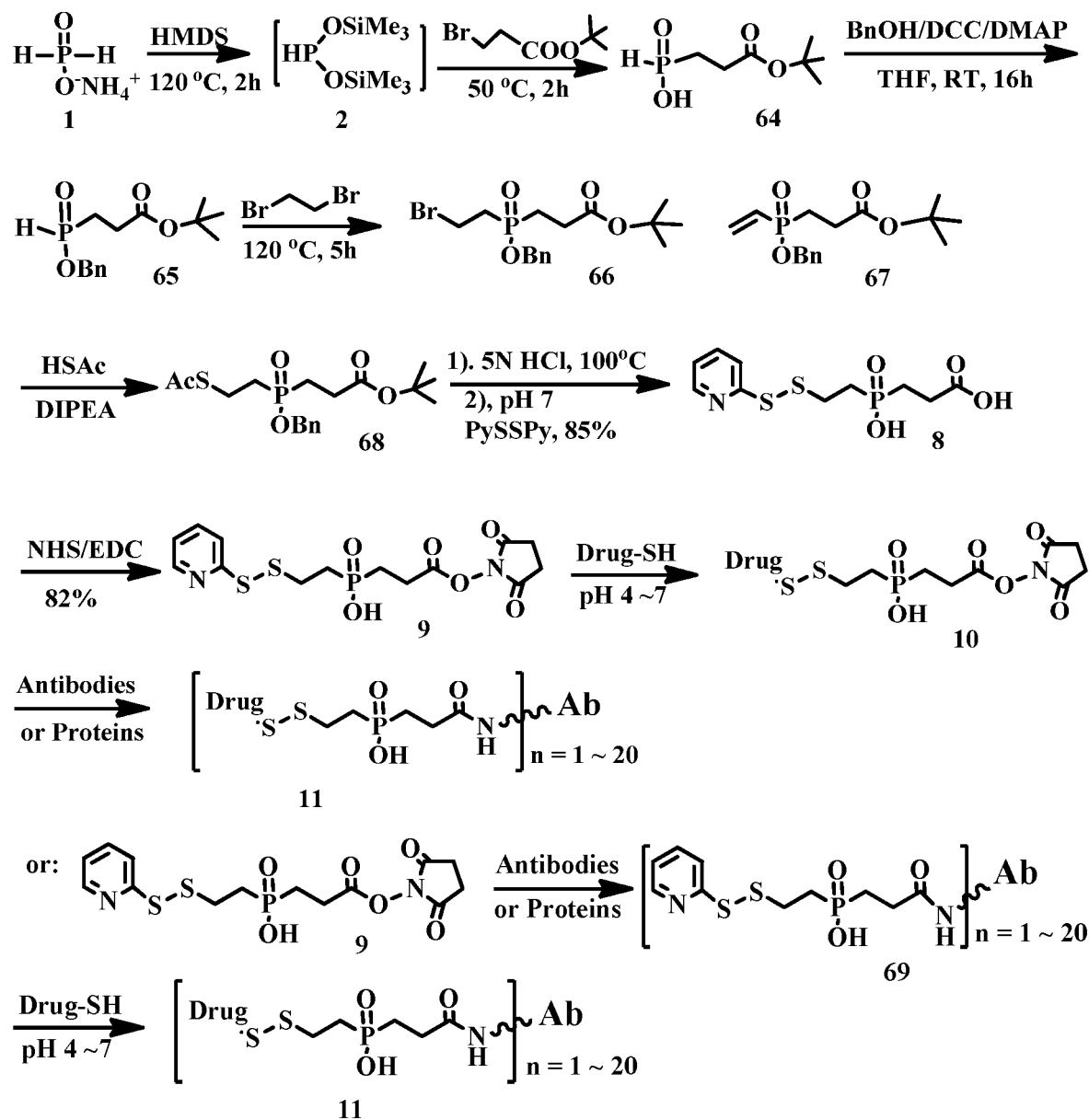
FIG. 11 shows the synthesis of phosphinate-containing linkers that contain a pyridyldisulfide group and a reactive carboxylic acid ester via substitution reaction of alkyl bromides with ammonium phosphinate.
Figure 12:
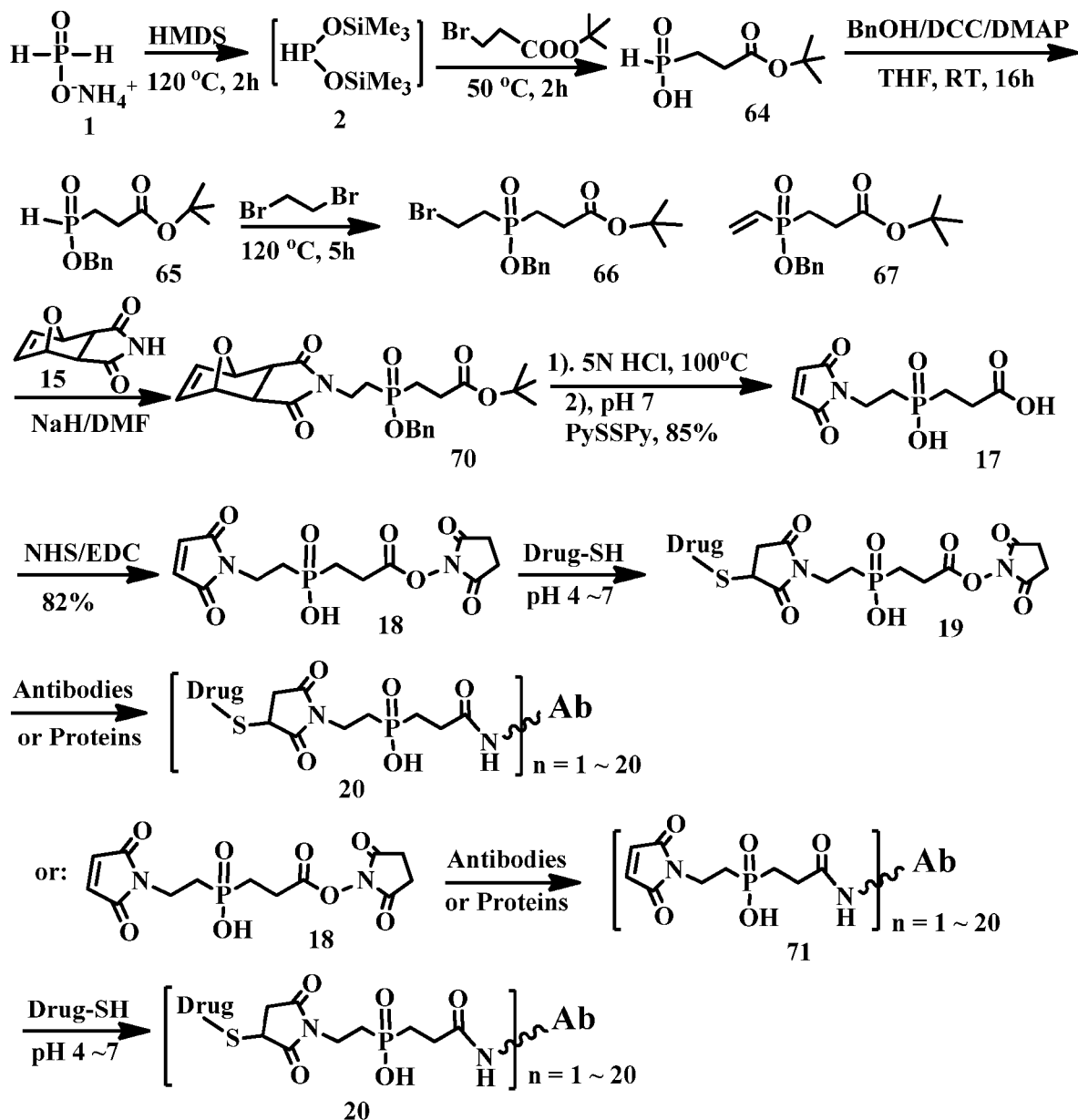
FIG. 12 shows the synthesis of phosphinate-containing linkers that have a reactive carboxylic acid ester and a maleimido substituent, enabling linkage cell binding molecule—drug conjugates via thioether bonds.
Figure 13:
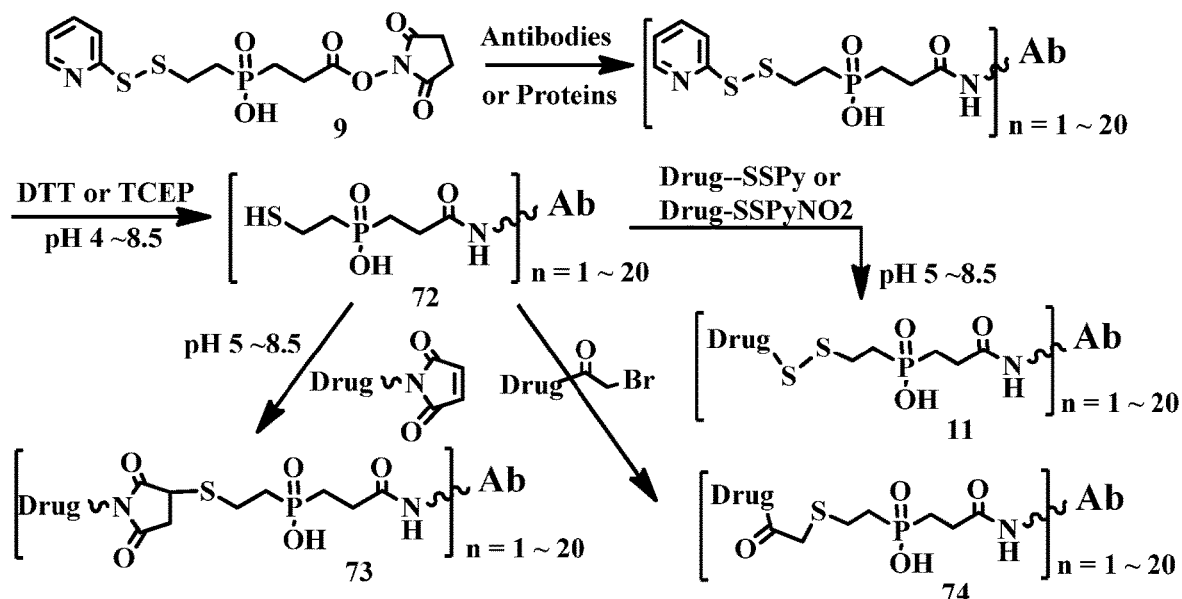
FIG. 13 shows the synthesis of the antibody-drug conjugates with phosphinate-containing linkers of this patent through the first reduction of the disulfide bond of the antibody-linker conjugates, follow by reaction with thiol-reactive drugs.
Figure 14:
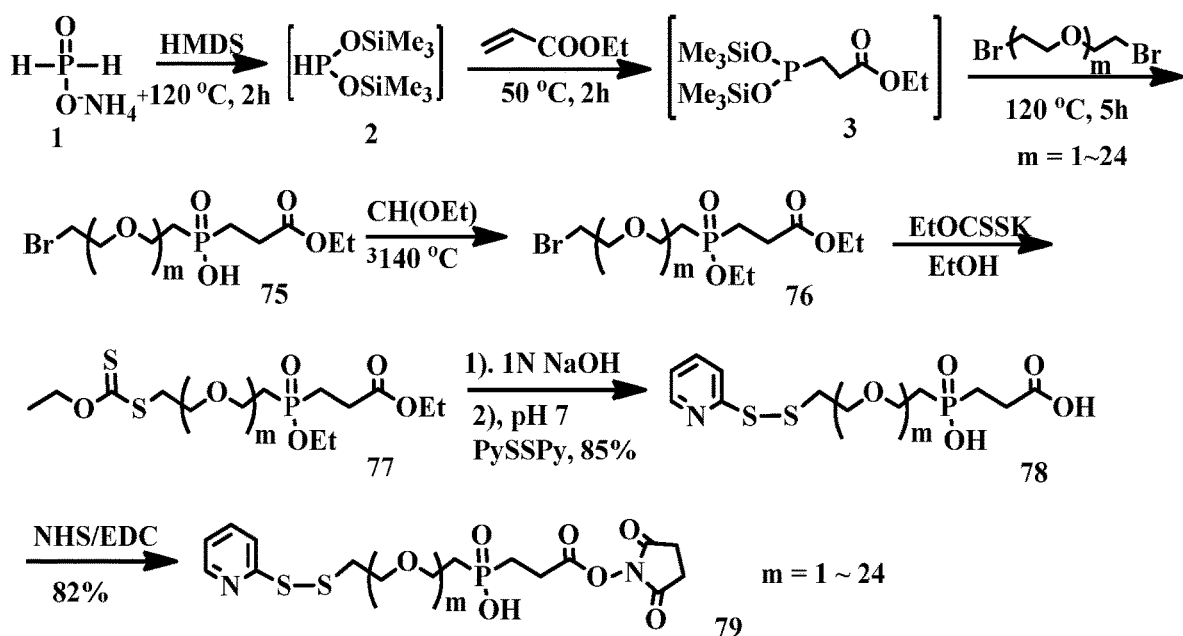
FIG. 14, shows synthesis of phosphinate-containing cross-linkers that contain a pyridyldisulfide group, a polyethyleneglycol (PEG) chain and a reactive carboxylic acid ester. The linkers are used for the conjugation of a cell binding molecule via disulfide bond.
Figure 15:
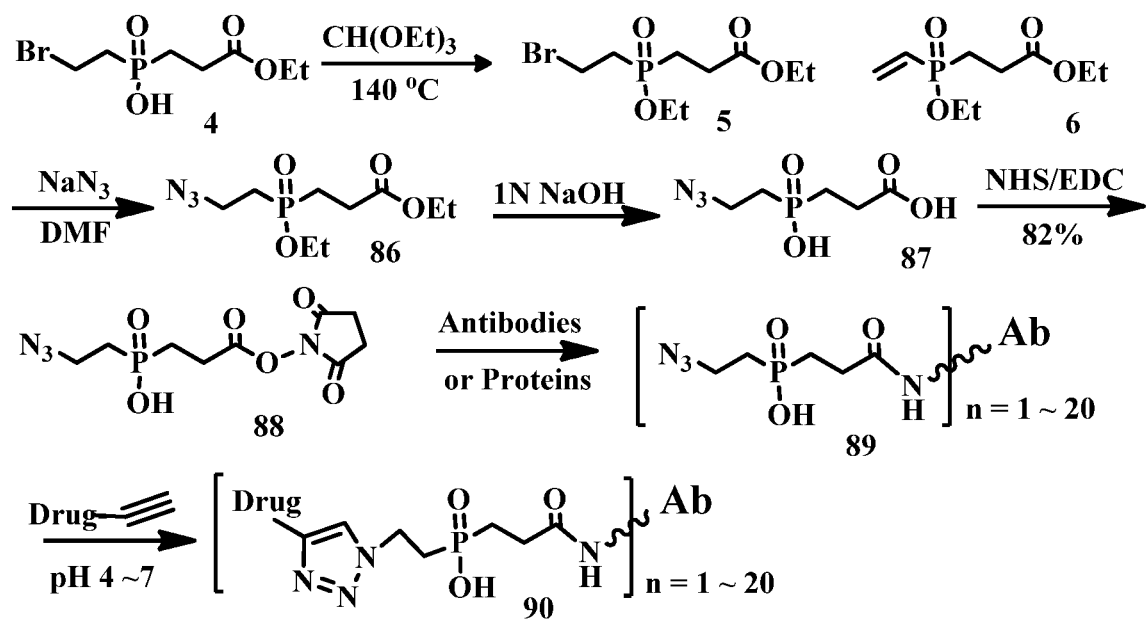
FIG. 15 shows synthesis of phosphinate-containing linkers that contain an azide group and a reactive carboxylic acid ester. The linkers are used for the conjugation of a cell binding molecule to a drug via a click chemical reaction.
Figure 16:
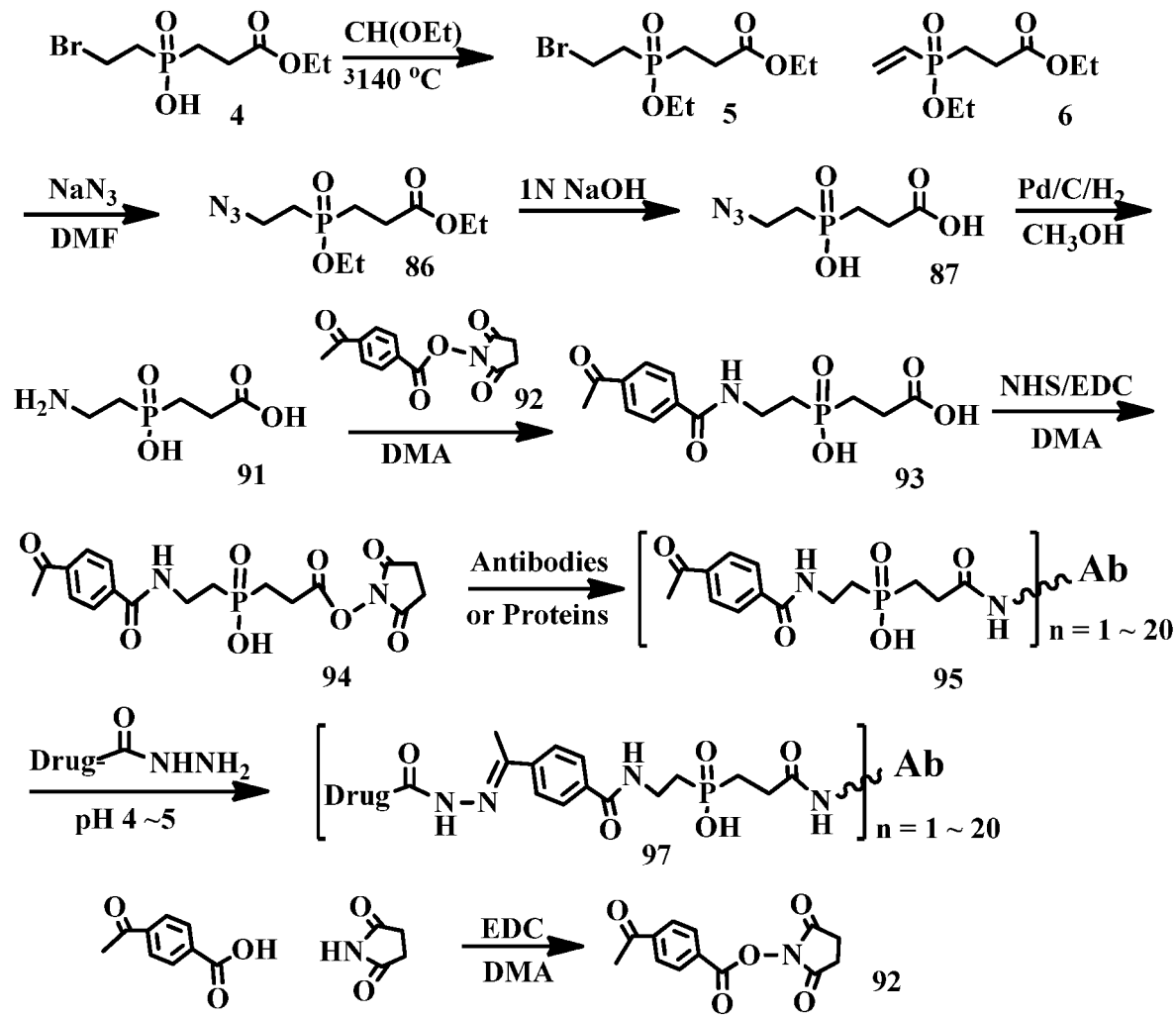
FIG. 16 shows the synthesis of a phosphinate-containing linker that contains a ketone and a NHS ester, enabling an antibody-drug conjugation via a hydrazone bond.
Figure 17:
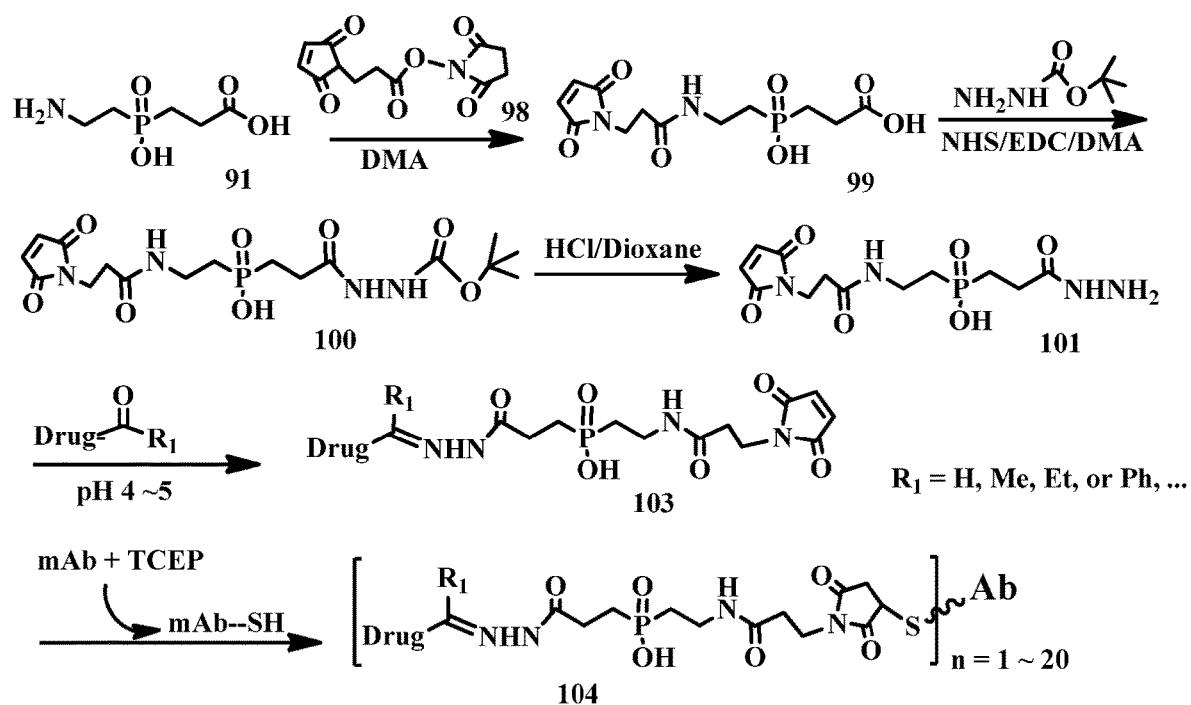
FIG. 17 shows the synthesis of a phosphinate-containing linker that contains a hydrazine and a maleimido substituent, enabling linkage of a drug to an antibody via a hydrazone bond.
Figure 18:
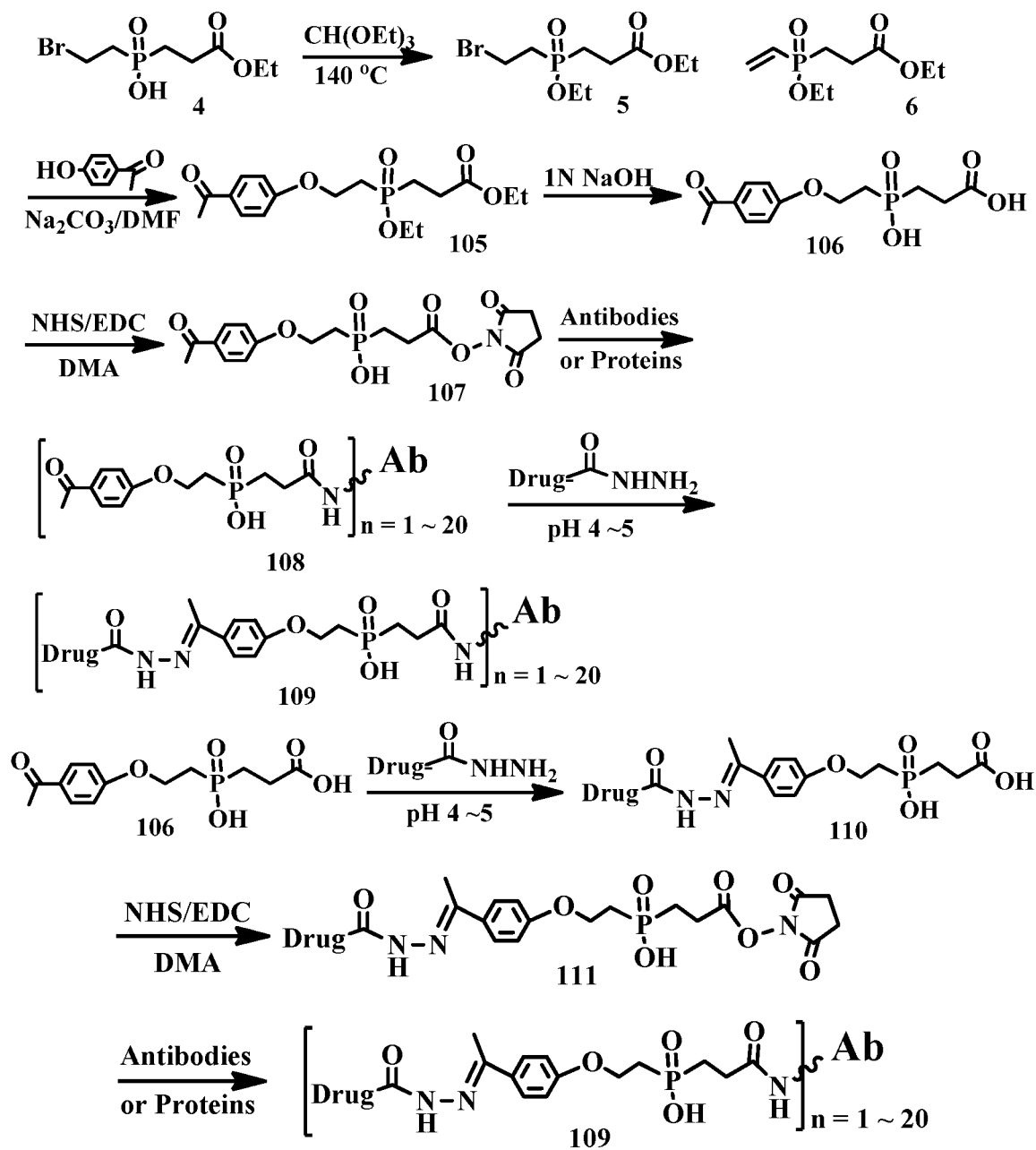
FIG. 18 show the synthesis of a phosphinate-containing linker that contains a ketone and a NHS ester, enabling hydrazine-containing drugs to link to an antibody via a hydrazone bond.
Figure 19:
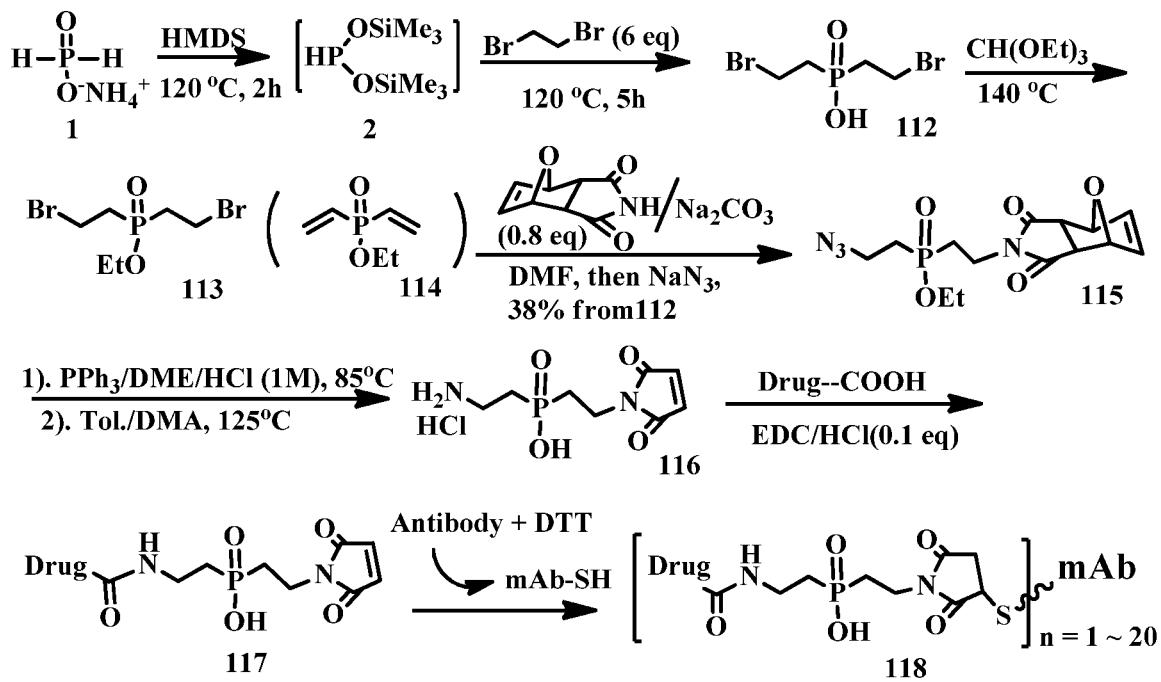
FIG. 19 shows the synthesis of a phosphinate-containing linker that contains an amine and a maleimido substituent, enabling an antibody-drug conjugate via a thioether and an amide bond linkage.
Figure 20:
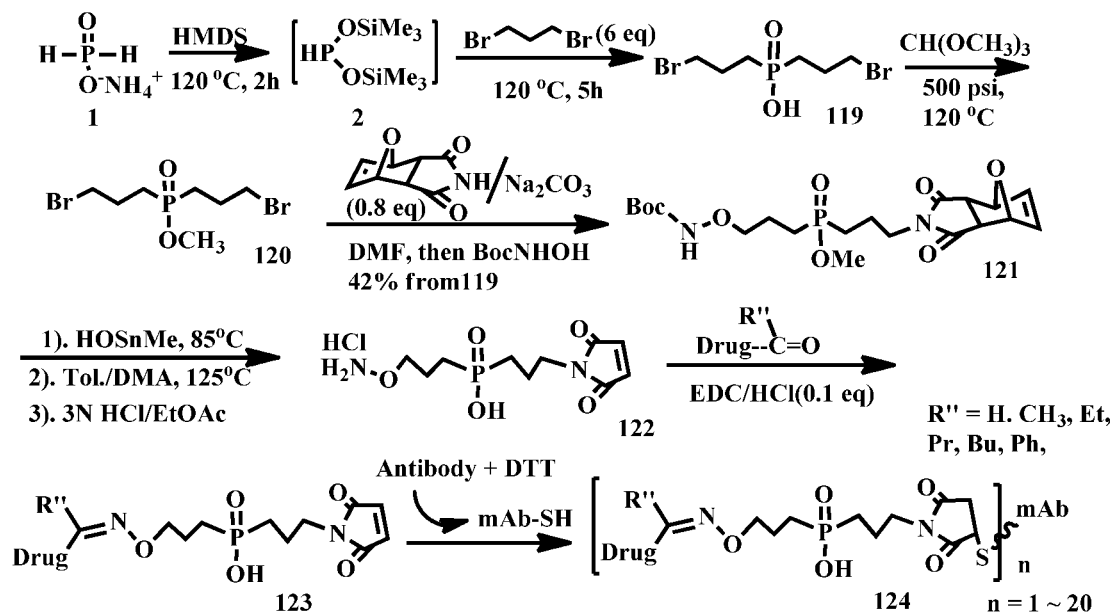
FIG. 20 shows the synthesis of a phosphinate-containing linker that contains an alkoxylamino and a maleimido substituent, enabling ketone or aldehyde-containing drug to link to an antibody via a thioether and an alkoxime bond.
Figure 21A:
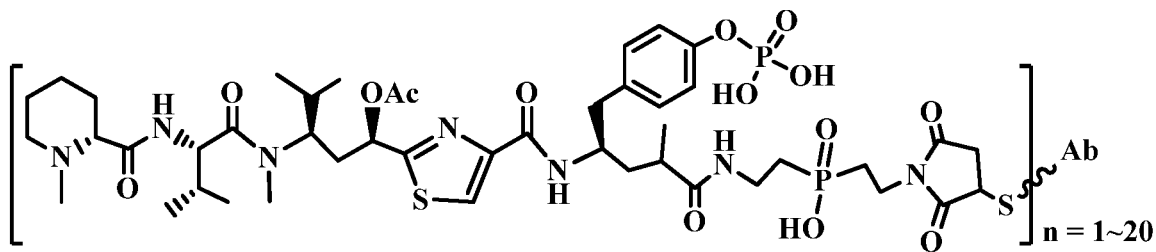
FIGS. 21A-21Y show the antibody-drug conjugate (ADC) structures of the typical cytotoxic agents (the analogs of tubulysins, calicheamicins, maytansinoids, auristatins, doxorubicin, daunorubicin, CC-1065, pyrrolobenzodiazepine dimmers) via the charged linkers of disclosure.
Figure 21B:
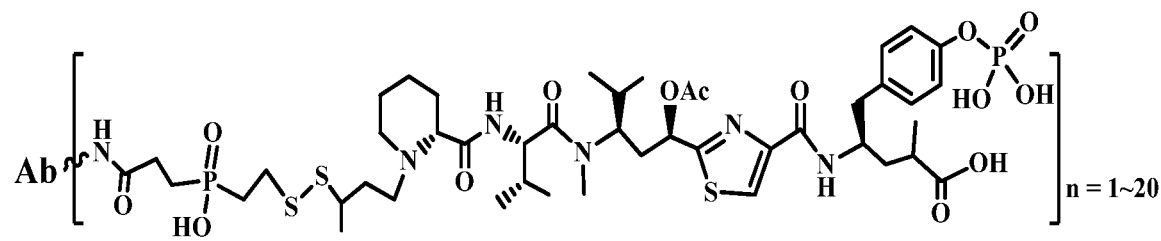
FIG. 21B. ADC structure of a tubulysin analogy through a charged linker (via disulfide bond).
Figure 21C:
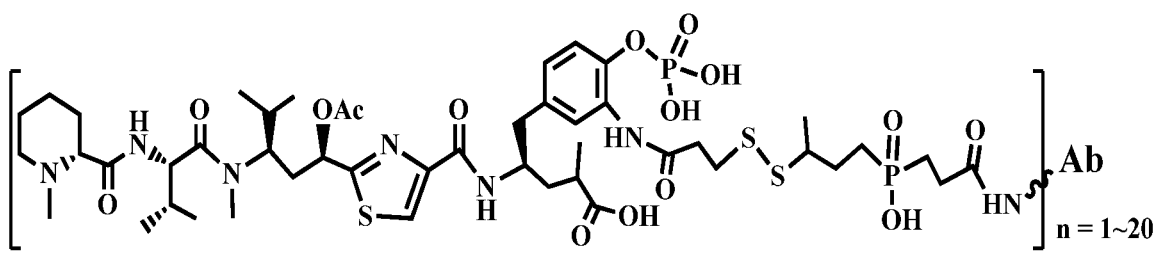
FIG. 21C. ADC structure of a tubulysin analog through a charged linker (via thioether bond).
Figure 21D:
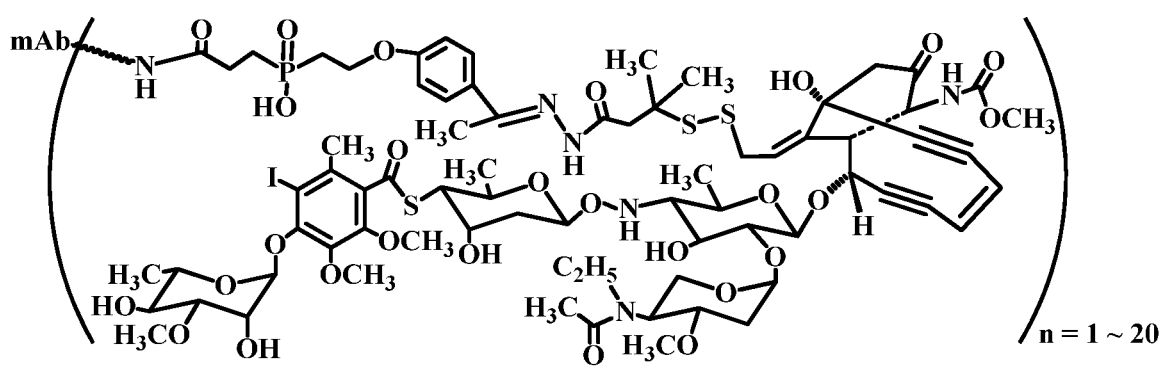
FIG. 21D. ADC structure of a calicheamicin analog through a charged linker (hydrazone and disulfide linkage).
Figure 21E:
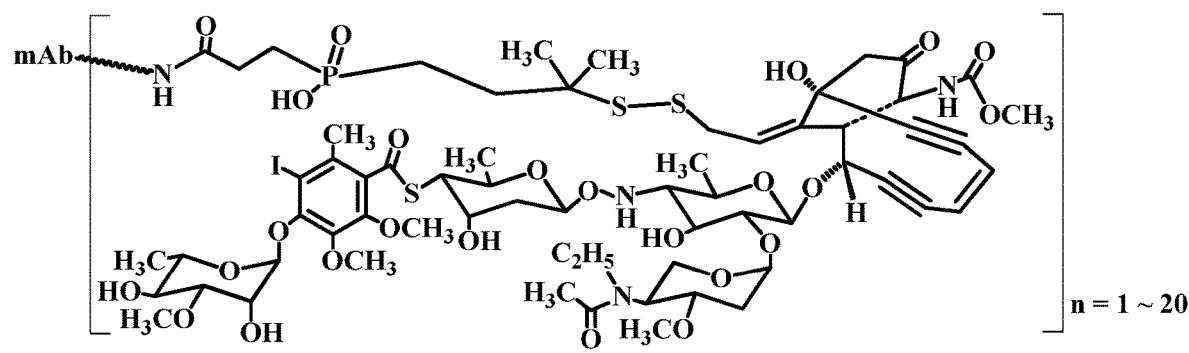
FIG. 21E. ADC structure of a calicheamicin analog via a charged linker (disulfide linkage).
Figure 21F:
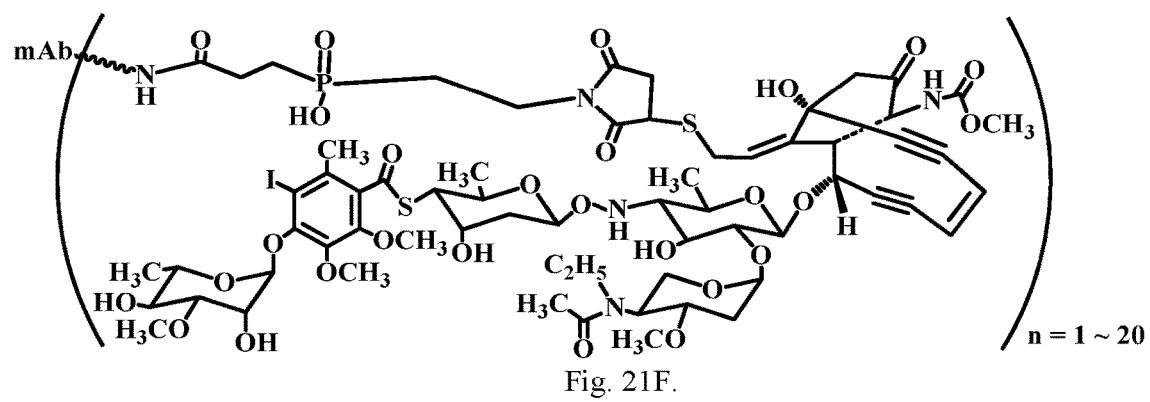
FIG. 21F, ADC structure of a calicheamicin analog via a charged linker (thioether linkage).
Figure 21G:
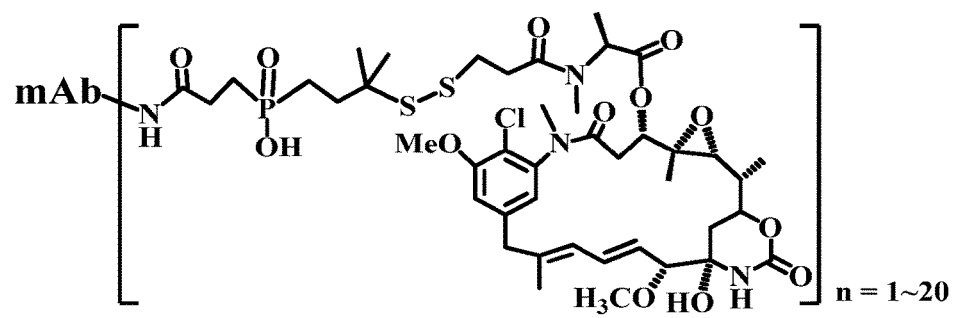
FIG. 21G. ADC structure of a Maytansinoid (DM1) a charged linker (disulfide linkage).
Figure 21H:
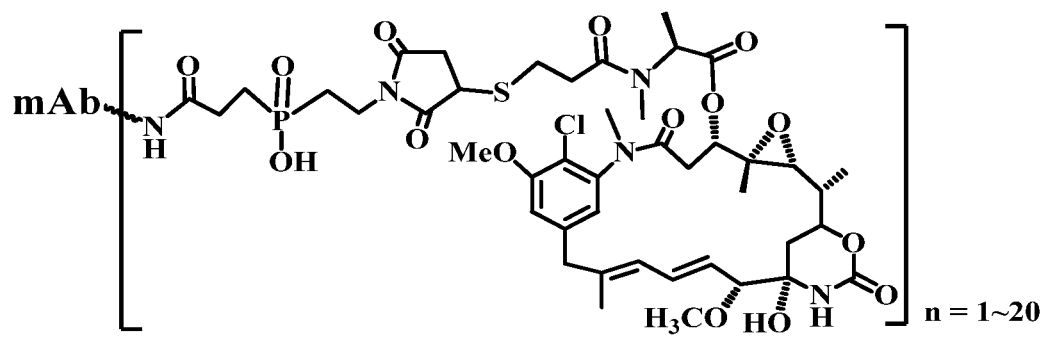
FIG. 21H. ADC structure of a Maytansinoid (DM1) via a charged linker (thioether linkage).
Figure 21I:
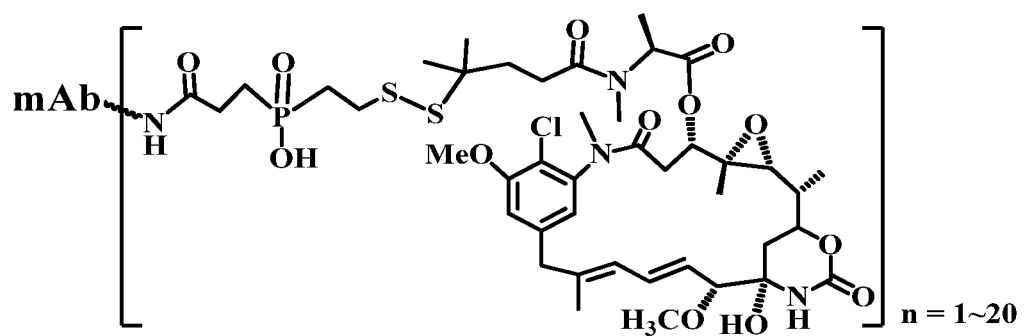
FIG. 21I. ADC structure of a Maytansinoid (DM4) via a charged linker (disulfide linkage).
Figure 21J:
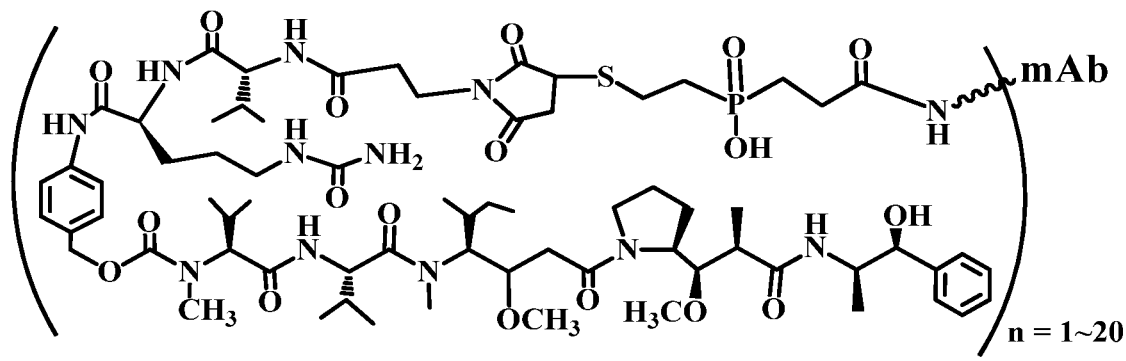
FIG. 21J. ADC structure of an auristatin analog (monomethyl auristatin E (MMAE)) through a charged linker (thioether and citrulline-valine peptide linkage).
Figure 21K:
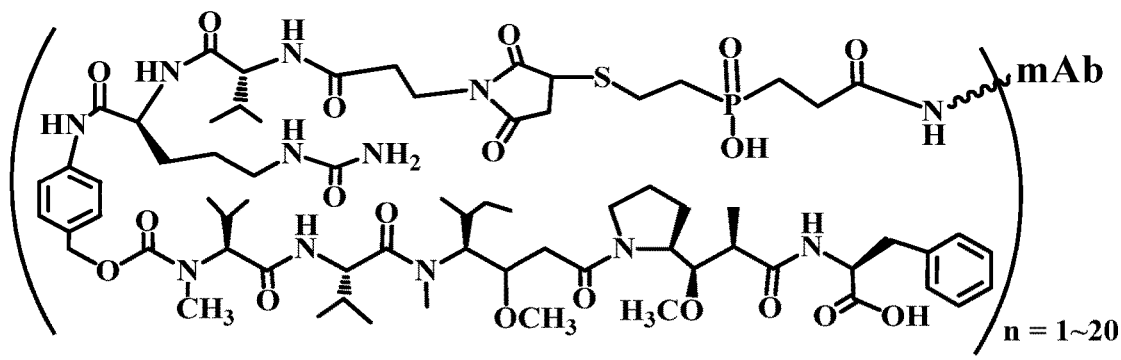
FIG. 21K. ADC structure of an auristatin analog (monomethyl auristatin F (MMAF)) through a charged linker (thioether and citrulline-valine peptide linkage).
Figure 21L:
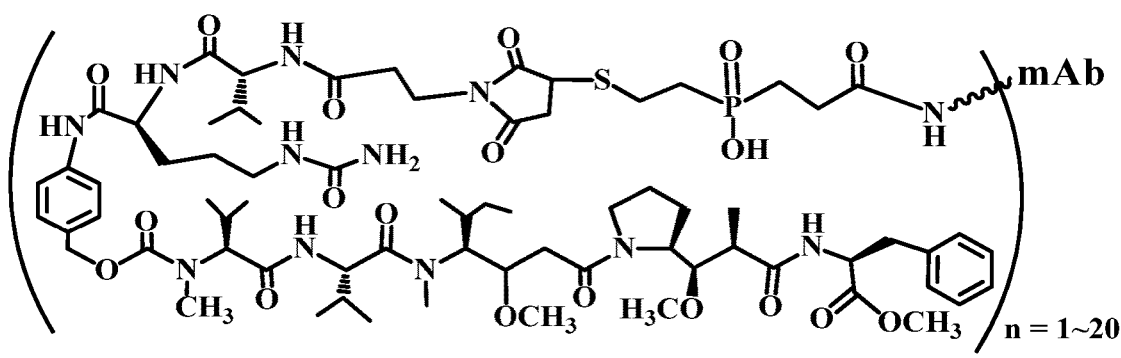
FIG. 21L. ADC structure of monomethyl auristatin F-ome (MMAF-ome) through a charged linker (thioether and citrulline-valine peptide linkage).
Figure 21M:
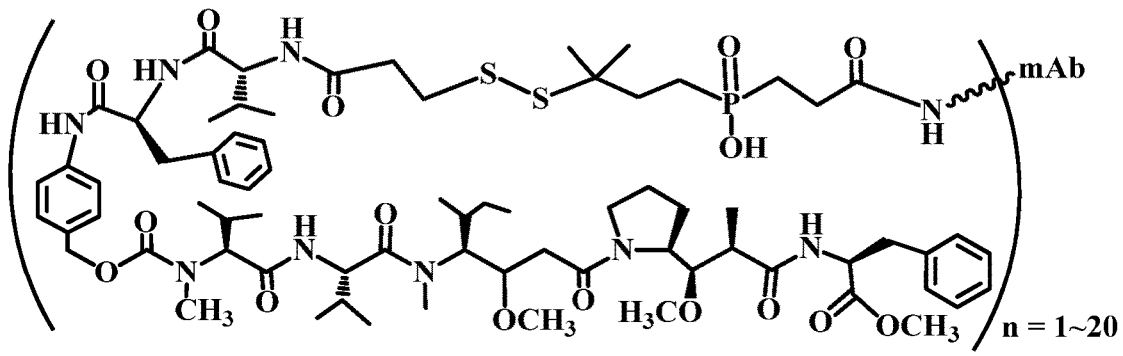
FIG. 21M. ADC structure of monomethyl auristatin F-ome (MMAF-ome) through a charged linker (disulfide and citrulline-valine peptide linkage).
Figure 21N:
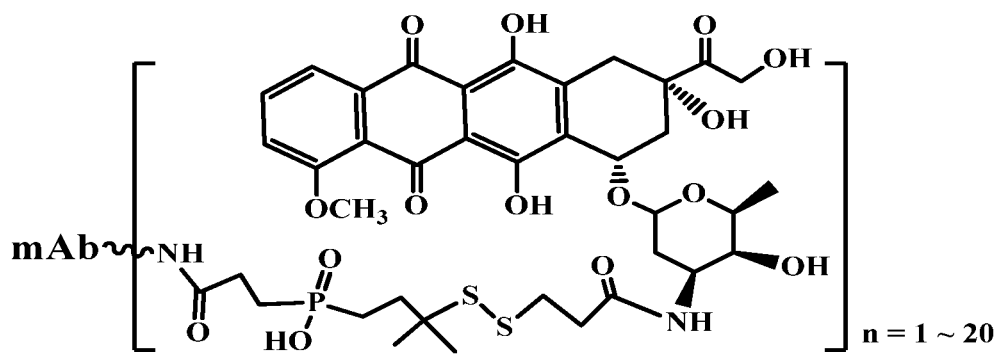
FIG. 21N. ADC structure of a doxorubicin compound via a charged linker (disulfide linkage).
Figure 21O:
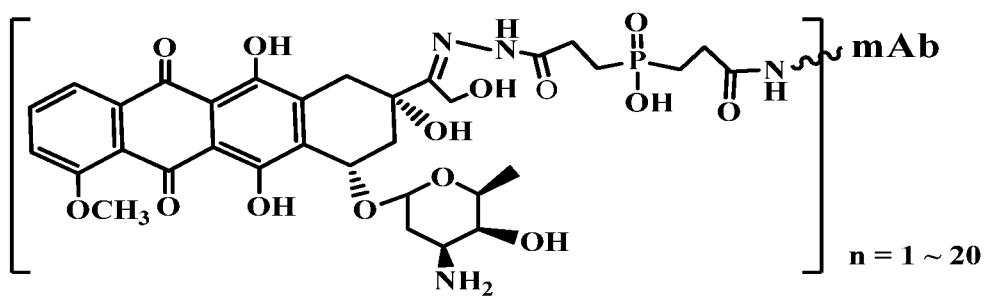
FIG. 21O. ADC structure of a doxorubicin compound via a charged linker (hydrazone linkage).
Figure 21P:
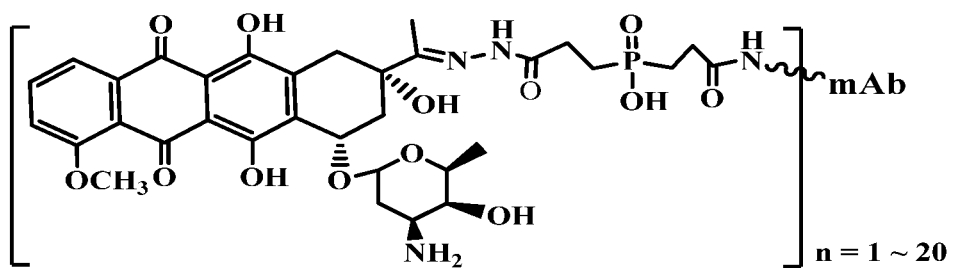
FIG. 21P. ADC structure of a daunorubicin via a charged linker (hydrazone linkage).
Figure 21Q:
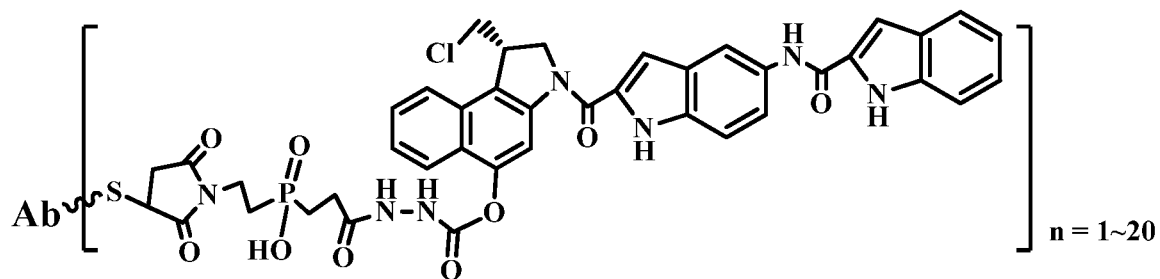
FIG. 21Q. ADC structure CC-1065 analog through a charged linker (hydrazine carboxylate linkage).
Figure 21R:
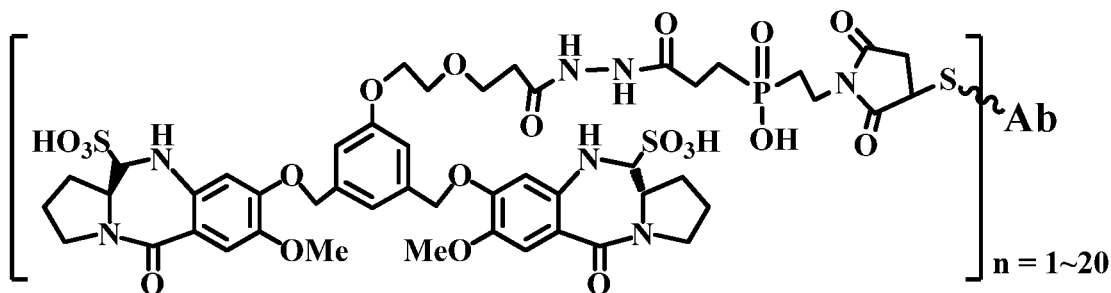
FIG. 21R. ADC structure of a pyrrolobenzodiazepine dimer prodrug through a charged linker (hydrazide linkage).
Figure 21S:
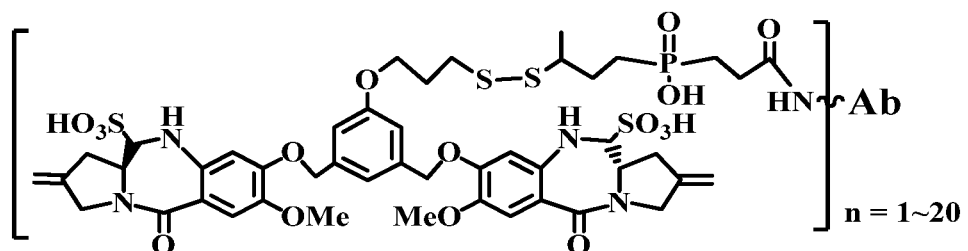
FIG. 21S. ADC structure of a pyrrolobenzodiazepine dimer prodrug through a charger linker (disulfide bond linkage).
Figure 21T:
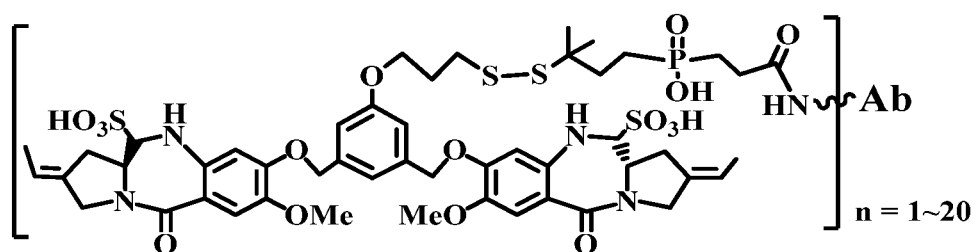
FIG. 21T. ADC structure of a pyrrolobenzodiazepine (tomaymycin) dimer prodrug through a charged linker (disulfide bond linkage).
Figure 21U:
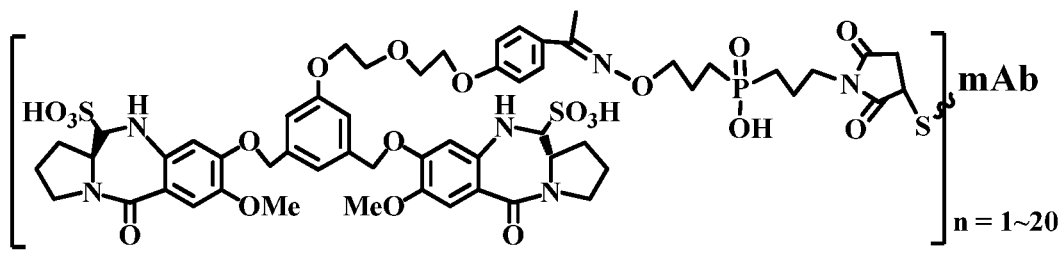
FIG. 21U. ADC structure of a pyrrolobenzodiazepine dimer prodrug through a charged linker (alkoxime bond linkage).
Figure 21V:
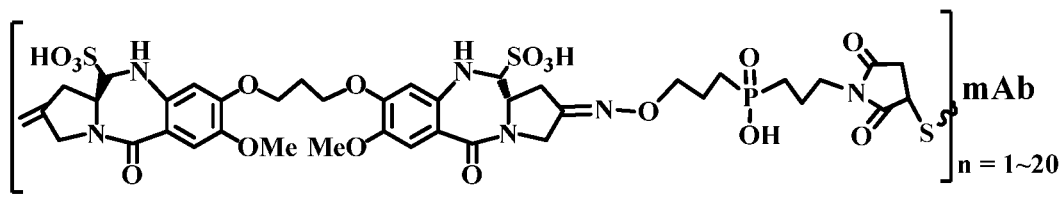
FIG. 21V. ADC structure of a pyrrolobenzodiazepine dimer prodrug through a charged linker (alkoxime bond linkage).
Figure 21W:
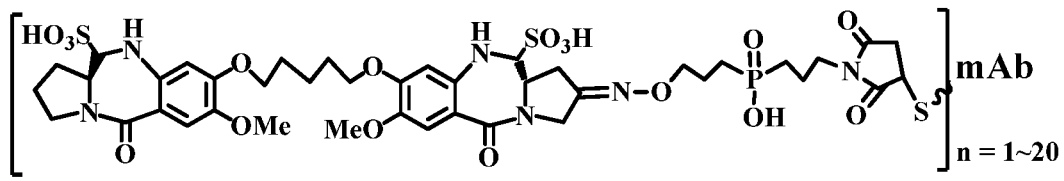
FIG. 21W. ADC structure of a pyrrolobenzodiazepine dimer prodrug through a charges linker (alkoxime bond linkage).
Figure 21X:
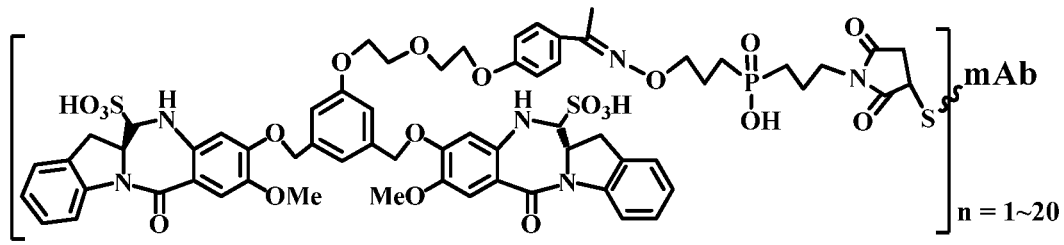
FIG. 21X, ADC structure of an indolinobenzodiazepine dimer prodrug through a charged linker (alkoxime bond linkage).
Figure 21Y:
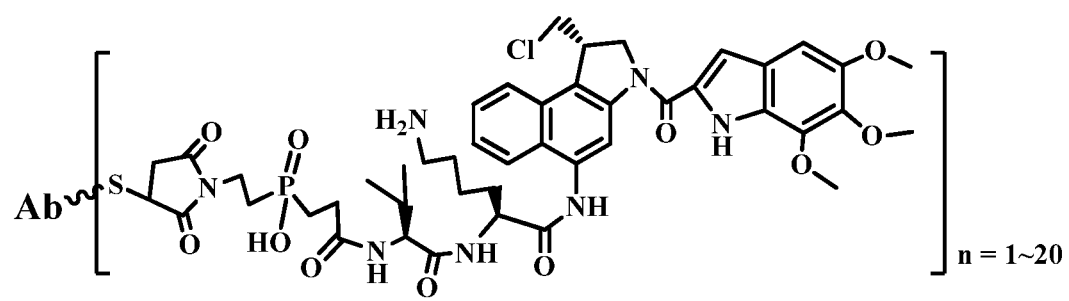

The synthesis of 2-dithio-pyridyl containing cross-linkers of formulae (I) is shown, for example, in FIGS. 1, 2, 4, 5, 6, 7, 8, 9, 10, 11, 13, and 14, and the synthesis of maleimido-containing charged cross linkers of the formula (I) is shown, for example, in FIGS. 3, and 12. The synthesis of polyethylene glycol-containing charged cross linkers of formula (I) is shown, for example, in FIG. 14. The synthesis of azide-containing charged cross linkers of formula (I) for Huisgen 1,3-dipolar cycloaddition of azides to alkynes is shown, for example, in FIG. 15. The synthesis of charged cross linkers of formula (I) bearing a hydrazide moiety enabling linkage via acid-labile bonds is shown, for example, in FIGS. 16, 17 and 18. The synthesis of charged cross linkers of formula (I) bearing an alkoxylamino moiety enabling linkage via alkoxime bonds is shown, for example, in FIG. 20.

Cell-Binding Agent Drug-Conjugates

The conjugates of the present invention can be represented by the following formula, $Cb-(-L-Drug)_n$, wherein Cb is a cell-binding agent, L is a charged phosphinate linker, Drug is a drug molecule, and n is an integer from 1 to 20.

The charged phosphinate linker L may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyl-oxycarbonyl ("PAB"), 4-thiopentanoate ("SPP"), 4-(N-maleimidomethyl)cyclohexane-1 carboxylate ("MCC"), (4-acetyl)aminobenzoate ("SIAB"), 4-thio-butyrate (SPDB), 4-thio-2-hydroxysulfonyl-butyrate (2-Sulfo-SPDB), ethyleneoxy —$CH_2CH_2O$— as one or more repeating units ("EO" or "PEO"). Additional linker components are known in the art and some are described herein.

Example structures of these components containing linkers are:

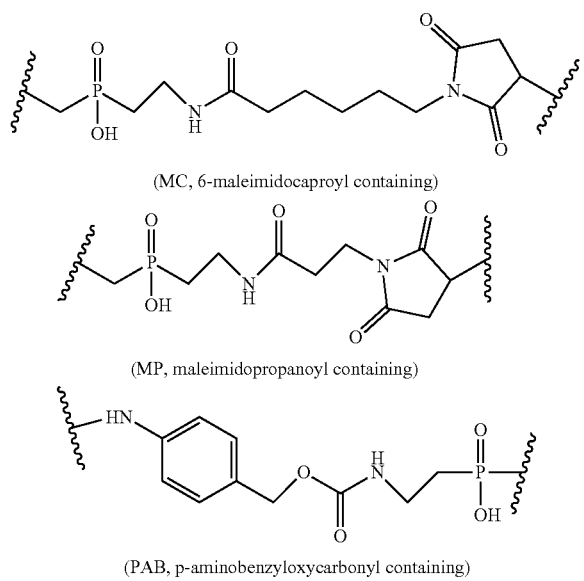

(MC, 6-maleimidocaproyl containing)

(MP, maleimidopropanoyl containing)

(PAB, p-aminobenzyloxycarbonyl containing)

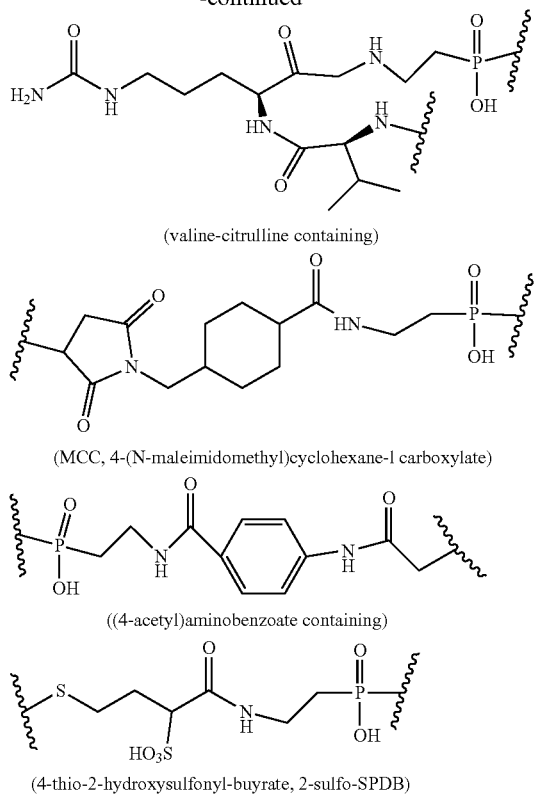

(valine-citrulline containing)

(MCC, 4-(N-maleimidomethyl)cyclohexane-1 carboxylate)

((4-acetyl)aminobenzoate containing)

(4-thio-2-hydroxysulfonyl-buyrate, 2-sulfo-SPDB)

Preferably, the conjugates have the following formula (II):

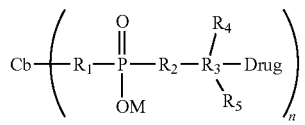

(II)

wherein:

Cb represents a cell-binding agent;

Drug represents the drug linked to the cell-binding agent via the hydrophilic linkers of this invention by a disulfide, thioether, thioester, peptide, hydrazone, ether, ester, carbamate, carbonate, heterocyclic ring, amine, imine, alkoxime or amide bond;

$R_1$, $R_2$, $R_3$, $R_4$, $R_5$, and M are described the same previously in formula (I).

As described in more detail below, the drug can be any of many small molecule drugs, including, but not limited to, tubulysins, calicheamicins, auristatins, maytansinoids, CC-1065 analogs, morpholinos doxorubicins, taxanes, cryptophycins, epothilones, and benzodiazepine dimers (e.g., dimmers of pyrrolobenzodiazepine (PBD) or tomaymycin), indolinobenzodiazepines, imidazobenzothiadiazepines, or oxazolidinobenzodiazepines).

To synthesize the conjugate, the cell-binding agent can be first modified with the crosslinkers of the present invention to introduce reactive disulfide groups, maleimido, haloacetyl or hydrazide groups. Synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl modified cell-binding agent and a drug containing a free thiol group. Synthesis of conjugates bearing an acid labile hydrazone link can be achieved by reaction of a carbonyl group with the hydrazide moiety in the linker, by methods known in the art (see, for example, P. Hamann et al., Hinman, L. M., et al, Cancer Res. 53, 3336-334, 1993; B. Laguzza et al., J. Med. Chem., 32; 548-555, 1959; P. Trail et al., Cancer Res., 57; 100-105, 1997).

Alternatively, the drug can be modified with the charged crosslinkers of the present invention to give a modified drug of formula (IV) bearing a functionality capable of reacting with a cell binding agent. For example a thiol-containing drug can be reacted with the charged crosslinker of formula (I) bearing a maleimdo substituent at neutral pH in aqueous buffer to give a drug connected to the charged linker via a thioether link. A thiol-containing drug can undergo disulfide exchange with a charged linker bearing a pyrdiyldithio moiety to give a modified drug attached via a disulfide bond to the charged crosslinker. A drug bearing a hydroxyl group or a thiol group can be reacted with a hydrophilic crosslinker bearing a halogen of this invention, in the presence of a mild base, to give a modified drug bearing an ether or thiol ether link. A hydroxyl group containing drug can be condensed with a charged crosslinker of formula (I) bearing a carboxyl group, in the presence of a dehydrating agent, such as EDC or dicyclohexylcarbodiimide, to give an ester link. An amino group containing drug can similarly undergo condensation with a carboxyl group on the charged crosslinker of formula (I) to give an amide bond.

The conjugate may be purified by standard biochemical means, such as gel filtration on a Sephadex G25 or Sephacryl 5300 column, adsorption chromatography, and ion exchange or by dialysis. In some cases (e.g. folic acid, melanocyte stimulating hormone, EGF etc) the cell-binding agent-drug conjugates can be purified by chromatography such as by HPLC, medium pressure column chromatography or ion exchange chromatography.

Modified Cell-Binding Agents

The cell-binding agent modified by reaction with crosslinkers of the present invention are preferably represented by the formula (III)

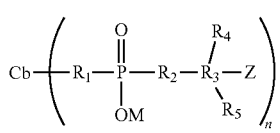

(III)

wherein the substituents are as described above for the charged linker and the cell-binding agent drug conjugate.

In preferred embodiments, Z is a disulfide substituent, a maleimido, haloacetyl group, or a N-hydroxy succinimide ester, and Cb linked with $R_1$ is through thioether, amide, or disulfide bond. The modified cell-binding agent can be prepared by reacting the cell-binding agent with the charged crosslinkers by methods known in the art for other crosslinkers (U.S. Pat. Nos. 5,846,545, 5,585,499, 5,475,092, 5,414,064, 5,208,020, and 4,563,304; J. Carlsson et al. Biochem. J. (1978) 173, 723-737(1978); Goff, D. A., Bio-Conjugate Chem. (1990), 1, 381-386; L. Delprino et al. J.

Pharm. Sci. (1993), 82, 506-512; S. Arpicco et al., *Bioconjugate Chem* (1997), 8, 327-337).

Advantageously, because the phosphinate groups are soluble in water or require only a small percentage of organic solvent to maintain solubility in aqueous solution, the reaction between the cell-binding agent and the cross-linker can be conducted in aqueous solution. The cross-linking reagent is dissolved in aqueous buffer, optionally containing a small amount (typically <10% by volume) of a polar organic solvent that is miscible with water, for example different alcohols, such as methanol, ethanol, and propanol, dimethyl formamide (DMF), dimethyl acetamide (DMA), or dimethylsulfoxide (DMSO) at a high concentration, for example 1-100 mM, and then an appropriate aliquot is added to the buffered aqueous solution of the cell-binding agent. An appropriate aliquot is an amount of solution that introduces 1-10 cross-linking groups per cell-binding agent, preferably 1-5 groups, and the volume to be added should not exceed 10%, preferably 5%, and most preferably 0-3% of the volume of the cell-binding agent solution. The aqueous solutions for the cell-binding agents are buffered between pH 6 and 9, preferably between 6.5 and 7.5 and can contain any non-nucleophilic buffer salts useful for these pH ranges. Typical buffers include phosphate, triethanolamine HCl, HEPES, and MOPS buffers, which can contain additional components, such as cyclodextrins, sucrose and salts, for example, NaCl. After the addition the reaction is incubated at a temperature of from 4° C. to 40° C., preferably at ambient temperature. The progress of the reaction can be monitored by measuring the increase in the absorption at 325 nm or another appropriate wavelength. After the reaction is complete, isolation of the modified cell-binding agent can be performed in a routine way, using for example gel filtration chromatography, or adsorptive chromatography.

Figure 22:
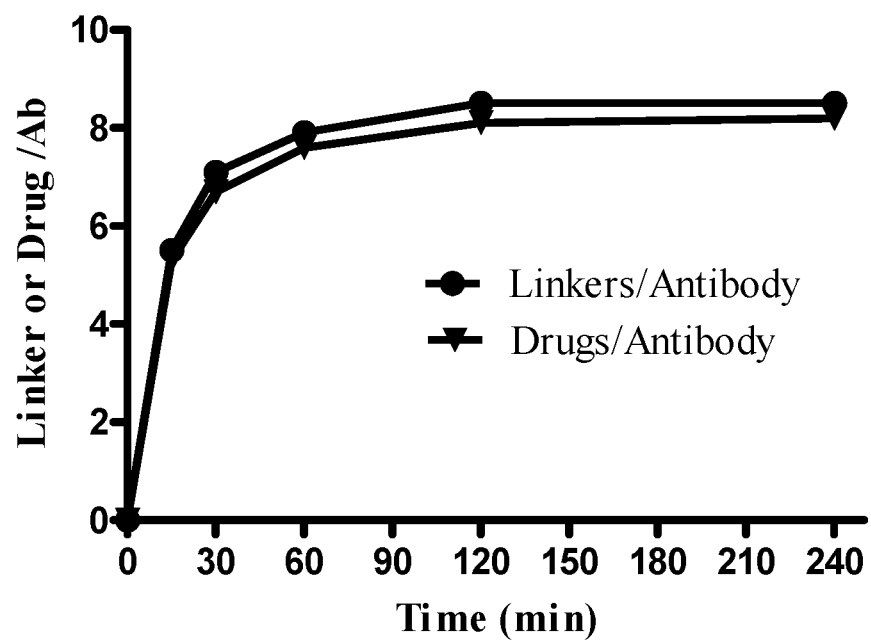
FIG. 22 shows the use of a charged phosphinate linker in modifying a cell-binding agent (antiHer2 antibody) and producing a cell-binding agent-drug conjugate containing the charged phosphinate linker.
Figure 23:
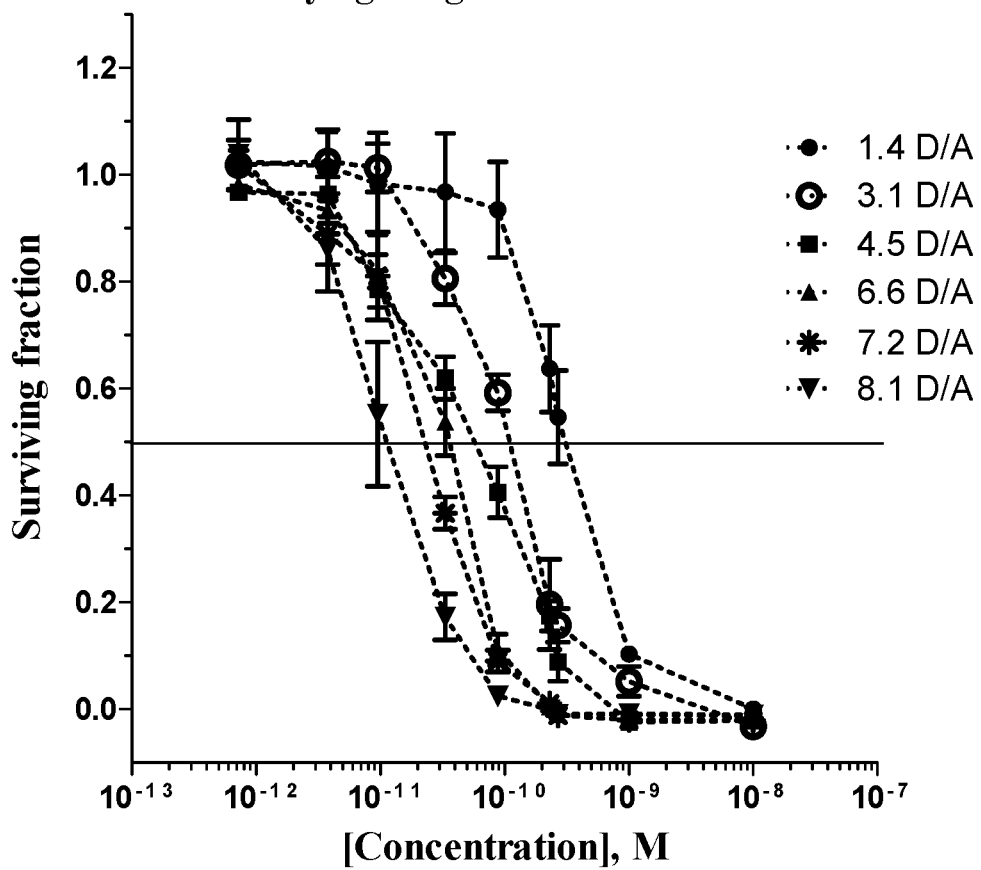
FIG. 23 shows the in vito assays of the cytotoxicity of the antiCD22-TZ041 conjugate with different drug load ratios via a phosphinate linker.
Figure 23:
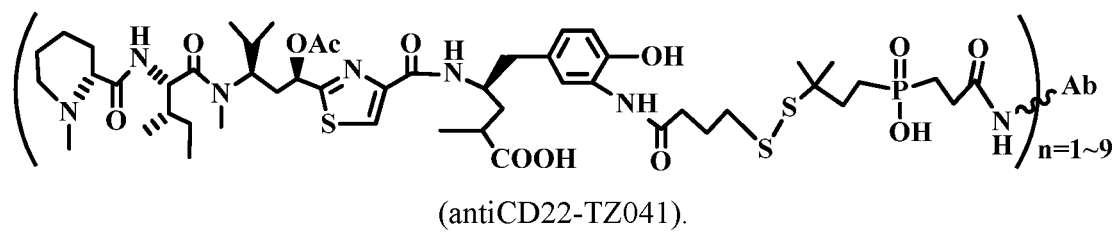

The extent of modification can be assessed by measuring the absorbance of the nitropyridine thione, dinitropyridine dithione, carboxamidopyridine dithione or dicarboxamidopyridine dithione group released. FIG. 22 shows the results from the modification of the cell-binding agent, the her2 antibody, with a charged crosslinker of the present invention. The time course of linker/antibody (L/A) incorporation is shown, for example, along with the drugs/antibody (D/A) linked. The charged crosslinkers described herein have diverse functional groups that can react with any cell-binding agent that possesses a suitable substituent. For example cell-binding agents bearing an amino or hydroxyl substituent can react with crosslinkers bearing an N-hydroxysuccinimide (NHS) ester, cell-binding agents bearing a thiol substituent can react with crosslinkers bearing a maleimido or haloacetyl group. Additionally, cell-binding agents bearing a carbonyl substituent can react with crosslinkers bearing a hydrazide. One skilled in the art can readily determine which crosslinker to use based on the known reactivity of the available functional group on the cell-binding agent.

Modified Cytotoxic Drugs

The cytotoxic drugs modified by reaction with crosslinkers of the present invention are preferably represented by the formula (IV):

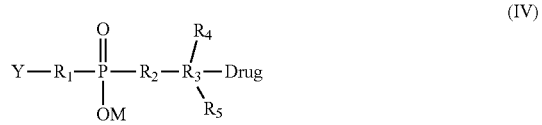

(IV)

wherein the substituents are as defined above.

In preferred embodiments, Y is a disulfide substituent, a maleimido, haloacetyl group, or a N-hydroxy succinimide ester.

The modified drugs can be prepared by reacting the drug with the crosslinkers of the present invention to give a modified drug of formula (IV) bearing a functionality capable of reacting with a cell binding agent. For example a thiol-containing drug can be reacted with the crosslinker of formula (I) bearing a maleimdo substituent at neutral pH in aqueous buffer to give a drug connected to the charged linker via a thioether link. A thiol-containing drug can undergo disulfide exchange with a hydrophilic linker bearing a pyrdiyldithio moiety to give a modified drug attached via a disulfide bond to the charged crosslinker. A drug bearing a hydroxyl group can be reacted with a crosslinker bearing a halogen, in the presence of a mild base, to give a modified drug bearing an ether link. A hydroxyl group containing drug can be condensed with a crosslinker of formula (I) bearing a carboxyl group, in the presence of a dehydrating agent, such as dicyclohexylcarbodimide, to give an ester link. An amino group containing drug can similarly undergo condensation with a carboxyl group on the charged crosslinker of formula (I) to give an amide bond. The modified drug can be purified by standard methods such as column chromatography over silica gel or alumina, crystallization, preparatory thin layer chromatography, ion exchange chromatography or HPLC.

Cell-Binding Agents

The cell-binding molecule that comprises the conjugates and the modified cell-binding agents of the present invention may be of any kind presently known, or that become known, molecule that binds to, complexes with or reacts with a moiety of a cell population sought to be therapeutically or otherwise biologically modified.

The cell binding agents include, but are not limited to, large molecular weight proteins such as, for example, full-length antibodies (polyconal antibodies, monoclonal antibodies, dimers, multimers, multispecific antibodies (e.g., bispecific antibodies); single chain antibodies; fragments of antibodies such as Fab, Fab', F(ab')$_2$, F$_v$, [Parham, J. Immunol. 131, 2895-2902 (1983)], fragments produced by a Fab expression library, anti-idiotypic (anti-Id) antibodies, CDR's, and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) Jour. of Immunology 170:4854-4861); interferons (such as type I, II, III); peptides; lymphokines such as IL-2, IL-3, IL-4, IL-6, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, polypeptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin {O'Keefe et al, 260 J. Biol. Chem. 932-937 (1985)}; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93). In general monoclonal antibodies are preferred as a cell-surface binding agent if an appropriate one is available. And antibodies may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). *Nature* 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after Protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8:396 (1959)) supplemented with 4.5 gm/l glucose, 20 mm glutamine, 20% fetal calf serum and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451, 570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989).

Moncolonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859, 205 and 6,797,492; Liu et al, Immunol Rev. 222:9-27 (2008); Almagro et al, Front Biosci. 1; 13:1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix, Inc.), the HuMAb-Mouse (Medarex/BMS), the VelociMouse (Regeneron), see also U.S. Pat. Nos. 6,596, 541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26:39-60 (2004); Houdebine, Curr Opin Biotechnol. 13:625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3:964-70, (2002)); Adams et al, J Immunol Methods. 231:249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 2003; 23(4):307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, as long as such attachment permits the peptide or protein to retain its antigen binding specificity.

Examples of antibodies used for conjugation of drugs via the hydrophilic linkers of this prevention for treating cancer, autoimmune disease, and infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (α chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta_3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (α chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (antialpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $\alpha_4\beta_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.285 [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TR$\alpha\beta$ (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, N.J.), Smart ID10 (Protein Design Labs), Oncolym (Techniclone Inc, Calif.), Allomune (BioTransplant, Calif.), anti-VEGF (Genentech, Calif.); CEAcide (Immunomedics, N.J.), IMC-1C11 (ImClone Systems, N.J.) and Cetuximab (Im-Clone, N.J.).

Other antibodies as binding ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 ($\Delta$-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v\beta 3$, $\alpha 5\beta 1$, $\alpha 6\beta 4$, $\alpha 11\beta 3$, $\alpha 5\beta 5$, $\alpha v\beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76). Examples of these antigens that antibodies against are: Many other Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Annexin A1, Nucleolin, Endoglin (CD105), ROBO4, Amino-peptidase N, □-like-4 (DLL4), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 nonmutant, NY-ESO-1, GD2, CEA, MelanA/MART1, Ras mutant, gp100, p53 mutant, Proteinase3 (PR1), bcr-abl, Tyrosinase, Survivin, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, Fos-related antigen 1.

In another specific embodiment, the cell-binding-drug conjugates via the hydrophilic likers of this invention are used for the treatment of cancers. The cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates via the hydrophilic likers of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Anti synthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjogren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the hydrophilic linkers of this invention for the treatment or prevention of an autoimmune disease includes, but is not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial (M2) antibody; Rheumatoid factor antibody; Anti-MCV antibody; Anti-topoisomerase antibody; Anti-neutrophil cytoplasmic (cANCA) antibody;

In certain preferred embodiments, the binding molecule for the conjugate in the present invention, can bind to both a receptor or a receptor complex expressed on an activated lymphocyte which is associated with an autoimmune disease. The receptor or receptor complex can comprise an immunoglobulin gene superfamily member (e.g. CD2, CD3, CD4, CD8, CD19, CD22, CD28, CD79, CD90, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized IgG1 antibody for the treatment of cytomegalovirus; and anti-LPS antibodies.

The cell binding molecules-drug conjugates via the hydrophilic linkers of this invention can be used in the treatment of infectious diseases. These infectious diseases include, but are not limited to, Acinetobacter infections, Actinomycosis, African sleeping sickness (African trypanosomiasis), AIDS (Acquired immune deficiency syndrome), Amebiasis, Anaplasmosis, Anthrax, Arcanobacterium haemolyticum infection, Argentine hemorrhagic fever, Ascariasis, Aspergillosis, Astrovirus infection, Babesiosis, Bacillus cereus infection, Bacterial pneumonia, Bacterial vaginosis, Bacteroides infection, Balantidiasis, Baylisascaris infection, BK virus infection, Black piedra, Blastocystis hominis infection, Blastomycosis, Bolivian hemorrhagic fever, Borrelia infection, Botulism (and Infant botulism), Brazilian hemorrhagic fever, Brucellosis, Burkholderia infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chlamydia, Chlamydophila pneumoniae infection, Cholera, Chromoblastomycosis, Clonorchiasis, Clostridium difficile infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by Clostridium perfringens, Free-living amebic infection, Fusobacterium infection, Gas gangrene (Clostridial myonecrosis), Geotrichosis, Gerstmann-Straussler-Scheinker syndrome, Giardiasis, Glanders, Gnathostomiasis, Gonorrhea, Granuloma inguinale (Donovanosis), Group A streptococcal infection, Group B streptococcal infection, Haemophilus influenzae infection, Hand, foot and mouth disease (HFMD), Hantavirus Pulmonary Syndrome, Helicobacter pylori infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), Mycoplasma pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, Pneumocystis pneumonia, Pneumonia, Poliomyelitis, Prevotella infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever, Rocky mountain spotted fever, Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, Ureaplasma urealyticum infection, Venezuelan equine encephalitis, Venezuelan hemorrhagic fever, Viral pneumonia, West Nile Fever, White piedra (Tinea blanca), Yersinia pseudotuberculosis infection, Yersiniosis, Yellow fever, Zygomycosis.

The cell binding molecules, which are more proffered to be antibodies described in this patent that are against pathogenic strains include, but are not limit, Acinetobacter baumannii, Actinomyces israelii, Actinomyces gerencseriae and Propionibacterium propionicus, Trypanosoma brucei, HIV (Human immunodeficiency virus), Entamoeba histolytica, *Anaplasma* genus, Bacillus anthracis, Arcanobacterium haemolyticum, Junin virus, Ascaris lumbricoides, *Aspergillus* genus, Astroviridae family, *Babesia* genus, Bacillus cereus, multiple bacteria, *Bacteroides* genus, Balantidium coli, *Baylisascaris* genus, BK virus, Piedraia hortae, Blastocystis hominis, Blastomyces dermatitides, Machupo virus, *Borrelia* genus, Clostridium botulinum, Sabia, *Brucella* genus, usually Burkholderia cepacia and other *Burkholderia* species, Mycobacterium ulcerans, Caliciviridae family, *Campylobacter* genus, usually Candida albicans and other *Candida* species, Bartonella henselae, Group A Streptococcus and Staphylococcus, Trypanosoma cruzi, Haemophilus ducreyi, Varicella zoster virus (VZV), Chlamydia trachomatis, Chlamydophila pneumoniae, Vibrio cholerae, Fonsecaea pedrosoi, Clonorchis sinensis, Clostridium difficile, Coccidioides immitis and Coccidioides posadasii, Colorado tick fever virus, rhinoviruses, coronaviruses, CJD prion, Crimean-Congo hemorrhagic fever virus, Cryptococcus neoformans, *Cryptosporidium* genus, Ancylostoma braziliense; multiple parasites, Cyclospora cayetanensis, Taenia solium, Cytomegalovirus, Dengue viruses (DEN-1, DEN-2, DEN-3 and DEN-4)—Flaviviruses, Dientamoeba fragilis, Corynebacterium diphtheriae, Diphyllobothrium, Dracunculus medinensis, Ebolavirus, *Echinococcus* genus, *Ehrlichia* genus, Enterobius vermicularis, *Enterococcus* genus, *Enterovirus* genus, Rickettsia prowazekii, Parvovirus B19, Human herpesvirus 6 and Human herpesvirus 7, Fasciolopsis buski, Fasciola hepatica and Fasciola gigantica, FFI prion, Filarioidea superfamily, Clostridium perfringens, *Fusobacterium* genus, Clostridium perfringens; other *Clostridium* species, Geotrichum candidum, GSS prion, Giardia intestinalis, Burkholderia mallei, Gnathostoma spinigerum and Gnathostoma hispidum, Neisseria gonorrhoeae, Klebsiella granulomatis, Streptococcus pyogenes, Streptococcus agalactiae, Haemophilus influenzae, Enteroviruses, mainly Coxsackie A virus and Enterovirus 71, Sin Nombre virus, Helicobacter pylori, Escherichia coli O157: H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, Histoplasma capsulatum, Ancylostoma duodenale and Necator americanus, Hemophilus influenzae, Human bocavirus, Ehrlichia ewingii, Anaplasma phagocytophilum, Human metapneumovirus, Ehrlichia chaffeensis, Human papillomavirus, Human parainfluenza viruses, Hymenolepis nana and Hymenolepis diminuta, Epstein-Barr Virus, Orthomyxoviridae family, Isospora belli, Kingella kingae, Klebsiella pneumoniae, Klebsiella ozaenas, Klebsiella rhinoscleromotis, Kuru prion, Lassa virus, Legionella pneumophila, Legionella pneumophila, *Leishmania* genus, Mycobacterium leprae and Mycobacterium lepromatosis, *Leptospira* genus, Listeria monocytogenes, Borrelia burgdorferi and other *Borrelia* species, Wuchereria bancrofti and Brugia malayi, Lymphocytic choriomeningitis virus (LCMV), *Plasmodium* genus, Marburg virus, Measles virus, Burkholderia pseudomallei, Neisseria meningitides, Metagonimus yokagawai, Microsporidia phylum, Molluscum contagiosum virus (MCV), Mumps virus, Rickettsia typhi, Mycoplasma pneumoniae, numerous species of bacteria (Actinomycetoma) and fungi (Eumycetoma), parasitic dipterous fly larvae, Chlamydia trachomatis and Neisseria gonorrhoeae, vCJD prion, Nocardia asteroides and other Nocardia species, Onchocerca volvulus, Paracoccidioides brasiliensis, Paragonimus westermani and other *Paragonimus* species, *Pasteurella* genus, Pediculus humanus capitis, Pediculus humanus corporis, Phthirus pubis, Bordetella pertussis, Yersinia pestis, Streptococcus pneumoniae, Pneumocystis jirovecii, Poliovirus, Prevotella genus, Naegleria fowleri, JC virus, Chlamydophila psittaci, Coxiella burnetii, Rabies virus, Streptobacillus moniliformis and Spirillum minus, Respiratory syncytial virus, Rhinosporidium seeberi, Rhinovirus, *Rickettsia* genus, Rickettsia akari, Rift Valley fever virus, Rickettsia rickettsii, Rotavirus, Rubella virus, *Salmonella* genus, SARS coronavirus, Sarcoptes scabiei, *Schistosoma* genus, *Shigella* genus, Varicella zoster virus, Variola major or Variola minor, Sporothrix schenckii, *Staphylococcus* genus, *Staphylococcus* genus, Staphylococcus aureus, Streptococcus pyogenes, Strongyloides stercoralis, Treponema pallidum, Taenia genus, Clostridium tetani, *Trichophyton* genus, Trichophyton tonsurans, *Trichophyton* genus, Epidermophyton floccosum, Trichophyton rubrum, and Trichophyton mentagrophytes, Trichophyton rubrum, Hortaea werneckii, *Trichophyton* genus, *Malassezia* genus, Toxocara canis or Toxocara cati, Toxoplasma gondii, Trichinella spiralis, Trichomonas vaginalis, Trichuris trichiura, Mycobacterium tuberculosis, Francisella tularensis, Ureaplasma urealyticum, Venezuelan equine encephalitis virus, Vibrio colerae, Guanarito virus, West Nile virus, Trichosporon beigelii, Yersinia pseudotuberculosis, Yersinia enterocolitica, Yellow fever virus, Mucorales order (Mucormycosis) and Entomophthorales order (Entomophthoramycosis), Pseudomonas aeruginosa, Campylobacter (Vibrio) fetus, Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, *Mycoplasma* spp., Rickettsia prowazeki, Rickettsia tsutsugumushi, *Clamydia* spp.; pathogenic fungi (Aspergillus fumigatus, Candida albicans, Histoplasma capsulatum); protozoa (Entomoeba histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria); or Helminiths (Schistosoma japonicum, Schistosoma mansoni, Schistosoma haematobium, and hookworms).

Other antibodies as cell binding ligands used in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate via the hydrophilic linkers of the invention together with a pharmaceutically acceptable carrier for treatment of cancer and autoimmune disorders. The method for treatment of cancer and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate via the linkers of the invention will be supplied as solutions or as a lyophilized solid that can be redissolved in sterile water for injection. Examples of suitable protocols of conjugate administration are as follows. Conjugates are given weekly for 8 weeks as an i.v. bolus. Bolus doses are given in 50 to 500 ml of normal saline to which human serum albumin (e.g. 0.5 to 1 mL of a concentrated solution of human serum albumin, 100 mg/mL) can be added. Dosages will be about 50 µg to 20 mg/kg of body weight per week, i.v. (range of 10 µg to 200 mg/kg per injection). 8 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the linkers of this invention may be provided in an aqueous physiological buffer solution containing 0.1 to 10% w/v conjugates for parenteral administration. Typical dose ranges are from 1 µg/kg to 0.1 g/kg of body weight per day; a preferred dose range is from 0.01 mg/kg to 20 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 1 to 500 mg administered one to four times a day, and even more preferably from 10 mg to 500 mg, once a day. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via transdermal patches.

Drugs/Cytotoxic Agents

Drugs that can be conjugated to a cell-binding molecule in the present invention are small molecule drugs including cytotoxic agents, which can be linked to or after they are modified for linkage to the cell-binding agent. A "small molecule drug" is broadly used herein to refer to an organic, inorganic, or organometallic compound that may have a molecular weight of for example 100 to 1800, more suitably from 120 to 1400. Small molecule drugs are well characterized in the art, such as in WO05058367A2, and in U.S. Pat. No. 4,956,303, among others and are incorporated in their entirety by reference. The drugs includes known drugs and those that may become known drugs.

Drugs that are known include, but not limited to, 1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); duocarmycin (including the synthetic analogues, KW-2189 and CBI-TMI); benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkyl sulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine]; b). Plant Alkaloids: such as Vinca alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BMW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). antibiotics, such as the enediyne antibiotics (e.g. calicheamicins, especially calicheamicin .γ1, δ1, α1 and β1, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; f). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Antiadrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; l). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethylpenicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides &_nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The drugs used for conjugates via a charged linker of the present invention also include radioisotopes. Examples of radioisotopes (radionuclides) are $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labeled antibodies are useful in receptor targeted imaging experiments or can be for targeted treatment such as with the antibody-drug conjugates of the invention (Wu et al (2005) Nature Biotechnology 23(9): 1137-1146). The cell binding molecules, e.g. an antibody can be labeled with ligand reagents through the charged linkers of the present patent that bind, chelate or otherwise complex a radioisotope metal, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.).

6). The pharmaceutically acceptable salts, acids or derivatives of any of the above drugs.

Preferred cytotoxic agents that conjugated to a cell-binding molecule via a charged linker of this patent are tubulusins, maytansinoids, taxanoids (taxanes), CC-1065 analogs, daunorubicin and doxorubicin compounds, benzodiazepine dimers (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotics, actinomycin, azaserines, bleomycins, epirubicin, tamoxifen, idarubicin, dolastatins/auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristine, hemiasterlins, esperamicins, and their analogues and derivatives thereof.

Tubulysins that are preferred for conjugation in the present invention are well known in the art and can be isolated from natural sources according to known methods or prepared synthetically according to known methods (e. g. Balasubramanian, R.; et al. *J. Med. Chem.*, 2009, 52, 238-240. Wipf, P.; et al. *Org. Lett.*, 2004, 6, 4057-4060. Pando, O.; et al. *J. Am. Chem. Soc.*, 2011, 133, 7692-7695. Reddy, J. A.; et al. *Mol. Pharmaceutics*, 2009, 6, 1518 1525. Raghavan, B.; et al. *J. Med. Chem.*, 2008, 51, 1530-1533. Patterson, A. W.; et al. *J. Org. Chem.*, 2008, 73, 4362-4369. Pando, O.; et al. *Org. Lett.*, 2009, 11 (24), pp 5567-5569. Wipf, P.; et al. *Org. Lett.*, 2007, 9 (8), 1605-1607. Friestad, G. K.; *Org. Lett.*, 2004, 6, pp 3249-3252. Hillary M. Peltier, H. M.; et al. *J. Am. Chem. Soc.*, 2006, 128, 16018-16019. Chandrasekhar, S.; et al. *J. Org. Chem.*, 2009, 74, 9531-9534. Liu, Y.; et al. *Mol. Pharmaceutics*, 2012, 9, 168-175. Friestad, G. K.; et al. *Org. Lett.*, 2009, 11, 1095-1098. Kubicek, K.; et al., Angew Chem Int Ed Engl, 2010. 49: p. 4809-12. Chai, Y.; et al., Chem Biol, 2010, 17: 296-309. Ullrich, A.; et al., Angew Chem Int Ed Engl, 2009, 48, 4422-5. Sani, M.; et al. Angew Chem Int Ed Engl, 2007, 46, 3526-9. Domling, A.; et al., Angew Chem Int Ed Engl, 2006. 45, 7235-9. Patent applications: Zanda, M.; et al., Can. Pat. Appl. CA 2710693 (2011). Chai, Y.; et al. Eur. Pat. Appl. 2174947 (2010), PCT WO 2010034724. Leamon, C.; et al, PCT WO 2010033733, WO 2009002993. Ellman, J.; et al, PCT WO 2009134279; PCT WO 2009012958, U.S. appl. 20110263650, 20110021568, Matschiner, G.; et al, PCT WO 2009095447.Vlahov, I.; et al, PCT WO 2009055562, WO 2008112873. Low, P.; et al, PCT WO 2009026177. Richter, W., PCT WO 2008138561. Kjems, J.; et al, PCT WO 2008125116. Davis, M.; et al, PCT WO 2008076333. Diener, J.; et al, U.S. Pat. Appl. 20070041901, WO 2006096754. Matschiner, G.; et al, PCT WO 2006056464. Vaghefi, F.; et al, 5 PCT WO 2006033913. Doemling, A., Ger. Offen. DE 102004030227; PCT WO 2004005327; WO 2004005326; WO2004005269. Stanton, M.; et al, U.S. Pat. Appl. Publ. 20040249130. Hoefle, G.; et al, Ger. Offen. DE 10254439; DE 10241152; DE 10008089. Leung, D.; et al, PCT WO 2002077036. Reichenbach, H.; et al, Ger. Offen. DE 19638870; Wolfgang, R.; U.S. 20120129779, Chen, H., U.S. appl. 20110027274. The preferred structure of tubulysins for conjugation of cell binding molecules are described in the patent application of PCT/IB2012/053554

Calicheamicins and their related enediyne antibiotics that are preferred for cell-binding molecule-drug conjugates of this patent are described in: Nicolaou, K. C. et al, Science 1992, 256, 1172-1178; Proc. Natl. Acad. Sci USA. 1993, 90, 5881-5888), U.S. Pat. Nos. 4,970,198; 5,053,394; 5,108, 912; 5,264,586; 5,384,412; 5,606,040; 5,712,374; 5,714, 586; 5,739,116; 5,770,701; 5,770,710; 5,773,001; 5,877, 296; 6,015,562; 6,124,310; 8,153,768.

Maytansinoids that are preferred to be used in the present invention including maytansinol and maytansinol analogues are described in U.S. Pat. Nos. 4,256,746, 4,361,650 and 4,307,016, 4,294,757, 4,294,757, 4,371,533, 4,424,219, 4,331,598, 4,450,254, 4,364,866, 4,313,946, 4,315,929 4,362,663, 4,322,348, 4,371,533, 4,424,219, 5,208,020, 5,416,064, 5,208,020; 5,416,064; 6,333.410; 6,441,163; 6,716,821, 7,276,497, 7,301,019, 7,303,749, 7,368,565, 7,411,063, 7,851,432, 8,163,888.

Taxanes, which includes Paclitaxel (Taxol), a cytotoxic natural product, and docetaxel (Taxotere), a semi-synthetic derivative, and their analogs which are preferred for conjugation via the charged linkers of the present patent are exampled in: K C. Nicolaou et al., J. Am. Chem. Soc. 117, 2409-2420, (1995); Ojima et al, *J. Med. Chem.* 39:3889-3896 (1996); 40:267-278 (1997); 45, 5620-5623 (2002); Ojima et al., *Proc. Natl. Acad. Sci.*, 96:4256-4261 (1999); Kim et al., Bull. Korean Chem. Soc., 20, 1389-1390 (1999); Miller, et al. J. Med. Chem., 47, 4802-4805(2004); U.S. Pat. Nos. 5,475,011 5,728,849, 5,811,452; 6,340,701; 6,372,738; 6,391,913, 6,436,931; 6,589,979; 6,596,757; 6,706,708; 7,008,942; 7,186,851; 7,217,819; 7,276,499; 7,598,290; 7,667,054.

CC-1065 analogues and doucarmycin analogs are also preferred to be used for a conjugate with the charged linker of the present patent. The examples of the CC-1065 analogues and doucarmycin analogs as well as their synthesis are described in: e.g. Warpehoski et al, *J. Med. Chem.* 31:590-603 (1988), D. Boger et al., *J. Org. Chem;* 66; 6654-6661, 2001; U.S. Pat. Nos. 4,169,888, 4,391,904, 4,671,958, 4,816,567, 4,912,227, 4,923,990, 4,952,394, 4,975,278, 4,978,757, 4,994,578, 5,037,993, 5,070,092, 5,084,468, 5,101,038, 5,117,006, 5,137,877, 5,138,059, 5,147,786, 5,187,186, 5,223,409, 5,225,539, 5,288,514, 5,324,483, 5,332,740, 5,332,837, 5,334,528, 5,403,484, 5,427,908, 5,475,092, 5,495,009, 5,530,101, 5,545,806, 5,547,667, 5,569,825, 5,571,698, 5,573,922, 5,580,717, 5,585,089, 5,585,499, 5,587,161, 5,595,499, 5,606,017, 5,622,929, 5,625,126, 5,629,430, 5,633,425, 5,641,780, 5,660,829, 5,661,016, 5,686,237, 5,693,762, 5,703,080, 5,712,374, 5,714,586, 5,739,116, 5,739,350, 5,770,429, 5,773,001, 5,773,435, 5,786,377 5,786,486, 5,789,650, 5,814,318, 5,846,545, 5,874,299, 5,877,296, 5,877,397, 5,885,793, 5,939,598, 5,962,216, 5,969,108, 5,985,908, 6,060,608, 6,066,742, 6,075,181, 6,103,236, 6,114,598, 6,130,237, 6,132,722, 6,143,901, 6,150,584, 6,162,963, 6,172,197, 6,180,370, 6,1946,12, 6,214,345, 6,262,271, 6,281,354, 6,310,209, 6,329,497, 6,342,480, 6,486,326, 6,512,101, 6,521,404, 6,534,660, 6,544,731, 6,548,530, 6,555,313, 6,555,693, 6,566,336, 6,586,618, 6,593,081, 6,630,579, 6,756,397, 6,759,509, 6,762,179, 6,884,869, 6,897,034, 6,946,455, 7,049,316, 7,087,600, 7,091,186, 7,115,573, 7,129,261, 7,214,663, 7,223,837, 7,304,032, 7,329,507, 7,329,760, 7,388,026, 7,655,660, 7,655,661, 7,906,545, 8,012,978.

Daunorubicin/Doxorubicin Analogues are also preferred for conjugation via the charged linker of the present patent. The preferred structures and their synthesis are exampled in: Hurwitz, E., et al., Cancer Res. 35, 1175-1181 (1975). Yang, H. M., and Reisfeld, R. A., Proc. Natl. Acad. Sci. 85, 1189-1193 (1988); Pietersz, C. A., E., et al., E., et al.," Cancer Res. 48, 926-9311 (1988); Trouet, et al., 79, 626-629 (1982); Z. Brich et al., J. Controlled Release, 19, 245-258 (1992); Chen et al., Syn. Comm., 33, 2377-2390, 2003; King et al., Bioconj. Chem., 10, 279-288, 1999; King et al., J. Med. Chem., 45, 4336-4343, 2002; Kratz et al., J Med Chem. 45, 5523-33. 2002; Kratz et al., Biol Pharm Bull. Jan. 21, 56-61, 1998; Lau et al., Bioorg. Med. Chem. 3, 1305-1312, 1995; Scott et al., Bioorg. Med. l Chem. Lett. 6, 1491-1496; 1996; Watanabe et al., Tokai J. Experimental Clin. Med. 15, 327-334, 1990; Zhou et al., J. Am. Chem. Soc. 126, 15656-7, 2004; WO 01/38318; U.S. Pat. Nos. 5,106,951; 5,122,368; 5,146,064; 5,177,016; 5,208,323; 5,824,805; 6,146,658; 6,214,345; 7569358; 7,803,903; 8,084,586; 8,053,205.

Auristatins and dolastatins are preferred in conjugation via the charged linker of this patent. The auristatins (e. g. auristain E (AE) auristatin EB (AEB), auristatin EFP (AEFP), monomethyl auristatin E (MMAE), Monomethyl-auristatin (MMAF), Auristatin F phenylene diamine (AFP) and a phenylalanine variant of MMAE) which are synthetic analogs of dolastatins, are described in Int. J. Oncol. 15:367-72 (1999); Molecular Cancer Therapeutics, vol. 3, No. 8, pp. 921-932 (2004); U.S. Application Nos. 2011134826, 20060074008, 2006022925. U.S. Pat. Nos. 4,414,205, 4,753,894, 4,764,368, 4,816,444, 4,879,278, 4,943,628, 4,978,744, 5,122,368, 5,165,923, 5,169,774, 5,286,637, 5,410,024, 5,521,284, 5,530,097, 5,554,725, 5,585,089, 5,599,902, 5,629,197, 5,635,483, 5,654,399, 5,663,149, 5,665,860, 5,708,146, 5,714,586, 5,741,892, 5,767,236, 5,767,237, 5,780,588, 5,821,337, 5,840,699, 5,965,537, 6,004,934, 6,033,876, 6,034,065, 6,048,720, 6,054,297, 6,054,561, 6,124,431, 6,1437,21, 6,162,930, 6,214,345, 6,239,104, 6,323,315, 6,342,219, 6,342,221, 6,407,213, 6,569,834, 6,620,911, 6,639,055, 6,884,869, 6,913,748, 7,090,843, 7,091,186, 7,097,840, 7,098,305, 7,098,308, 7,498,298, 7,375,078, 7,462,352, 7,553,816, 7,659,241, 7,6623,87, 7,745,394, 7,754,681, 7,829,531, 7,837,980, 7,837,995, 7,902,338, 7,964,566, 7,964,567, 7,851,437, 7,994,135.

The benzodiazepine dimers (e. g. dimmers of pyrroloben-zodiazepine (PBD) or (tomaymycin), indolinobenzodiaz-epines, imidazobenzothiadiazepines, or oxazolidinobenzo-diazepines) which are preferred cytotoxic agents according to the present invention are exampled in the art: U.S. Pat. Nos. 8,163,736; 8,153,627; 8,034,808; 7,834,005; 7,741,319; 7,704,924; 7,691,848; 7,678,787; 7,612,062; 7,608,615; 7,557,099; 7,528,128; 7,528,126; 7,511,032; 7,429,658; 7,407,951; 7,326,700; 7,312,210; 7,265,105; 7,202, 239; 7,189,710; 7,173,026; 7,109,193; 7,067,511; 7,064, 120; 7,056,913; 7,049,311; 7,022,699; 7,015,215; 6,979, 684; 6,951,853; 6,884,799; 6,800,622; 6,747,144; 6,660, 856; 6,608,192; 6,562,806; 6,977,254; 6,951,853; 6,909, 006; 6,344,451; 5,880,122; 4,935,362; 4,764,616; 4,761, 412; 4,723,007; 4,723,003; 4,683,230; 4,663,453; 4,508, 647; 4,464,467; 4,427,587; 4,000,304; U.S. patent appl. 20100203007, 20100316656, 20030195196.

Analogues and derivatives of the cytotoxic drugs/agents described in the present patent can be conjugated via a charged linker of the present patent. One skilled in the art of drugs/cytotoxic agents will readily understand that each of the drugs/cytotoxic agents described herein can be modified in such a manner that the resulting compound still retains the specificity and/or activity of the starting compound. The skilled artisan will also understand that many of these compounds can be used in place of the drugs/cytotoxic agents described herein. Thus, the drugs/cytotoxic agents of the present invention include analogues and derivatives of the compounds described herein.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. NMR spectra were recorded on Varian Mercury 300 MHz Instrument. Chemical shifts (.delta.) are reported in parts per million (ppm) referenced to tetramethylsilane at 0.00 and coupling constants (J) are reported in Hz. Low resolution mass spectral data were acquired on a Waters Micromass ZMD mass spec with Waters 2795 HPLC separations module and the 2996 photodiode array detector.

Example 1. (2-Bromoethyl)(3-ethoxy-3-oxopropyl) phosphinic acid (or ethyl 3-[2-Bromoethyl(hydroxy) phosphinyl]propanoate) (4)

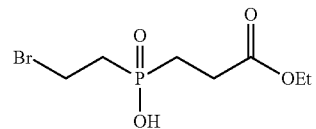 [SMILES: CCOC(=O)CCP(=O)(O)CCBr]

A mixture of ammonium hypophosphite (8.00 g, 96 mmol) and hexamethydisilazane (20.0 mL, 96 mmol) was heated at 120° C. for 1 h under argon. After the mixture was cooled to 0° C., ethyl acrylate (10.4 mL, 96 mmol) was carefully added dropwise, and the resulting mixture was stirred at 50° C. for 2 h. Then the mixture was cooled to room temperature, dibromoethane (40.0 mL) was added, and the mixture was stirred for 5 h at 120° C. The formed trimethylbromosilane and excess dibromoethane were removed under vacuum. Then 100 mL of aqueous ethanol (1:1) were added dropwise to the residue and refluxed for 0.5 h. Then the solvent was removed under vacuum and extracted with ethyl acetate. The organic layer was dried over magnesium sulfate and the solvent was removed under vacuum to give the title compound 4 (10.85 g, 41% yield). $^1$H NMR (300 MHz, CD$_3$OD): δ 1.26 (t, J=7.1 Hz, 3H), 2.07 (m, 2H), 2.42 (m, 2H), 2.62 (m, 2H), 3.59 (m, 2H), 4.15 (q, J=7.1 Hz, 2H). $^{31}$P NMR (100 MHz, CD$_3$OD): δ 49.5; ESI MS m/z− C$_7$H13BrO$_4$P (M-H), cacld. 271.98, found 271.97.

Example 2. Ethyl 3-[2-Bromoethyl(ethoxy)phosphinyl]propanoate (5) and Ethyl 3-[Ethoxy(vinyl)phosphinyl]propanoate (6)

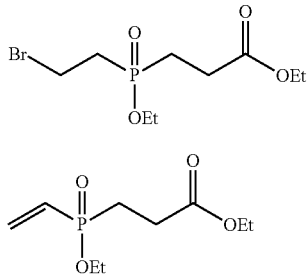

5

6

An amount of 10.84 g of 4 (20 mmol) was treated with 100.0 mL of triethyl orthoformate, and the mixture was refluxed with a Dean-Stark trap to remove ethanol and ethyl formate. Excess triethyl orthoformate was removed under vacuum to give 5 and 6 ([39.2:60.8 $^{31}$P NMR ratio], 11.83 g). 6: $^1$H NMR (300 MHz, CD$_3$OD) δ 1.27 (m, 6H), 2.19 (m, 2H), 2.57 (m, 2H), 4.11 (m, 4H), 6.36 (m, 3H). $^{31}$P NMR (100 MHz, CD$_3$OD): δ 44.9; 5: $^{31}$P NMR (100 MHz, CD$_3$OD) δ 53.3; ESI MS m/z+, 5: 323.01 (M+Na), 6: 243.09 (M+Na).

Example 3. Ethyl 3-((2-(acetylthio)ethyl)(ethoxy)phosphoryl)propanoate (7)

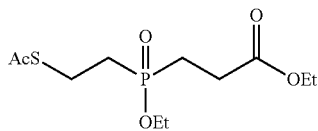

The mixture of compound 5 and 6 (10.0 g, 38.4 mmol estimated from above ratio) in 100 ml of THF at 20° C. was added drop wise the mixture of thioacetic acid (3.0 ml, 42.0 mmol) and DIPEA (8.5 ml, 48.9 mmol) in 50 ml of dry THF in 1.5 hour. After 24 h under Ar, the mixture was concentrated, diluted with EtOAc/Hexane, washed with 1.0 M NaH$_2$PO$_4$, dried over MgSO$_4$, filtered, evaporated, and SiO$_2$ chromatographic purification (1:12 to 1:10 EtOAc/Hexane) to afford the title compound 7 (10.01 g (88%% yield). ESI MS m/z+ 319.08 (M+Na).

Example 4. 3-(Hydroxy(2-(pyridin-2-yldisulfanyl)ethyl)phosphoryl)propanoic acid (8)

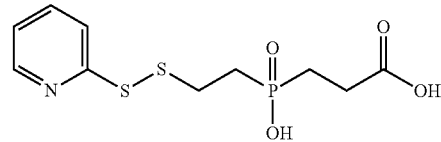 [SMILES: O=C(O)CCP(=O)(O)CCSSc1ccccn1]

Compound 7 (5.00 g, 16.89 mmol) in 100 ml of methanol was added 50 ml of 3 M NaOH. After being stirred under Ar for 3 h, the mixture was neutralized with 3 M H$_3$PO$_4$ to pH 7.2 under Ar. The mixture was added dropwise to the solution of 1,2-bis(5-nitropyridin-2-yl)disulfane (20.0 g, 64.4 mmol) in 200 ml of methanol. After being stirred for 4 h under Ar, the mixture was concentrated, diluted with EtOAc/Hexane (1:1), separated, and the organic layer was washed with pure water (3×25 ml) while the generated each of aqueous layer was washed with EtOAc/Hexane (1:1, 35 ml). The aqueous layers were combined, acidified with HCl/HOAc to pH 3~4, concentrated to ~10 ml, diluted with MeCN (60 ml), sonicated (or quickly stirred) for 1 h, filtered, washed the pellet with water/MeCN (1:10). The solution was then concentrated and purified on a SiO$_2$ column eluted with water/MeCN/HOAc (1:10:0.01), pooled the fraction, added DMF (~5 ml), evaporated to dryness to afford the title compound 8 (4.41 g, 85% yield). ESI MS, m/z− 306.01 (M-H).

Example 5. (3-((2,5-Dioxopyrrolidin-1-yl)oxy)-3-oxopropyl)(2-(pyridin-2-yldisulfanyl)ethyl)phosphinic acid (9)

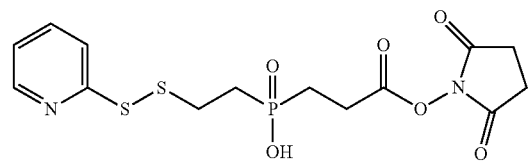 [SMILES: O=C(CCP(=O)(O)CCSSc1ccccn1)ON1C(=O)CCC1=O]

Compound 8 (2.20 g, 7.16 mmol) in DMA (50 ml) was added 0.2 ml of HCl (conc) and the mixture was evaporated to dryness. Then the compound redissolved in dry DMA (60 ml) was added, NHS (0.90 g, 7.82 mmol) and EDC (3.00 g, 15.62 mmol). The mixture was stirred under Ar overnight, evaporated and purified on SiO$_2$ chromatography eluted with 4:1:1% Acetone/DCM/HOAc, pooled the fractions, evaporated and solidified with EtOH/Tol/Hexane to afford the title compound (2.11 g, 73% yield). $^1$H NMR (DMSO-d6, 300 MHz) 8.39 (dd, 1H, J=3.5, 4.7 Hz), 7.84 (m, 2H), 7.24 (m, 1H), 2.93~2.89 (m, 2H), 2.74 (s, 4H), 2.41~2.37 (m, 2H), 2.09~2.03 (m, 4H); MS m/z− 403.2 (M-H).

Example 6. 3,6-endoxo-Δ-tetrahydrophthalhide (15)

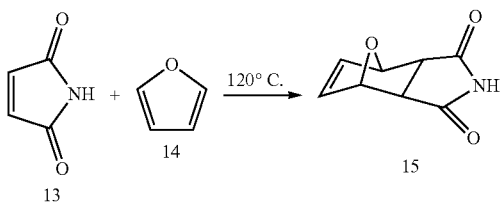 [SMILES: O=C1C=CC(=O)N1 ; c1ccoc1 ; O=C1NC(=O)C2C3C=CC(O3)C12]

Maleimide (10.0 g, 103.0 mmol) in ethylether (350 ml) was added furan (11.0 ml, 151.2 mmol). The mixture was heated inside a 1 L of autoclave bomb at 100° C. for 8 h. The bomb was cooled down to room temperature, and the inside solid was rinsed with methanol, concentrated and crystallized in ethyl acetate/hexane to afford 16.9 g (99%) of the title compound. $^1$H NMR (DMF-d7, 300 MHz): 11.06 (s, 1H) (NH), 6.61 (m, 2H), 5.15 (m, 2H), 2.97 (m, 2H). $^{13}$C NMR 178.86, 137.72, 82.05, 49.93. MS m/z+ 188.4 (M+Na).

Example 7. Ethyl ((3,6-endoxo-Δ-tetrahydrophthalido)-ethyl)(ethoxy)phosphoryl)propanoate or ethyl 3-((2-((3aR,4R,7S)-1,3-dioxo-3a,4,7,7a-tetrahydro-1H-4,7-epoxyisoindol-2(3H)-yl)ethyl)(ethoxy)phosphoryl)propanoate (16)

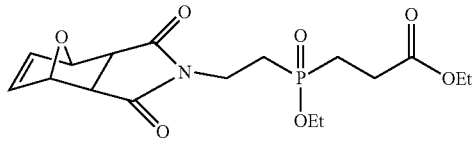 [SMILES: CCOC(=O)CCP(=O)(CCN1C(=O)C2C3C=CC(O3)C2C1=O)OCC]

3,6-Endoxo-Δ-tetrahydrophthalhide (2.40 g, 14.55 mmol) in DMA (60 ml) was added K$_2$CO$_3$ (4.2 g, 30.39 mmol) and KI (0.40 g, 3.45 mmol). After stirring under Ar for 1 hr, the mixture of compound 5 and 6 (2.6 g, 10.0 mmol estimated from above ratio) in DMA (10 ml) was added. The mixture was stirred under Ar overnight, evaporated, re-dissolved in EtOAc (100 ml), washed with water (2×50 ml) and 1.0 M NaH$_2$PO$_4$ (2×50 ml), dried over Na$_2$SO$_4$, filtered, evaporated and purified by SiO$_2$ chromatography and eluted with EtOAc/hexane (1:15~1:8) to afford the title compound (3.11 g, 81% yield). ESI MS m/z+ 408.20 (M+Na).

Example 8. 3-((2-(2,5-Dioxo-2,5-dihydro-1H-pyrrol-1-yl)ethyl)(hydroxy)phosphoryl) propanoic acid or (2'-(N-maleimido)ethyl) (hydroxy)phosphoryl) propanoic acid (17)

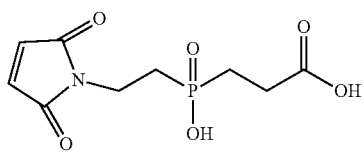 [SMILES: O=C(O)CCP(=O)(O)CCN1C(=O)C=CC1=O]

Compound 16 (3.00 g, 7.79 mmol), in the mixture of DMA (20 ml), toluene (20 ml) and HCl (8N, 10 ml) was heated at 120~140° C. for 8 h. During the reaction time, 5×10 ml of water was gradually added to keep the reaction volume around 40 ml. The mixture was concentrated and purified by SiO$_2$ chromatography eluted with (1:10:0.01 to 1:8:0.01) water/CH$_3$CN/HOAc to afford the title compound (1.55 g, 76% yield). ESI MS m/z− 260.10 (M-H).

Example 9. (2-(2,5-Dioxo-2,5-dihydro-1H-pyrrol-1-yl)ethyl)(3-((2,5-dioxopyrrolidin-1-yl)oxy)-3-oxopropyl)phosphinic acid (18)

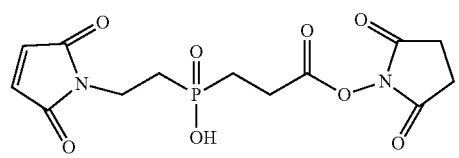 [SMILES: O=C(CCP(=O)(O)CCN1C(=O)C=CC1=O)ON1C(=O)CCC1=O]

Compound 17 (1.50 g, 5.74 mmol) in DMA (50 ml) was added 0.1 ml of HCl (conc) and the mixture was evaporated to dryness. Then the compound redissolved in dry DMA (40 ml) was added, NHS (0.71 g, 6.01 mmol) and EDC (3.00 g, 15.62 mmol). The mixture was stirred under Ar overnight, evaporated and purified on SiO$_2$ chromatography eluted with 4:1:1% Acetone/DCM/HOAc, pooled the fractions, evaporated and solidified with EtOH/Tol/Hexane to afford the title compound (1.56 g, 76% yield). ESI MS m/z− 357.20 (M-H).

Example 10. (3-bromobutyl)(3-ethoxy-3-oxopropyl)phosphinic acid (29)

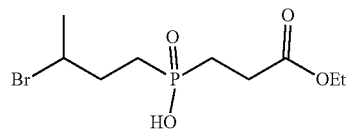

A mixture of ammonium hypophosphite (8.00 g, 96 mmol) and hexamethydisilazane (20.0 mL, 96 mmol) was heated at 120° C. for 1 h under argon. After the mixture was cooled to 0° C., ethyl acrylate (10.4 mL, 96 mmol) was carefully added dropwise, and the resulting mixture was stirred at 50° C. for 2 h. Then the mixture was cooled to room temperature, 1,3-dibromobutane (40.0 mL) was added, and the mixture was stirred for 5 h at 120° C. The formed trimethylbromosilane was removed under vacuum. Then 100 mL of aqueous ethanol (1:1) were added dropwise to the residue, refluxed for 0.5 h and then concentrated under vacuum. The mixture was diluted with water, carefully neutralized to pH 7 with 0.1 M NaOH, extracted with hexane (2×80 ml). The aqueous layer was acidified to pH ~3, extracted with ethyl acetate (3×80 ml). The organic layer (EtOAc) was dried over magnesium sulfate, concentrated under vacuum, and purified on SiO$_2$ eluted with acetone/CH$_2$Cl$_2$ (4:1) to give the title compound 29 (12.38 g, 43% yield). ESI MS m/z− 299.20 (M-H).

Example 11. Ethyl 3-((3-bromobutyl)(ethoxy)phosphoryl)propanoate (30) and ethyl 3-(but-2-en-1-yl(ethoxy)phosphoryl)propanoate (31)

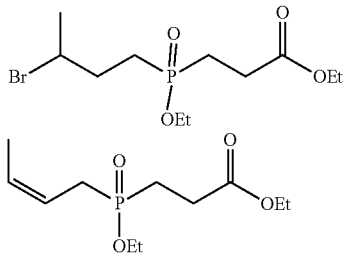

Compound 29 (12.20 g, 40.66 mmol) was treated with 100.0 mL of triethyl orthoformate, and the mixture was refluxed with a Dean-Stark trap to remove ethanol and ethyl formate. Excess triethyl orthoformate was removed under vacuum to give 30 and 31 ([21.8:79.2 $^{31}$P NMR ratio], 10.13 g, 93% yield). ESI MS m/z+ 30: cacld. for $C_{11}H_{22}BrNaO_4P$ 351.04, found 351.20; 31: cacld for $C_{11}H_{21}NaO_4P$ 271.12, found 271.20.

Example 12. Ethyl 3-((3-(acetylthio)butyl)(ethoxy)phosphoryl)propanoate (32)

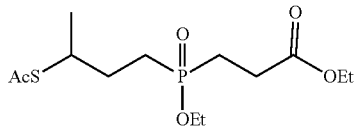

The mixture of compound 30 and 31 (6.1 g, 22.76 mmol estimated from above ratio) in 100 ml of THF was added drop wise the mixture of thiolacetic acid (3.0 ml, 42.0 mmol) and DIPEA (8.5 ml, 48.9 mmol) in 50 ml of THF. After stirred at 50° C. under Ar for 24 h, the mixture was concentrated, diluted with EtAc/Hexane, washed with 1.0 M $NaH_2PO_4$, dried over $MgSO_4$, filtered, evaporated, and $SiO_2$ chromatographic purification (1:12 to 1:10 EtAc/Hexane) to afford the title compound 32 (5.23 g, 71% yield). ESI MS m/z+ 347.20 (M+Na).

Example 13. 3-(hydroxy(3-(pyridin-2-yldisulfanyl)butyl)phosphoryl)propanoic acid (33)

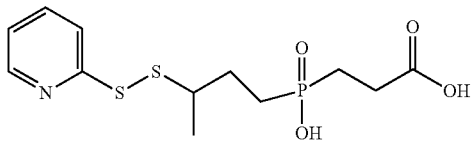 [SMILES: CC(CCP(=O)(O)CCC(=O)O)SSc1ccccn1]

Compound 32 (5.20 g, 16.04 mmol) in 100 ml of methanol was added 50 ml of 3 M NaOH. After being stirred under Ar for 3 h, the mixture was neutralized with 3 M $H_3PO_4$ to pH 7.2 under Ar. The mixture was added dropwise to the solution of 1,2-bis(5-nitropyridin-2-yl)disulfane (20.0 g, 64.4 mmol) in 200 ml of methanol. After being stirred for 4 h under Ar, the mixture was concentrated, diluted with EtOAc/Hexane (1:1), separated, and the organic layer was washed with pure water (3×25 ml) while the generated each of aqueous layer was washed with EtOAc/Hexane (1:1, 35 ml). The aqueous layers were combined, acidified with HCl/HOAc to pH 3~4, concentrated to ~10 ml, diluted with MeCN (60 ml), sonicated (or quickly stirred) for 1 h, filtered, washed the pellet with water/MeCN (1:10). The solution was then concentrated and purified on a $SiO_2$ column eluted with water/MeCN/HOAc (1:10:0.01), pooled the fraction, added DMF (~5 ml), evaporated to dryness to afford the title compound 33 (4.40 g, 81% yield). ESI MS, m/z− 334.10 (M-H).

Example 14. (3-((2,5-dioxopyrrolidin-1-yl)oxy)-3-oxopropyl)(3-(pyridin-2-yl disulfanyl)butyl)phosphinic acid (34)

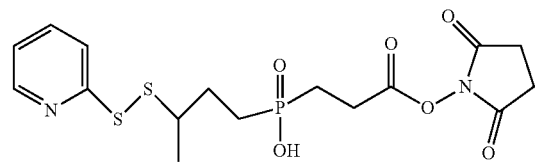 [SMILES: CC(CCP(=O)(O)CCC(=O)ON1C(=O)CCC1=O)SSc1ccccn1]

Compound 33 (2.20 g, 6.56 mmol) in DMA (50 ml) was added 0.2 ml of HCl (conc) and the mixture was evaporated to dryness. Then the compound redissolved in dry DMA (60 ml) was added NHS (0.85 g, 7.39 mmol) and EDC (3.00 g, 15.62 mmol). The mixture was stirred under Ar overnight, evaporated and purified on $SiO_2$ chromatography eluted with 4:1:1% Acetone/DCM/HOAc, pooled the fractions, evaporated and solidified with EtOH/Tol/Hexane to afford the title compound (1.98 g, 70% yield). ESI MS m/z− 431.2 (M-H).

Example 15. (3-bromo-3-methylbutyl)(3-ethoxy-3-oxopropyl)phosphinic acid (37)

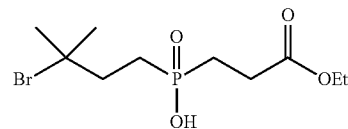 [SMILES: CCOC(=O)CCP(=O)(O)CCC(C)(C)Br]

A mixture of ammonium hypophosphite (8.00 g, 96 mmol) and hexamethydisilazane (20.0 mL, 96 mmol) was heated at 120° C. for 1 h under argon. After the mixture was cooled to 0° C., ethyl acrylate (10.4 mL, 96 mmol) was carefully added dropwise, and the resulting mixture was stirred at 50° C. for 2 h. Then the mixture was cooled to room temperature, 1,3-dibromo-3-methylbutane (44.0 mL) was added, and the mixture was stirred for 5 h at 120° C. The formed trimethylbromosilane was removed under vacuum. Then 100 mL of aqueous ethanol (1:1) were added dropwise to the residue, refluxed for 0.5 h and then concentrated under vacuum. The mixture was diluted with water, carefully neutralized to pH 7 with 0.1 M NaOH, extracted with hexane (2×80 ml). The aqueous layer was acidified to pH ~3, extracted with ethyl acetate (3×80 ml). The organic layer (EtOAc) was dried over sodium sulfate, concentrated under vacuum, and purified on $SiO_2$ eluted with acetone/$CH_2Cl_2$ (4:1) to give the title compound 37 (12.95 g, 43% yield). ESI MS m/z− 313.10 (M-H).

Example 16. Ethyl 3-((3-bromo-3-methylbutyl)(ethoxy)phosphoryl) propanoate (38) and ethyl 3-(ethoxy(3-methylbut-2-en-1-yl)phosphoryl)propanoate (39)

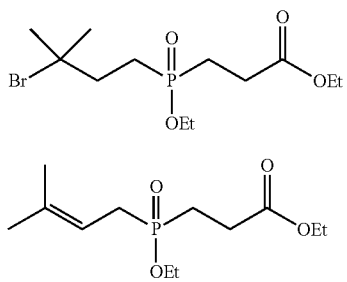

Compound 37 (12.90 g, 41.07 mmol) was treated with 100.0 mL of triethyl orthoformate, and the mixture was refluxed with a Dean-Stark trap to remove ethanol and ethyl formate. Excess triethyl orthoformate was removed under vacuum to give 38 and 39 ([12.5:87.5 $^{31}$P NMR ratio], 9.89 g, 89% yield). ESI MS m/z+ 38: cacld. for $C_{12}H_{24}BrNaO_4P$ 365.06, found 365.10; 39: cacld for $C_{12}H_{23}NaO_4P$ 283.13, found 285.20.

Example 17. Ethyl 3-((3-(acetylthio)-3-methylbutyl)(ethoxy)phosphoryl) propanoate (40)

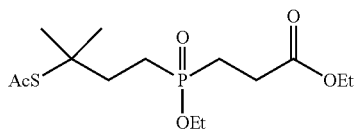

The mixture of compound 38 and 39 (8.5 g, 31.25 mmol estimated from above ratio) in 100 ml of THF was added drop wise the mixture of thiolacetic acid (5.0 ml, 70.0 mmol) and DIPEA (12.5 ml, 71.9 mmol) in 80 ml of THF. After stirred at 70° C. under Ar for 35 h, the mixture was concentrated, diluted with EtAc/Hexane, washed with 1.0 M $NaH_2PO_4$, dried over $MgSO_4$, filtered, evaporated, and $SiO_2$ chromatographic purification (1:12 to 1:10 EtAc/Hexane) to afford the title compound 40 (6.55. g, 62% yield). ESI MS m/z+ 361.20 (M+Na).

Example 18. 3-(hydroxy(3-methyl-3-(pyridin-2-yldisulfanyl)butyl)phosphoryl)propanoic acid (41)

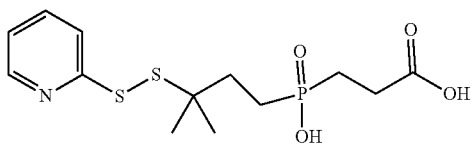 [SMILES: CC(C)(CCP(=O)(O)CCC(=O)O)SSc1ccccn1]

Compound 40 (6.50 g, 19.22 mmol) in 100 ml of methanol was added 50 ml of 3 M NaOH. After being stirred under Ar for 3 h, the mixture was neutralized with 3 M $H_3PO_4$ to pH 7.2 under Ar. The mixture was added dropwise to the solution of 1,2-bis(5-nitropyridin-2-yl)disulfane (20.0 g, 64.4 mmol) in 200 ml of methanol. After being stirred for 24 h under Ar, the mixture was concentrated, diluted with EtOAc/Hexane (1:1), separated, and the organic layer was washed with pure water (3×25 ml) while the generated each of aqueous layer was washed with EtOAc/Hexane (1:1, 35 ml). The aqueous layers were combined, acidified with HCl/HOAc to pH 3~4, concentrated to ~10 ml, diluted with MeCN (60 ml), sonicated (or quickly stirred) for 1 h, filtered, washed the pellet with water/MeCN (1:10). The solution was then concentrated and purified on a $SiO_2$ column eluted with water/MeCN/HOAc (1:10:0.01), pooled the fraction, added DMF (~5 ml), evaporated to dryness to afford the title compound 41 (5.16 g, 77% yield). ESI MS, m/z− 348.12 (M-H).

Example 19. (3-((2,5-dioxopyrrolidin-1-yl)oxy)-3-oxopropyl)(3-methyl-3-(pyridin-2-yldisulfanyl)butyl)phosphinic acid (42)

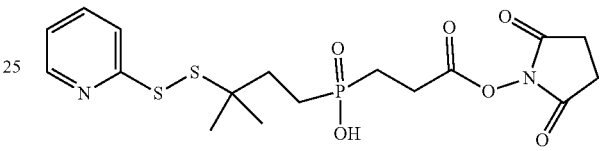

Compound 41 (2.10 g, 6.01 mmol) in DMA (50 ml) was added 0.2 ml of HCl (conc) and the mixture was evaporated to dryness. Then the compound redissolved in dry DMA (60 ml) was added NHS (0.80 g, 6.96 mmol) and EDC (3.00 g, 15.62 mmol). The mixture was stirred under Ar overnight, evaporated and purified on $SiO_2$ chromatography eluted with 4:1:1% Acetone/DCM/HOAc, pooled the fractions, evaporated and solidified with EtOH/Tol/Hexane to afford the title compound (1.93 g, 72% yield). ESI MS m/z− 445.10 (M-H).

Example 20. Modification of Antibody with Phosphinate Linker

The antiHer2 antibody is modified with phosphinate linker at 8 mg/mL antibody, a 10 fold molar excess of phosphinate linker (~30 mM stock solution in DMA). The reaction is carried out in 100 mM $NaH_2PO_4$, pH7.4 buffer with DMA (5% v/v) for 15, 30, 60, 120, and 240 minutes at 25° C. The modified antiHer2 was purified by G25 column with 50 mM $NaH_2PO_4$, 50 mM NaCl, and 2 mM EDTA, pH6.5 to remove the excess phosphinate linker.

Example 21. Conjugate Synthesis

A phosphinate linker containing thiopyridine (SPP) linker was dissolved in DMA at a concentration of approximately 10 mM. An antibody was dialyzed into buffer A (50 mM $NaH_2PO_4$, 50 mM NaCl, 2 mM EDTA, pH 6.5). For the linker reaction, the antibody was at 8 mg/ml, and 4 equivalents of linker were added while stirring in the presence of 5% (v/v) DMA. The reaction was allowed to proceed at ambient temperature for 90 minutes. Unreacted linker was removed from the antibody by Sephadex G25 gel filtration using a Sephadex G25 column equilibrated with Buffer A at pH 6.5 or 150 mM potassium phosphate buffer containing 100 mM NaCl, pH 7.4 as indicated. For the SPP containing linker, the extent of modification was assessed by release of pyridine-2-thione using 50 mM DTT and measuring the absorbance at 343 nm as described below ($\varepsilon_{343}$=8080 M$^{-1}$ cm$^{-1}$ for free pyridine-2-thione). For the conjugation reaction, thiol-containing drug (such tubulysin TZ041) was dissolved in DMA (N,N-dimethylacetamide) at a concentration of approximately 10 mM. The drug (1-1.5-fold molar excess relative to the number of linker molecules per antibody as indicated) was slowly added with stirring to the antibody which was at a concentration of 2.5 mg/ml in buffer A (pH 6.5 or pH 7.4) in a final concentration of 3% (v/v) DMA. The reaction was allowed to proceed at ambient temperature for the indicated times. Drug-conjugated antibody was purified using a Sephadex G25 column equilibrated with buffer B (PBS (NaH$_2$PO$_4$), pH 6.5). The extent of drug conjugation to antibody was assessed by measuring A$_{254}$ and A$_{280}$ of the conjugate.

Example 22. In Vitro Cytotoxicity Evaluation of a Tubulysin (ZT041) Conjugates of Antibodies with a Disulfide Linkers Containing Phosphinate Group The targeted cells (e.g. Ramos cells, 20,000 cells) were cultured in the presence of various concentrations of unconjugated antibody or the antibody conjugate for 96 hours after which cell viability was measured by propidium iodide exclusion and analyzed by flow cytometry using a Becton Dickinson FACSort (Becton Dickinson, Franklin Lakes, N.J.). Red fluorescent intensity (emission at 617 nm in the FL2 channel) of the cells excited at 488 nm was measured. The regions for viable cells were also set using both the forward light scatter and right-angle light scatter properties of the cells. The loss of viability was determined by the loss of cells from within the gated region defining viable cells. The average number of viable cells per 6 replicate cultures was calculated. The survival fraction was plotted versus conjugate concentration to determine the IC$_{50}$ value (50% cell killing concentration) of the conjugate.

REFERENCES

U.S. Pat. Nos. 4,680,338, 5,122,368, 5,141,648, 5,208,020, 5,416,064; 5,475,092, 5,543,390, 5,563,250 5,585,499, 5,880,270, 6,214,345, 6,436,931, 6,372,738, 6,340,701, 6,989,452, 7,129,261, 7,375,078, 7,498,302, 7,507,420, 7,691,962, 7,910,594, 7,968,586, 7,989,434, 7,994,135, 7,999,083, 8,153,768, 8,236,319.
Albrecht, H.; et al. *J. Immunol Methods* 2006, 310, 100.
Alley, S. C.; et al. *Curr Opin Chem Biol* 2010, 14, 529.
Anderson, D. C.; et al. *Bioconjug Chem* 1993, 4, 10.
Antczak, C.; et al. *Bioconjug Chem* 2006, 17, 1551.
Aoki, S.; et al. *Bioorg Med Chem* 2009, 17, 3405.
Austin, C. D.; et al. *Proc Natl Acad Sci USA* 2005, 102, 17987.
Barbour, N. P.; et al. *Pharm Res* 1995, 12, 215.
Beeson, C.; et al. *Bioconjug Chem* 2003, 14, 927.
Bickel, U.; et al. *Bioconjug Chem* 1995, 6, 211.
Chen, J.; et al. *Expert Opin Drug Deliv* 2005, 2, 873.
DiJoseph, J. F.; et al. *Blood* 2004, 103, 1807.
Doronina, S. O.; et al. *Bioconjugate Chem.*, 2006, 17, 114.
Doronina, S. O.; et al. *Bioconjug Chem* 2008, 19, 1960.
Ebner, A.; et al. *Bioconjug Chem* 2007, 18, 1176.
Erickson, H. K.; et al. *Bioconjug Chem* 2010, 21, 84.
Garsky, V. M.; et al. *J. Med. Chem.*, 2001, 4216.
Greenwald, R. B.; et al. *J. Med. Chem.*, 1999, 42, 3657.
Haenseler, E.; et al. *Biochemistry,* 1992, 31, 891.
Hamann, P. R.; et al. *Bioconjugate Chem.*, 2002, 13, 40.
Hamann, P. R.; et al. *Bioconjugate Chem.*, 2005, 16, 354.
Jeffrey, S. C.; et al. *J. Med. Chem.,* 2005, 48, 1344
Johnson, D. A.; et al. *Cancer Res* 1991, 51, 5774.
Jones, D. S.; et al. *Bioconjug Chem* 2001, 12, 1012.
Jones, D. S.; et al. *Bioconjug Chem* 1999, 10, 480.
Jones, D. S.; et al. *Bioconjug Chem* 1994, 5, 390.
Kashef, N.; et al. *J Med Microbiol* 2006, 55, 1441.
Kellogg, B. A.; et al. *Bioconjug Chem* 2011, 22, 717.
Kelly, R. K.; et al. *Eur J Cancer* 2011, 47, 1736.
King, H. D.; et al. *Bioconjug Chem* 1999, 10, 279.
King, H. D.; et al, *J. Med. Chem.,* 2002, 45, 4336
Klussman, K.; et al. *Bioconjug Chem* 2004, 15, 765.
Kovář, M.; et al. *Bioconjugate Chem.,* 2002, 13, 206.
Kratz, F., et al. *J. Med. Chem.,* 2002, 45, 5523.
Kumaresan, P. R.; et al. *Bioconjug Chem* 2008, 19, 1313.
Kumaresan, P. R.; et al. *Bioconjug Chem* 2007, 18, 175.
Lee, L. S.; et al. *Bioconjug Chem* 1999, 10, 973.
Li, L.; et al. *Bioconjug Chem* 2002, 13, 985.
Lipinski, T.; et al. *Glycoconj J* 2011, 28, 149.
Meyer-Losic, F.; et al. *J. Med. Chem.,* 2006, 49, 6908
Mikolajczyk, S. D.; et al. *Bioconjug Chem* 1994, 5, 636.
Miller, M. L.; et al. *J. Med. Chem.,* 2004, 47, 4802
Mitchell, J. S.; et al. *Bioconjug Chem* 2007, 18, 268.
Moon, S.-J.; et al. *J Med. Chem.,* 2008, 51, 6916
Ojima, I.; et al. *J. Med. Chem.,* 2002, 45, 5620
Ruppert, C.; et al. *Bioconjug Chem* 2002, 13, 804.
Safavy, A.; et al. *Bioconjug Chem* 2003, 14, 302.
Safavy, A.; et al. *Bioconjug Chem* 2004, 15, 1264.
Senter, P. et al. *Photochem. Photobio.,* 1985, 42, 231.
Scott, C. F., Jr.; et al. *J Natl Cancer Inst* 1987, 79, 1163.
Sharkey, R. M.; et al. *Mol Cancer Ther* 2012, 11, 224.
Siiman, O.; et al. *Bioconjugate Chem.,* 2000, 11, 549.
Skwarczynski, M.; et al. *J. Med. Chem.,* 2006, 49, 7253
Srinivasachar, K.; Neville, D. M., Jr. *Biochemistry* 1989, 28, 2501.
Studer, M.; et al. *Bioconjug Chem* 1992, 3, 424.
Sun, X.; et al. *Bioconjug Chem* 2011, 22, 728.
Suzawa, T.; et al. *Bioorg Med Chem* 2000, 8, 2175.
Tadayoni, B. M.; et al. *Bioconjug Chem* 1993, 4, 139.
ten Hoeve, W.; et al. *Bioconjug Chem* 1997, 8, 257.
Tsai, N. M.; et al. *Biotechniques* 2001, 30, 396.
Walker, M. A.; rt al. *Bioorg Med Chem Lett* 2004, 14, 4323.
Wilbur, D. S.; et al. *Bioconjug Chem* 2011, 22, 1089.
Widdison, W. C.; et al al. *J. Med. Chem.,* 2006, 49, 4392.
Zhao, R. Y.; et al. *J. Med. Chem.,* 2011, 54, 3606
Zhao, R. Y.; et al. *J. Med. Chem.,* 2012, 55, 766

What is claimed is:
1. A cell-binding agent-drug conjugate of formula (II)

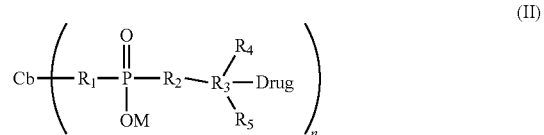

wherein:
Cb represents a cell-binding agent which is an antibody, or a fragment thereof;
Drug represents a drug;
n is an integer from 1 to 20; and
the cell-binding agent-drug conjugate of formula (II) is formed by reacting a functional group on the drug with Z in a compound of formula (I), and reacting a functional group on the cell-binding agent with Y:

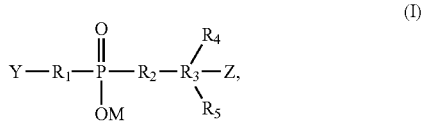
(I)

wherein Y is selected from the group consisting of an unsubstituted or substituted N-hydroxysuccinimide ester, hydrazide, p-nitrophenyl ester, dinitrophenyl ester, pentafluorophenyl ester, pyridyldisulfide, nitropyridyldisulfide, unsubstituted or substituted maleimido, β-maleimidopropionamido, haloacetate and carboxylic acid halide;

Z is a thiol, disulfide, pyridyldisulfide, —$ONH_2$, carboxy, aldehyde, ketone, azide, unsubstituted or substituted maleimido, N-hydroxy succinimide ester, haloacetyl, halogen, hydrazine or hydroxy group;

M is H, Na, K, $N^+R_1R_2R_3$ or a pharmaceutical salt thereof;

$R_1$ and $R_2$ are the same or different and are a linear alkyl having from 1 to 6 carbon atoms, branched or cyclic alkyl having from 3 to 6 carbon atoms, a linear, branched or cyclic alkenyl or alkynyl having from 2 to 6 carbon atoms, a polyethyleneoxy unit of formula $(OCH_2CH_2)_p$, wherein p is an integer from 1 to about 1000, or a combination thereof;

$R_3$ is absent, a linear alkyl having from 1 to 6 carbon atoms, branched or cyclic alkyl having from 3 to 6 carbon atoms, a linear, branched or cyclic alkenyl or alkynyl having from 2 to 6 carbon atoms, a polyethyleneoxy unit of formula $(OCH_2CH_2)_p$, wherein p is an integer from 1 to about 1000, or a combination thereof; and $R_4$, and $R_5$, are the same or different and are absent, H, a linear alkyl having from 1 to 6 carbon atoms, branched or cyclic alkyl having from 3 to 6 carbon atoms, linear, branched or cyclic alkenyl or alkynyl having from 2 to 6 carbon atoms, or polyethyleneoxy unit of formula $(OCH_2CH_2)_{p-1}OCH_2CH_3$, wherein p−1 is an integer from 1 to about 1000, or a combination thereof.

2. The cell-binding agent-drug conjugate of claim 1, wherein the Drug is selected from the group consisting of
1). chemotherapeutic agents:
   a). alkylating agents selected from the group consisting of Nitrogen mustards selected from the group consisting of chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, and uracil mustard; CC-1065 and adozelesin, carzelesin and bizelesin compounds thereof; duocarmycin; benzodiazepine dimers selected from the group consisting of dimers of pyrrolobenzodiazepine, tomaymycin, indolinobenzodiazepines, imidazobenzothiadiazepines, and oxazolidinobenzodiazepines; nitrosoureas selected from the group consisting of carmustine, lomustine, chlorozotocin, fotemustine, nimustine, and ranimustine; alkylsulphonates selected from the group consisting of busulfan, treosulfan, improsulfan and piposulfan; triazenes (dacarbazine); platinum containing compounds selected from the group consisting of carboplatin, cisplatin, and oxaliplatin; aziridines selected from the group consisting of benzodopa, carboquone, meturedopa, and uredopa; ethylenimines and methylamelamines selected from the group consisting of altretamine, triethylenemelamine, trietylenephosphoramide, triethylenethiophosphaoramide and trimethylolomelamine;
   b). plant alkaloids selected from the group consisting of Vinca alkaloids selected from the group consisting of vincristine, vinblastine, vindesine, vinorelbine, and navelbin; Taxoids selected from the group consisting of paclitaxel, and docetaxol; maytansinoids selected from the group consisting of DM1, DM2, DM3, DM4, DM5, DM6, DM7, maytansine and ansamitocins; cryptophycins selected from the group consisting of cryptophycin 1 and cryptophycin 8; epothilones, eleutherobin, discodermolide, bryostatins, dolostatins, auristatins, tubulysins, cephalostatins; pancratistatin; a sarcodictyin; and spongistatin;
   c). DNA topoisomerase inhibitors selected from the group consisting of Epipodophyllins selected from the group consisting of 9-aminocamptothecin, camptothecin, crisnatol, daunomycin, etoposide, etoposide phosphate, irinotecan, mitoxantrone, novantrone, retinoic acids (retinols), teniposide, topotecan, and 9-nitrocamptothecin; and mitomycins (mitomycin C);
   d). anti-metabolites selected from the group consisting of anti-folate which is selected from the group consisting of DHFR inhibitors selected from the group consisting of methotrexate, trimetrexate, denopterin, pteropterin, and aminopterin; IMP dehydrogenase inhibitors selected from the group consisting of mycophenolic acid, tiazofurin, ribavirin, and EICAR; ribonucleotide reductase inhibitors selected from the group consisting of hydroxyurea, and deferoxamine; pyrimidine compounds selected from the group consisting of uracil compounds selected from the group consisting of ancitabine, azacitidine, 6-azauridine, capecitabine, carmofur, cytarabine, dideoxyuridine, doxifluridine, enocitabine, 5-fluorouracil, floxuridine, and ratitrexed; cytosine compounds selected from the group consisting of cytarabine, cytosine arabinoside, and fludarabine; purine compounds selected from the group consisting of azathioprine, fludarabine, mercaptopurine, thiamiprine, and thioguanine; and folic acid replenisher (frolinic acid);
   e). hormonal therapies selected from the group consisting of receptor antagonists selected from the group consisting of anti-estrogen selected from the group consisting of megestrol, raloxifene, and tamoxifen; LHRH agonists selected from the group consisting of goscrclin, and leuprolide acetate; anti-androgens selected from the group consisting of bicalutamide, flutamide, calusterone, dromostanolone propionate, epitiostanol, goserelin, leuprolide, mepitiostane, nilutamide, testolactone, and trilostane; retinoids/deltoids which is selected from the group consisting of Vitamin D3 compounds selected from the group consisting of CB 1093, EB 1089 KH 1060, cholecalciferol, and ergocalciferol; photodynamic therapies selected from the group consisting of verteporfin, phthalocyanine, photosensitizer Pc4, and demethoxy-hypocrellin A; cytokines selected from the group consisting of Interferon-alpha, Interferon-gamma, tumor necrosis factor (TNFs), and human proteins containing a TNF domain;
   f). kinase inhibitors selected from the group consisting of BMW 2992 (anti-EGFR/Erb2), imatinib, gefitinib, pegaptanib, sorafenib, dasatinib, sunitinib, erlotinib, nilotinib, lapatinib, axitinib, pazopanib, vandetanib, E7080 (anti-VEGFR2), mubritinib, ponatinib, bafetinib, bosutinib, cabozantinib, vismodegib, iniparib, ruxolitinib, CYT387, axitinib, tivozanib, sorafenib, bevacizumab, cetuximab, trastuzumab, ranibizumab, panitumumab, and ispinesib;

g). antibiotics selected from the group consisting of enediyne antibiotics selected from the group consisting of calicheamicins, calicheamicin γ1, γ1, α1 and β1; dynemicin selected from the group consisting of dynemicin A and deoxydynemicin; esperamicin, kedarcidin, C-1027, maduropeptin, neocarzinostatin chromophore and related chromoprotein enediyne antiobiotic chromomophores, aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin;

h). others selected from the group consisting of polyketides (acetogenins), bullatacin and bullatacinone; gemcitabine, epoxomicins (carfilzomib), bortezomib, thalidomide, lenalidomide, pomalidomide, tosedostat, zybrestat, PLX4032, STA-9090, Stimuvax, allovectin-7, Xegeva, Provenge, Yervoy, isoprenylation inhibitors (Lovastatin), dopaminergic neurotoxins (1-methyl-4-phenylpyridinium ion), cell cycle inhibitors (staurosporine), Actinomycins selected from the group consisting of Actinomycin D and dactinomycin, Bleomycins selected from the group consisting of bleomycin A2, bleomycin B2, and peplomycin, anthracyclines selected from the group consisting of daunorubicin, doxorubicin (adriamycin), idarubicin, epirubicin, pirarubicin, zorubicin, and mtoxantrone, MDR inhibitors (verapamil), $Ca^{2+}$ ATPase inhibitors (thapsigargin), histone deacetylase inhibitors selected from the group consisting of Vorinostat, Romidepsin, Panobinostat, valproic acid, Mocetinostat, Belinostat, PCI-24781, Entinostat, SB939, Resminostat, Givinostat, AR-42, CUDC-101, sulforaphane, and Trichostatin A; Thapsigargin, Celecoxib, glitazones, epigallocatechin gallate, Disulfiram, Salinosporamide A; anti-adrenals selected from the group consisting of aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine, elfornithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes selected from the group consisting of T-2 toxin, verrucarin A, roridin A and anguidine; urethane, siRNA, and antisense drugs;

2). anti-autoimmune disease agents: cyclosporine, cyclosporine A, aminocaproic acid, azathioprine, bromocriptine, chlorambucil, chloroquine, cyclophosphamide, corticosteroids selected from the group consisting of amcinonide, betamethasone, budesonide, hydrocortisone, flunisolide, fluticasone propionate, fluocortolone danazol, dexamethasone, triamcinolone acetonide, and beclometasone dipropionate, DHEA, enanercept, hydroxychloroquine, infliximab, meloxicam, methotrexate, mofetil, mycophenylate, prednisone, sirolimus, tacrolimus;

3). anti-infectious disease agents:
a). aminoglycosides: amikacin, astromicin, gentamicin selected from the group consisting of netilmicin, sisomicin, and isepamicin, hygromycin B, kanamycin selected from the group consisting of amikacin, arbekacin, bekanamycin, dibekacin, and tobramycin, neomycin selected from the group consisting of framycetin, paromomycin, and ribostamycin, netilmicin, spectinomycin, streptomycin, tobramycin, verdamicin;

b). amphenicols: azidamfenicol, chloramphenicol, florfenicol, thiamphenicol;

c). ansamycins: geldanamycin, herbimycin;

d). carbapenems: biapenem, doripenem, ertapenem, imipenem/cilastatin, meropenem, panipenem;

e). cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin selected from the group consisting of cefoxitin, cefotetan, and cefmetazole, oxacephem selected from the group consisting of flomoxef, and latamoxef;

f). glycopeptides: bleomycin, vancomycin selected from the group consisting of oritavancin, and telavancin, teicoplanin (dalbavancin), ramoplanin;

g). glycylcyclines (tigecycline);

h). β-lactamase inhibitors: penam (sulbactam, tazobactam), clavam (clavulanic acid);

i). lincosamides: clindamycin, lincomycin;

j). lipopeptides: daptomycin, A54145, calcium-dependent antibiotics;

k). macrolides: azithromycin, cethromycin, clarithromycin, dirithromycin, erythromycin, flurithromycin, josamycin, ketolide selected from the group consisting of telithromycin, and cethromycin, midecamycin, miocamycin, oleandomycin, rifamycins selected from the group consisting of rifampicin, rifampin, rifabutin, and rifapentine, rokitamycin, roxithromycin, spectinomycin, spiramycin, tacrolimus, troleandomycin, telithromycin;

l). monobactams: aztreonam, tigemonam;

m). oxazolidinones: linezolid;

n). penicillins: amoxicillin, ampicillin selected from the group consisting of pivampicillin, hetacillin, bacampicillin, metampicillin, and talampicillin, azidocillin, azlocillin, benzylpenicillin, benzathine benzylpenicillin, benzathine phenoxymethylpenicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin;

o). polypeptides: bacitracin, colistin, polymyxin B;

p). quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin;

q). streptogramins: pristinamycin, quinupristin/dalfopristin;

r). sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole);

s). steroid antibacterials (fusidic acid);

t). tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (tigecycline);

u). antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (fosfomycin), nitrofurantoin, paclitaxel, platensimycin, pyrazinamide, quinupristin/dalfopristin, rifampicin (rifampin), tazobactam tinidazole, uvaricin;

4). anti-viral drugs:
a). entry/fusion inhibitors: aplaviroc, maraviroc, vicriviroc, gp41 (enfuvirtide), PRO 140, CD4 (ibalizumab);
b). integrase inhibitors: raltegravir, elvitegravir, globoidnan A;
c). maturation inhibitors: bevirimat, vivecon;
d). neuraminidase inhibitors: oseltamivir, zanamivir, peramivir;
e). nucleosides and nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (3'-fluoro-2',3'-dideoxythymidine (FLT) and 3'-fluoro-2',3'-di deoxyguanosine (FLG), fomivirsen, ganciclovir, idoxuridine, lamivudine (3TC), 1-nucleosides (β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT);
f). non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine;
g). protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir;
h). antivirus drugs: abzyme, arbidol, calanolide a, ceragenin, cyanovirin-n, diarylpyrimidines, epigallocatechin gallate, foscarnet, griffithsin, taribavirin (viramidine), hydroxyurea, KP-1461, miltefosine, pleconaril, portmanteau inhibitors, ribavirin, seliciclib;

5). radioactive isotopes selected from the group consisting of $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, and $^{213}Bi$; and 6). pharmaceutically acceptable salts, or acids of any of the above drugs.

3. The cell-binding agent-drug conjugate of claim 1, wherein Drug is selected from the group consisting of tubulysins, calicheamicins, auristatins, maytansinoids, CC-1065 compounds, morpholinos doxorubicins, taxanes, cryptophycins, epothilones, and benzodiazepine dimers selected from the group consisting of dimers of pyrrolobenzodiazepine, tomaymycin, indolinobenzodiazepines, imidazobenzothiadiazepines, and oxazolidinobenzodiazepines, siRNA or a combination thereof, and pharmaceutically acceptable salts, or acids of any of the above.

4. The cell-binding agent-drug conjugate of claim 1, wherein the Drug is selected from the group consisting of a toxin, a chemotherapeutic agent, a drug moiety, an antibiotic, a radioactive isotope, and a nucleolytic enzyme.

5. The cell-binding agent-drug conjugate of claim 1, wherein the Drug is selected from the group consisting of tubulysins, maytansinoids, taxanoids, CC-1065 compounds, daunorubicin and doxorubicin compounds, benzodiazepine dimers selected from the group consisting of dimers of pyrrolobenzodiazepine, tomaymycin, anthramycin, indolinobenzodiazepines, imidazobenzothiadiazepines, and oxazolidinobenzodiazepines, calicheamicins and the enediyne antibiotics, actinomycin, azaserines, bleomycins, epirubicin, tamoxifen, idarubicin, dolastatins/auristatins selected from the group consisting of monomethyl auristatin E, MMAE, MMAF, auristatin PYE, auristatin TP, auristatins 2-AQ, 6-AQ, EB (AEB), and EFP (AEFP), duocarmycins, thiotepa, vincristine, hemiasterlins, and esperamicins.

6. The cell-binding agent-drug conjugate of claim 1, wherein the cell-binding agent binds to target cells which are selected from the group consisting of tumor cells, virus infected cells, microorganism infected cells, parasite infected cells, autoimmune cells, activated cells, myeloid cells, activated T-cells, B cells, or melanocytes; cells expressing the CD19, CD20, CD22, CD30, CD33, CD37, CD38, CD40, CD 51, CD52, CD56, CD66, CD70, CD74, CD79, CD80, CD98, CD125, CD221, CD227, CD262, CD309, CD326, CEACAM3, CEACAM5 (carcinoembryonic antigen), DLL4 (Δ-like-4), EGFR, CTLA4, CXCR4 (CD184), Endoglin (CD105), EPCAM (epithelial cell adhesion molecule), ERBB2 (Epidermal Growth Factor Receptor 2), FCGR1, FOLR (folate receptor,), GD2 ganglioside, G-28 (a cell surface antigen glyvolipid), GD3 idiotype, Heat shock proteins, HER1, HER2, HLA-DR10, HLA-DRB, human chorionic gonadotropin, IGF1R (insulin-like growth factor 1 receptor), IL-2 receptor (interleukin 2 receptor), IL-6R (interleukin 6 receptor), Integrins ($\alpha v\beta 3$, $\alpha 5\beta 1$, $\alpha 6\beta 4$, $\alpha 11\beta 3$, $\alpha 5\beta 5$, $\alpha v\beta 5$), MAGE-1, MAGE-2, MAGE-3, MAGE 4, anti-transferrin receptor, p97, MS4A1 (membrane-spanning 4-domains subfamily A member 1), MUC1 or MUC1-KLH, MUC16 (CA125), CEA, gp100, MART1, MPG, MS4A1 (membrane-spanning 4-domains subfamily A), Nucleolin, Neu oncogene product, P21, Paratope of anti-(N-glycolylneuraminic acid), PLAP-like testicular alkaline phosphatase, PSMA, PSA, ROBO4, TAG 72 (tumor associated glycoprotein 72), T cell transmembrane protein, Tie (CD202b), TNFRSF10B (tumor necrosis factor receptor superfamily member 10B), TNFRSF13B (tumor necrosis factor receptor superfamily member 13B), TPBG (trophoblast glycoprotein), TRAIL-$R_1$ (tumor necrosis apoprosis inducing ligand receptor 1), VCAM-1 (CD106), VEGF, VEGF-A, VEGF-2 (CD309), CanAg, CALLA, and cells expressing insulin growth factor receptor, and epidermal growth factor receptor.

7. The cell-binding agent-drug conjugate of claim 6, wherein the tumor cells are selected from the group consisting of lymphoma cells, myeloma cells, renal cells, breast cancer cells, prostate cancer cells, ovarian cancer cells, colorectal cancer cells, gastric cancer cells, squamous cancer cells, small-cell lung cancer cells, testicular cancer cells, or any cells that grow and divide at an unregulated, quickened pace to cause cancers.

8. The cell-binding agent-drug conjugate of claim 1, wherein the cell-binding agent is an antibody, a single chain antibody, an antibody fragment that binds to the target cell, a monoclonal antibody, a single chain monoclonal antibody, or a monoclonal antibody fragment that binds the target cell, a chimeric antibody, a chimeric antibody fragment that binds to the target cell, a domain antibody, a domain antibody fragment that binds to the target cell, a resurfaced antibody, a resurfaced single chain antibody, or a resurfaced antibody fragment that binds to the target cell, a humanized antibody or a resurfaced antibody, a humanized single chain antibody, or a humanized antibody fragment that binds to the target cell.

9. The cell-binding agent-drug conjugate of claim 1, having a formula Cb-(-L-Drug)$_n$, wherein L comprises one or more linker components of 6-maleimidocaproyl, maleimidopropanoyl, valine-citrulline, alanine-phenylalanine, p-aminobenzyloxycarbonyl, 4-thio-pentanoate, 4-(N-maleimidomethyl)cyclohexane-1-carboxylate, 4-thio-butyrate, maleimidoethyl containing compounds, 4-thio-2-hydroxysulfonyl-butyrate and (4-acetyl)aminobenzoate.

10. The cell-binding agent-drug conjugate of claim 1, having a formula Cb-(-L-Drug)$_n$, wherein L comprises a peptides of 1~20 units of natural or unnatural amino acids, or a p-aminobenzyl unit, or a 6-maleimidocaproyl unit, or a disulfide unit, or a thioether unit, or a hydrozone unit, or an alkoxime unit.

11. The cell-binding agent-drug conjugate of claim 1, having a formula Cb-(-L-Drug)$_n$, wherein L is cleavable by a protease.

12. The cell-binding agent-drug conjugate of claim 1, wherein $R_1$ and $R_2$ are the same or different and are a linear alkyl having from 1 to 6 carbon atoms.

13. The cell-binding agent-drug conjugate of claim 1, wherein $R_3$, $R_4$ and $R_5$ are absent.

14. The cell-binding agent-drug conjugate of claim 1, wherein $R_3$ is a polyethyleneoxy unit of formula (OCH$_2$CH$_2$)$_p$, wherein p is an integer from 1 to about 1000, and $R_4$ and $R_5$ are absent.

15. The cell-binding agent-drug conjugate of claim 14, wherein p is an integer from 1 to 24.

16. The cell-binding agent-drug conjugate of claim 1, wherein M is H.

17. The cell-binding agent-drug conjugate of claim 1, having in vitro, in vivo or ex vivo cell killing activity.

18. A cell-binding agent-drug conjugate having one of following formulae:

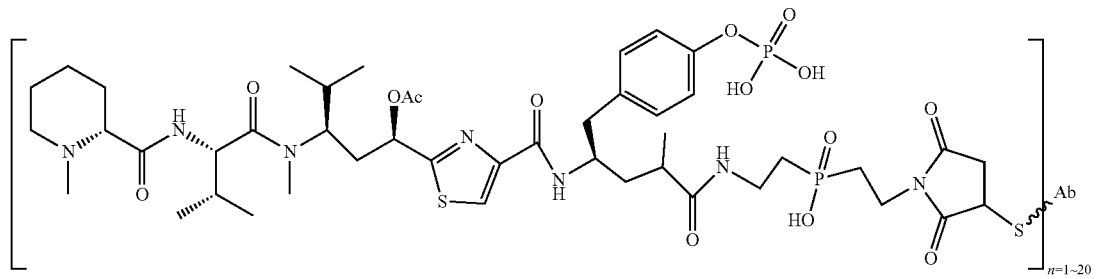

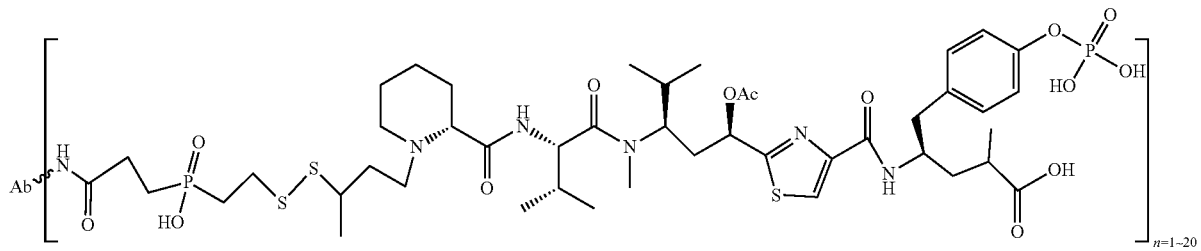

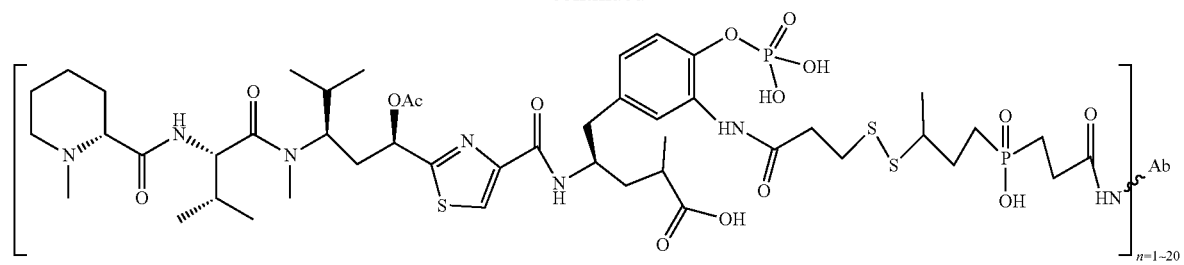
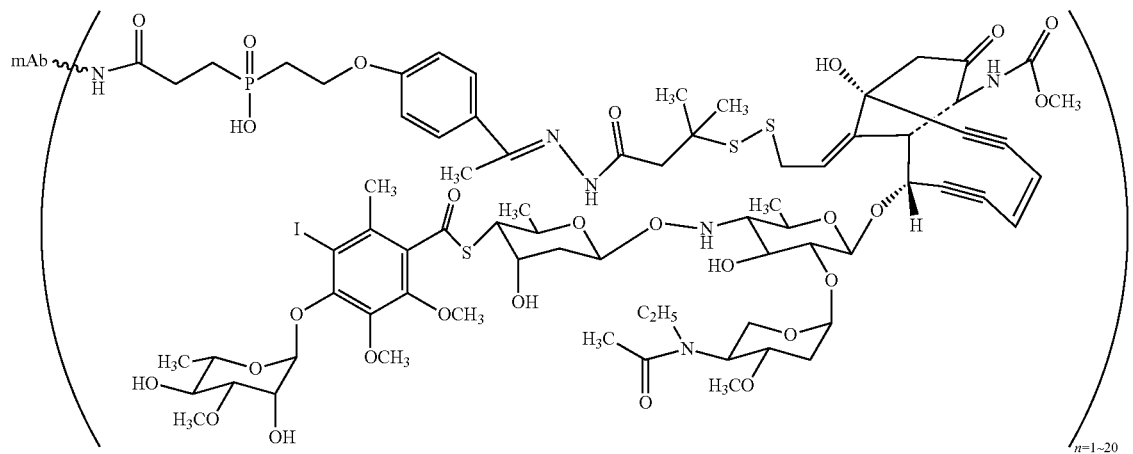
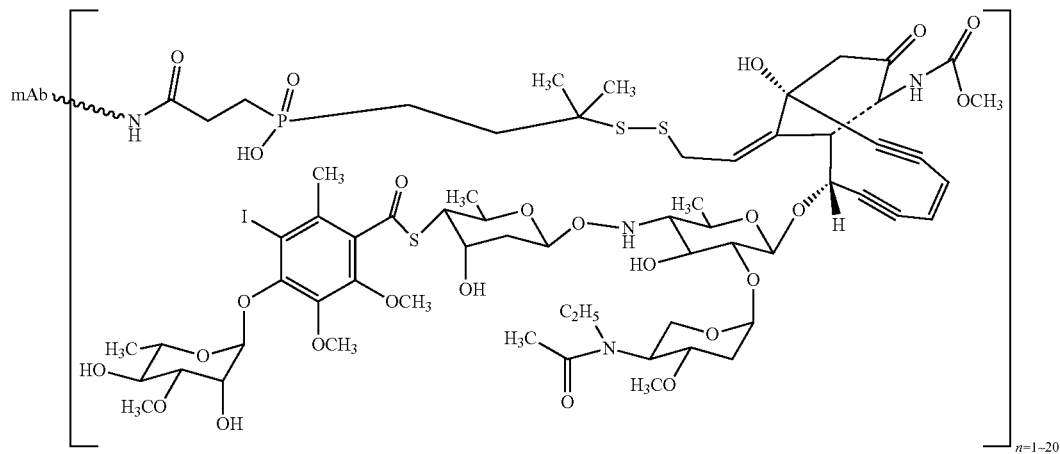
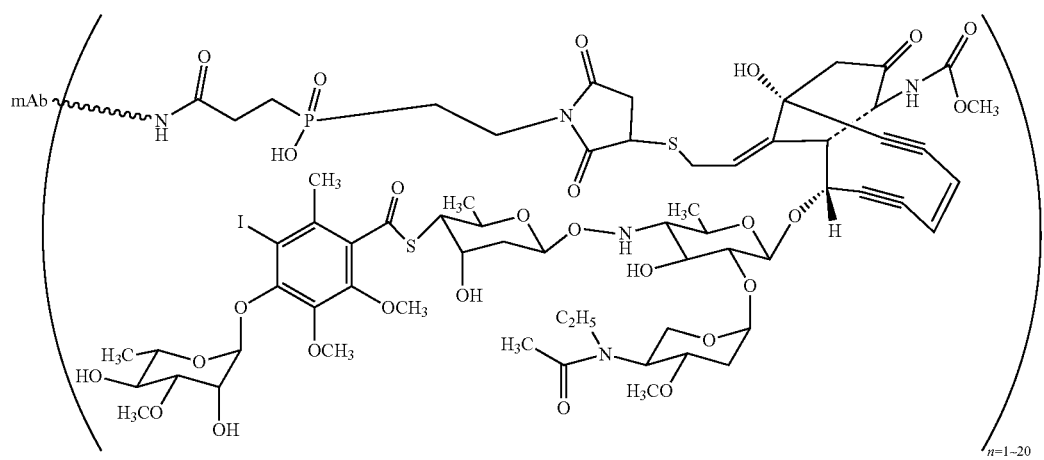

-continued
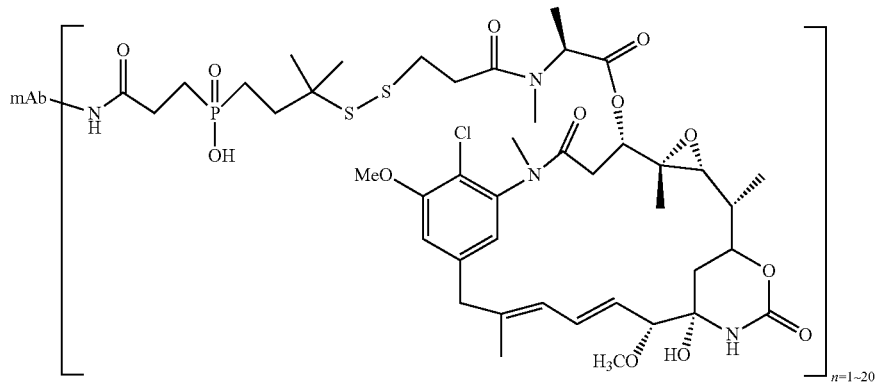
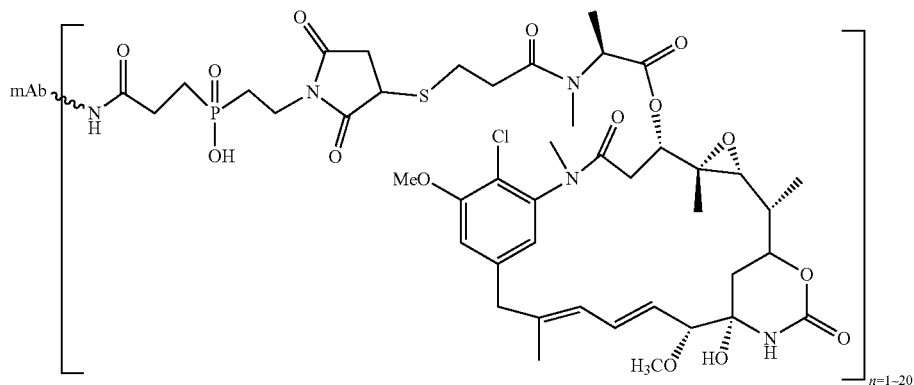
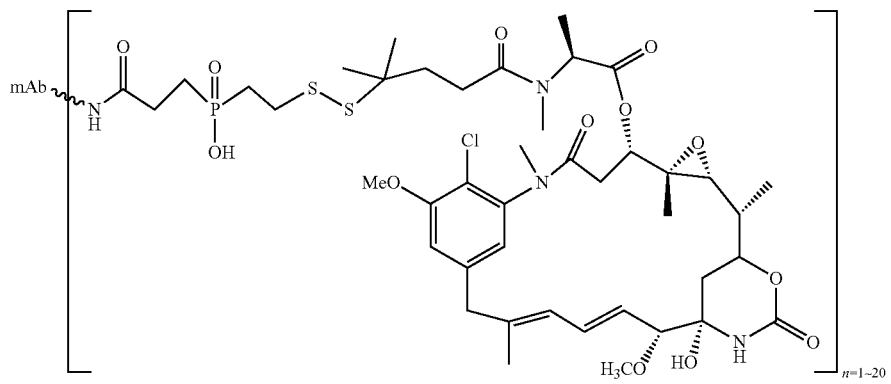
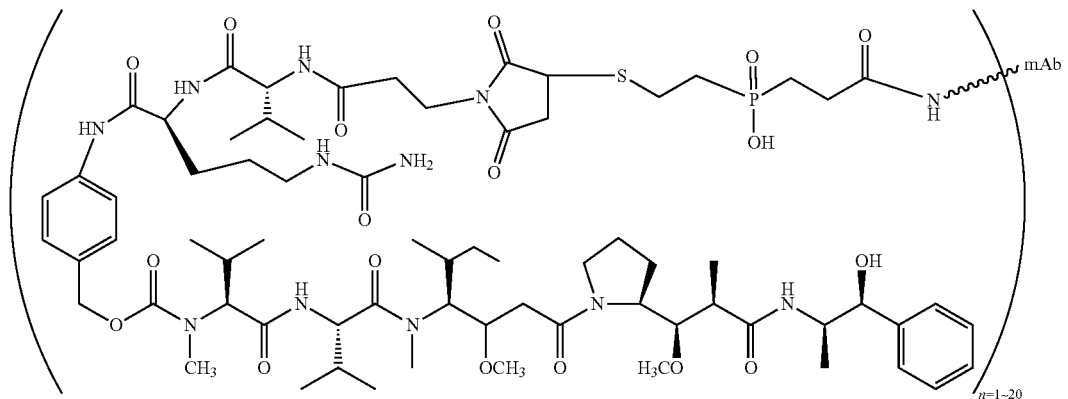

-continued
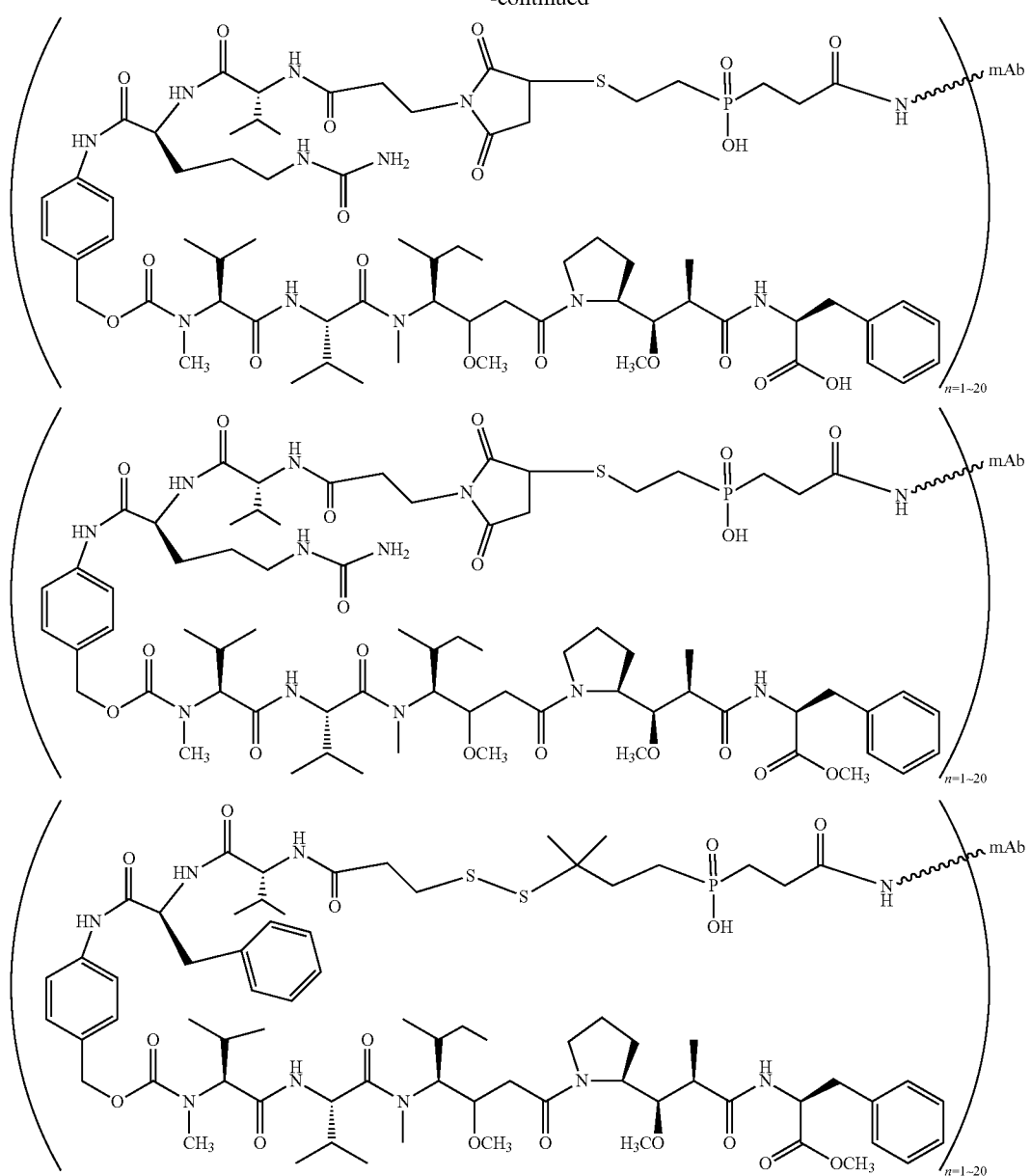
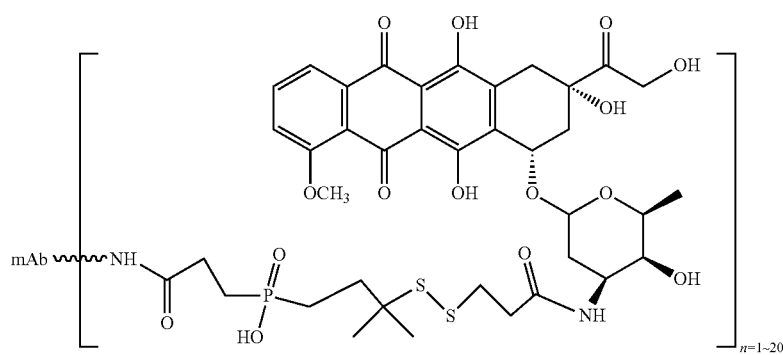

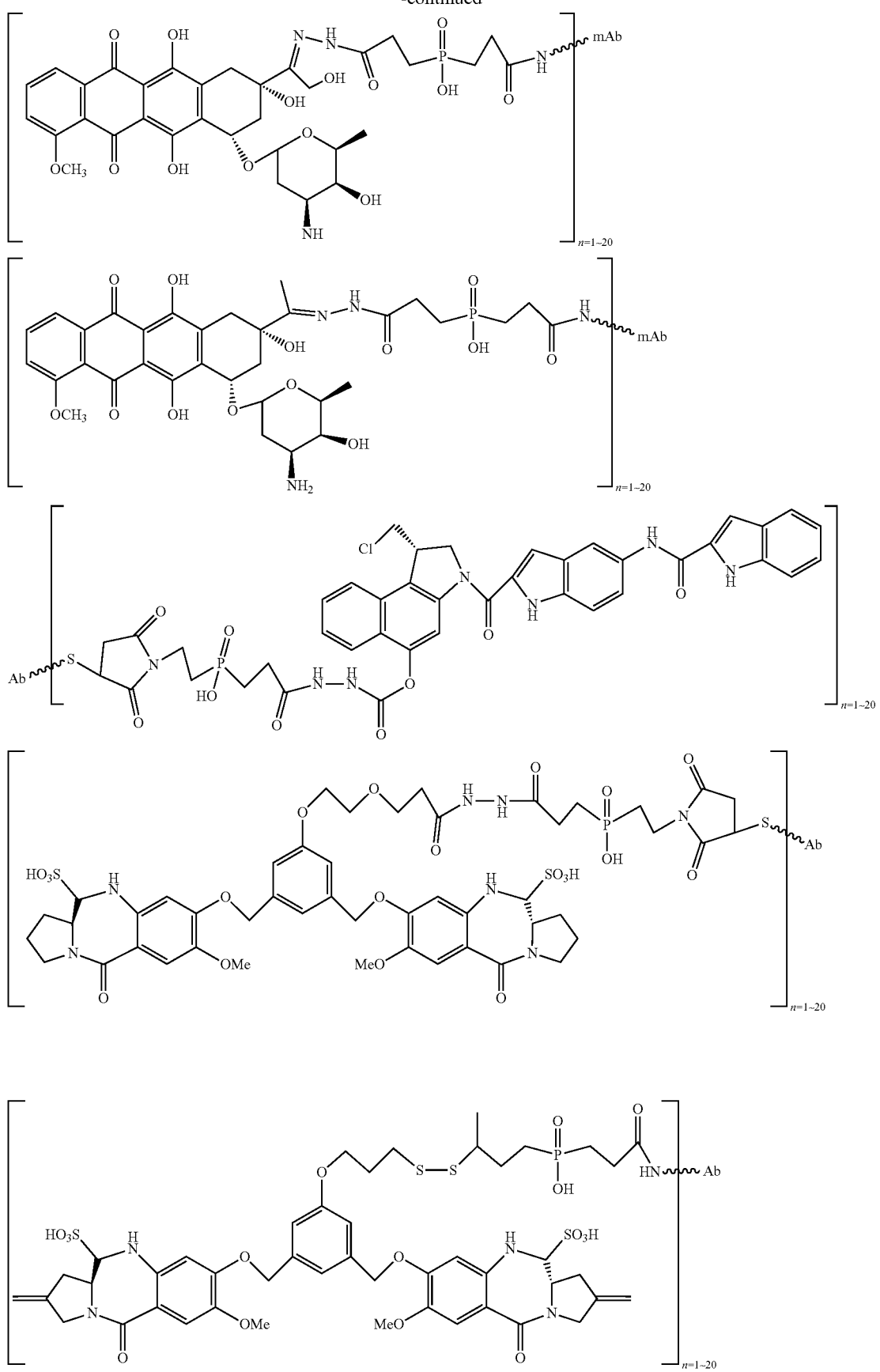

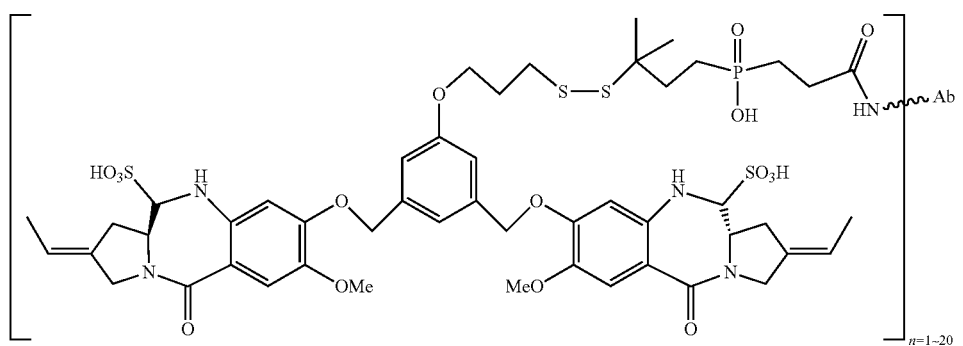
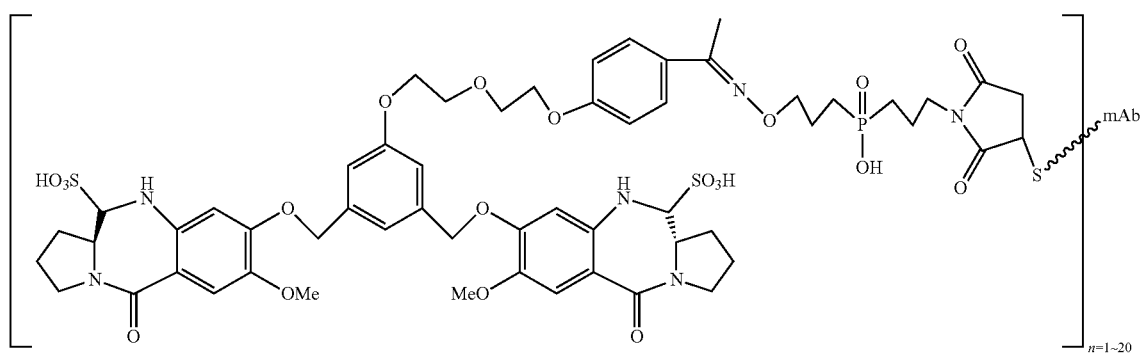
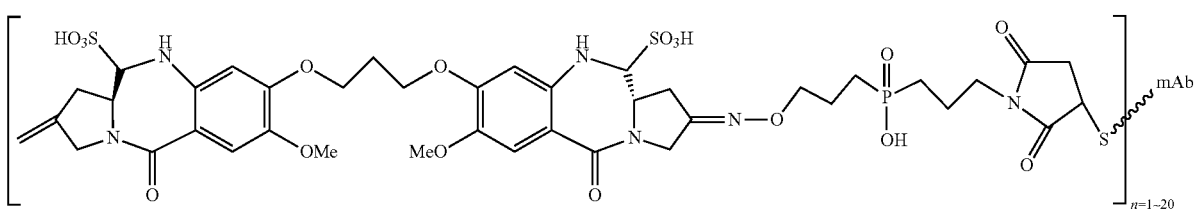
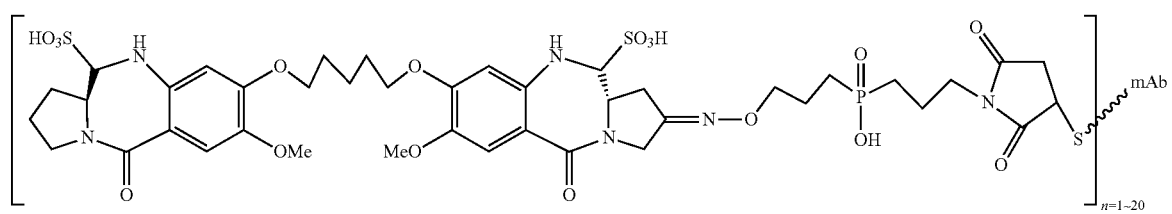
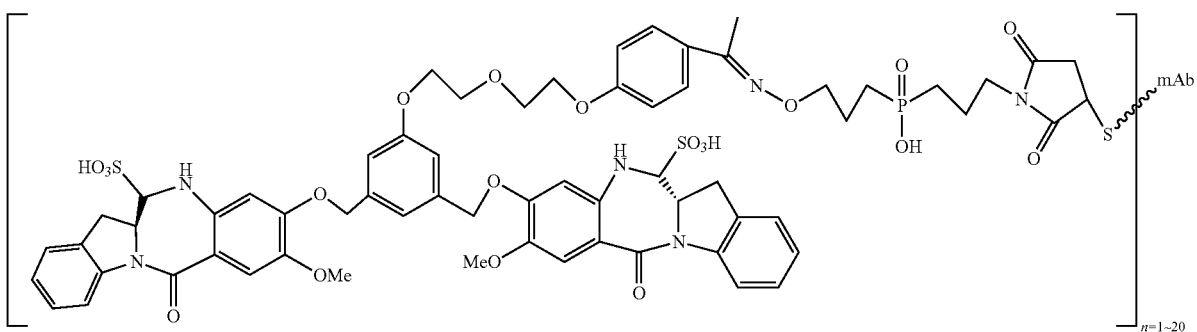

-continued

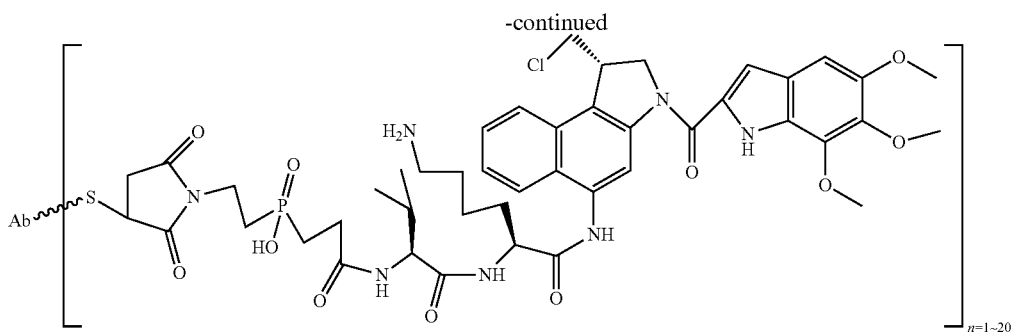

wherein mAb represents a monoclonal antibody, and Ab represents an antibody.

19. The cell-binding agent-drug conjugate of claim 1, having following formula:

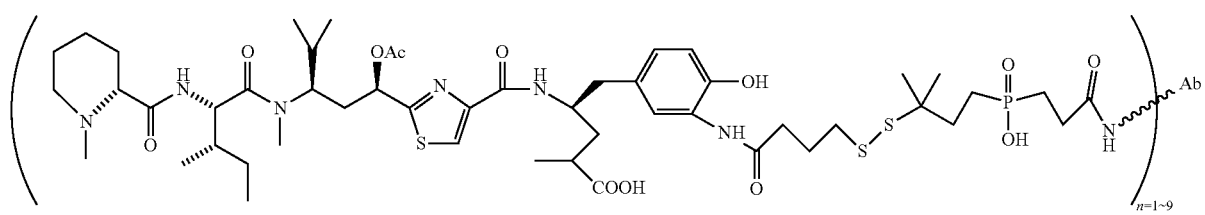

wherein Ab is an antibody.

20. A pharmaceutical composition comprising a therapeutically effective amount of the cell-binding agent-drug conjugate of claim 1, and a pharmaceutically acceptable salt, carrier, diluent, or excipient therefore, or a combination therefore.

21. A pharmaceutical composition comprising a therapeutically effective amount of the cell-binding agent-drug conjugate of claim 1, and a therapeutic agent selected from the group consisting of a chemotherapeutic agent, a radiation therapy, an immunotherapy agent, an autoimmune disorder agent, and an anti-infectious agent.

22. The compound of claim 1, having a formula Cb-(-L-Drug)$_n$, wherein L comprises a single bond, or a disulfide, thioether, thioester, peptide, hydrazone, ether, ester, carbamate, carbonate, secondary, tertiary or quaternary amine, imine, cycloheteroalkyane, heteroaromatic, oxime or amide linker, which directly connects to the Drug.

23. The compound of claim 1, having a formula Cb-(-L-Drug)$_n$, wherein L comprises

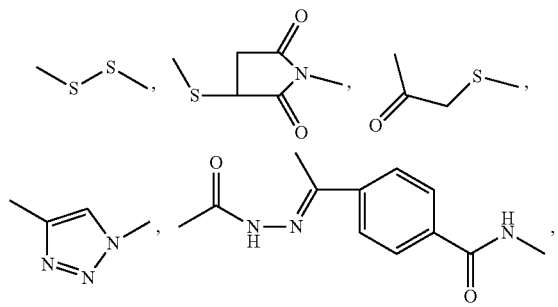

-continued

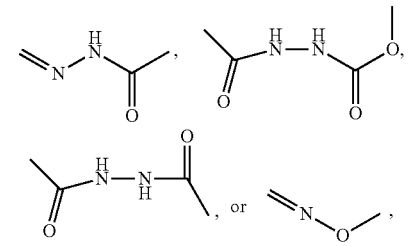

$R_1$ being H, Me, Et or Ph,

R" being H, Me, Et, Pr, Bu or Ph, which directly connects to the Drug.

24. The compound of claim 1, having a formula Cb-(-L-Drug)$_n$, wherein L comprises —O—, —(CO)—O—, —(CO)—NH—, —(CO)—S—, —S—S—,

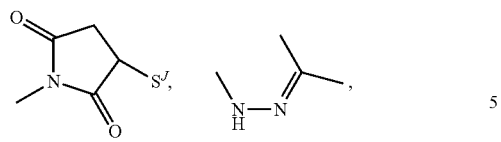

or —S—CH$_2$—(CO)—O— which directly connects to the cell-binding agent.

25. The compound of claim 1, wherein the cell binding agent is selected from the group consisting of polyconal antibodies, monoclonal antibodies, dimers, multimers, multispecific antibodies; single chain antibodies; fragments of antibodies selected from the group consisting of Fab, Fab', F(ab')2, Fv, fragments produced by a Fab expression library, anti-idiotypic antibodies, CDR's, and epitope-binding fragments thereof.

* * * * *